US012807934B2

(12) United States Patent
Geng et al.

(10) Patent No.: US 12,807,934 B2
(45) Date of Patent: Nov. 24, 2026

(54) MULTICOLUMN CHROMATOGRAPHY mRNA PURIFICATION

(71) Applicant: ModernaTX, Inc., Cambridge, MA (US)

(72) Inventors: Mark Geng, Cambridge, MA (US); Jason Murphy, Cambridge, MA (US); Lei Zhou, Hangzhou (CN); James Sinoimeri, Cambridge, MA (US); Tahir Kapoor, Cambridge, MA (US); Joseph Elich, Cambridge, MA (US)

(73) Assignee: ModernaTX, Inc., Cambridge, MA (US)

( * ) Notice: Subject to any disclaimer, the term of this patent is extended or adjusted under 35 U.S.C. 154(b) by 457 days.

(21) Appl. No.: 18/683,285

(22) PCT Filed: Aug. 12, 2022

(86) PCT No.: PCT/US2022/040139

§ 371 (c)(1),
(2) Date: Feb. 13, 2024

(87) PCT Pub. No.: WO2023/018923

PCT Pub. Date: Feb. 16, 2023

(65) Prior Publication Data

US 2024/0368580 A1 Nov. 7, 2024

Related U.S. Application Data

(60) Provisional application No. 63/270,821, filed on Oct. 22, 2021, provisional application No. 63/233,171, filed on Aug. 13, 2021.

(51) Int. Cl.
*C12N 15/10* (2006.01)
*B01D 15/18* (2006.01)
*B01D 15/42* (2006.01)

(52) U.S. Cl.
CPC ....... *C12N 15/101* (2013.01); *B01D 15/1871* (2013.01); *B01D 15/1885* (2013.01); *B01D 15/424* (2013.01)

(58) Field of Classification Search
None
See application file for complete search history.

(56) References Cited

U.S. PATENT DOCUMENTS 5,256,555 A 10/1993 Milburn et al.
5,316,680 A * 5/1994 Frechet ................ B01J 20/3285 530/413
5,644,035 A 7/1997 Koths et al.
5,763,573 A 6/1998 McCormick et al.
8,383,340 B2 2/2013 Ketterer et al.
8,710,200 B2 4/2014 Schrum et al.
8,754,062 B2 6/2014 De Fougerolles et al.
8,822,663 B2 9/2014 Schrum et al.
8,980,864 B2 3/2015 Hoge et al.
8,999,380 B2 4/2015 Bancel et al.
9,045,740 B2 6/2015 Martin et al.
9,221,891 B2 12/2015 Bancel et al.
9,283,287 B2 3/2016 Bancel et al.
9,303,079 B2 4/2016 Bancel et al.
9,464,124 B2 10/2016 Bancel et al.
9,512,456 B2 12/2016 Wang et al.
9,533,047 B2 1/2017 de Fougerolles et al.
9,572,896 B2 2/2017 Bancel et al.
9,597,380 B2 3/2017 Chakraborty et al.
9,675,668 B2 6/2017 Bancel et al.
9,868,691 B2 1/2018 Benenato et al.
9,872,900 B2 1/2018 Ciaramella et al.
10,023,626 B2 7/2018 Bolen et al.
10,064,934 B2 9/2018 Ciaramella et al.
10,064,935 B2 9/2018 Ciaramella et al.
10,124,055 B2 11/2018 Ciaramella et al.
10,207,010 B2 2/2019 Besin et al.
10,232,055 B2 3/2019 Karikóet al.
10,273,269 B2 4/2019 Ciaramella
10,286,086 B2 5/2019 Roy et al.
10,323,076 B2 6/2019 Ellsworth et al.
10,385,088 B2 8/2019 Fraley et al.
10,449,244 B2 10/2019 Ciaramella et al.
10,465,190 B1 11/2019 Chen et al.
10,493,143 B2 12/2019 Ciaramella et al.
10,526,629 B2 1/2020 Rabideau et al.
10,653,712 B2 5/2020 Hoge
(Continued)

FOREIGN PATENT DOCUMENTS

AU 655766 B2 1/1995
CN 102947450 A 2/2013
(Continued)

OTHER PUBLICATIONS

International Search Report and Written Opinion for International Application No. PCT/US2022/040139, mailed Dec. 2, 2022.
[No Author Listed], Oligotex Handbook, Qiagen, Jun. 2012 [retrieved from internet on Sep. 22, 2020] https://www.qiagen.com/au/resources/resourcedetail?id=f9fald98-d54d-47e7-a20b-8b0cb8975009&lang=en.
Gagnon et al., Two new capture options for improved purification of large mRNA, Cell and Gene Therapy Insights, vol. 6, No. 7, Aug. 14, 2020 (Aug. 14, 2020) , pp. 1035-1046.
Gjerde et al., RNA Purification and Analysis: Sample Preparation, Extraction, Chromatography. Appendix 2: "HPLC Instumentation and Operation." WILEY-VCH Verlag GmbH & Co. KGaA, Weinheim ISBN: 978-3-527-32116-2 (Year: 2009). pp. 159-183.
(Continued)

*Primary Examiner* — Patrick T Lewis
(74) *Attorney, Agent, or Firm* — Wolf, Greenfield & Sacks, P.C.

(57) ABSTRACT

Described herein are methods of purifying nucleic acids (e.g., mRNAs) from feed solutions using continuous, multicolumn chromatography approaches. Also described are methods of increasing the efficiency of chromatography methods by performing purification methods in parallel using multiple columns.

20 Claims, 7 Drawing Sheets

(56) References Cited

U.S. PATENT DOCUMENTS

| | | | |
|---|---|---|---|
| 10,653,767 | B2 | 5/2020 | Ciaramella et al. |
| 10,695,419 | B2 | 6/2020 | Ciaramella et al. |
| 10,857,105 | B2 | 12/2020 | Benenato et al. |
| 10,925,958 | B2 | 2/2021 | Ciaramella |
| 11,027,025 | B2 | 6/2021 | Hoge et al. |
| 11,045,540 | B2 | 6/2021 | Ciaramella |
| 11,103,578 | B2 | 8/2021 | Ciaramella et al. |
| 11,174,500 | B2 | 11/2021 | Parella et al. |
| 11,279,923 | B2 | 3/2022 | Funker et al. |
| 11,351,242 | B1 | 6/2022 | Lori et al. |
| 11,384,352 | B2 | 7/2022 | Miracco |
| 11,406,703 | B2 | 8/2022 | Kramarczyk et al. |
| 11,464,848 | B2 | 10/2022 | Ciaramella et al. |
| 11,485,960 | B2 | 11/2022 | Dousis et al. |
| 11,497,807 | B2 | 11/2022 | Ciaramella et al. |
| 11,564,893 | B2 | 1/2023 | Smith |
| 11,576,961 | B2 | 2/2023 | Ciaramella et al. |
| 11,643,441 | B1 | 5/2023 | Ciaramella et al. |
| 11,696,946 | B2 | 7/2023 | Ciaramella |
| 11,752,206 | B2 | 9/2023 | Ciaramella et al. |
| 11,786,607 | B2 | 10/2023 | Hoge et al. |
| 11,851,694 | B1 | 12/2023 | Mauger et al. |
| 11,866,696 | B2 | 1/2024 | Issa et al. |
| 11,872,278 | B2 | 1/2024 | Ciaramella et al. |
| 11,905,525 | B2 | 2/2024 | Brito et al. |
| 11,911,453 | B2 | 2/2024 | Ciaramella et al. |
| 11,912,982 | B2 | 2/2024 | Issa et al. |
| 12,070,495 | B2 | 8/2024 | Lusso et al. |
| 2002/0003109 | A1 | 1/2002 | Gjerde et al. |
| 2008/0220471 | A1 | 9/2008 | Davis et al. |
| 2013/0102034 | A1 | 4/2013 | Schrum et al. |
| 2013/0236974 | A1 | 9/2013 | De Fougerolles |
| 2013/0245103 | A1 | 9/2013 | de Fougerolles et al. |
| 2013/0259923 | A1 | 10/2013 | Bancel et al. |
| 2014/0142290 | A1 | 5/2014 | Madden et al. |
| 2014/0147432 | A1 | 5/2014 | Bancel et al. |
| 2014/0148502 | A1 | 5/2014 | Bancel et al. |
| 2014/0193482 | A1 | 7/2014 | Bancel et al. |
| 2014/0206752 | A1 | 7/2014 | Afeyan et al. |
| 2014/0378538 | A1 | 12/2014 | Bancel |
| 2015/0051268 | A1 | 2/2015 | Bancel et al. |
| 2015/0056253 | A1 | 2/2015 | Bancel et al. |
| 2015/0141499 | A1 | 5/2015 | Bancel et al. |
| 2015/0307542 | A1 | 10/2015 | Roy et al. |
| 2015/0315541 | A1 | 11/2015 | Bancel et al. |
| 2016/0024140 | A1 | 1/2016 | Issa et al. |
| 2016/0024141 | A1 | 1/2016 | Issa et al. |
| 2016/0032273 | A1 | 2/2016 | Shahrokh et al. |
| 2016/0032316 | A1 | 2/2016 | Weissman et al. |
| 2016/0038612 | A1 | 2/2016 | Hoge et al. |
| 2016/0194368 | A1 | 7/2016 | Hoge et al. |
| 2016/0194625 | A1 | 7/2016 | Hoge et al. |
| 2016/0243221 | A1 | 8/2016 | Hoge et al. |
| 2016/0326575 | A1 | 11/2016 | Von Der Mülbe et al. |
| 2017/0043037 | A1 | 2/2017 | Karikóet al. |
| 2017/0130255 | A1 | 5/2017 | Wang et al. |
| 2017/0202979 | A1 | 7/2017 | Chakraborty et al. |
| 2017/0204152 | A1 | 7/2017 | Nelson et al. |
| 2018/0000953 | A1 | 1/2018 | Almarsson et al. |
| 2018/0002393 | A1 | 1/2018 | Bancel et al. |
| 2018/0237849 | A1 | 8/2018 | Thompson |
| 2018/0243225 | A1 | 8/2018 | Ciaramella |
| 2018/0243230 | A1 | 8/2018 | Smith |
| 2018/0251754 | A1 | 9/2018 | DeRosa et al. |
| 2018/0256628 | A1 | 9/2018 | Hoge et al. |
| 2018/0271795 | A1 | 9/2018 | Martini et al. |
| 2018/0271970 | A1 | 9/2018 | Ciaramella et al. |
| 2018/0273977 | A1 | 9/2018 | Mousavi et al. |
| 2018/0274009 | A1 | 9/2018 | Marquardt et al. |
| 2018/0298372 | A1 | 10/2018 | Funkner et al. |
| 2018/0303929 | A1 | 10/2018 | Ciaramella et al. |
| 2018/0311336 | A1 | 11/2018 | Ciaramella et al. |
| 2018/0311343 | A1 | 11/2018 | Huang et al. |
| 2018/0318409 | A1 | 11/2018 | Valiante et al. |
| 2018/0369374 | A1 | 12/2018 | Frederick et al. |
| 2018/0371047 | A1 | 12/2018 | Ticho et al. |
| 2019/0002890 | A1 | 1/2019 | Martini et al. |
| 2019/0008938 | A1 | 1/2019 | Ciaramella et al. |
| 2019/0085368 | A1 | 3/2019 | Bancel et al. |
| 2019/0125839 | A1 | 5/2019 | Frederick et al. |
| 2019/0175517 | A1 | 6/2019 | Martini et al. |
| 2019/0175727 | A1 | 6/2019 | Huang et al. |
| 2019/0192646 | A1 | 6/2019 | Cohen et al. |
| 2019/0192653 | A1 | 6/2019 | Hoge et al. |
| 2019/0275170 | A1 | 9/2019 | Benenato et al. |
| 2019/0298657 | A1 | 10/2019 | Martini et al. |
| 2019/0298658 | A1 | 10/2019 | Benenato |
| 2019/0300906 | A1 | 10/2019 | Martini et al. |
| 2019/0314292 | A1 | 10/2019 | Benenato et al. |
| 2019/0336452 | A1 | 11/2019 | Brader |
| 2019/0351040 | A1 | 11/2019 | Valiante et al. |
| 2019/0382774 | A1 | 12/2019 | Hoge et al. |
| 2019/0390181 | A1 | 12/2019 | Benenato et al. |
| 2020/0030432 | A1 | 1/2020 | Ciaramella et al. |
| 2020/0032274 | A1 | 1/2020 | Mauger et al. |
| 2020/0038499 | A1 | 2/2020 | Narayanan et al. |
| 2020/0054737 | A1 | 2/2020 | Ciaramella et al. |
| 2020/0069599 | A1 | 3/2020 | Smith et al. |
| 2020/0071689 | A1 | 3/2020 | Miracco |
| 2020/0085916 | A1 | 3/2020 | Martini et al. |
| 2020/0109420 | A1 | 4/2020 | Brito et al. |
| 2020/0129445 | A1 | 4/2020 | Patel et al. |
| 2020/0129608 | A1 | 4/2020 | Ciaramella et al. |
| 2020/0129615 | A1 | 4/2020 | Ciaramella et al. |
| 2020/0239869 | A1 | 7/2020 | Issa et al. |
| 2020/0254086 | A1 | 8/2020 | Hoge et al. |
| 2020/0282047 | A1 | 9/2020 | Ciaramella et al. |
| 2020/0306191 | A1 | 10/2020 | Schariter et al. |
| 2020/0338004 | A1 | 10/2020 | Hansson et al. |
| 2020/0368162 | A1 | 11/2020 | Martini |
| 2021/0046173 | A1 | 2/2021 | Ciaramella et al. |
| 2021/0087135 | A1 | 3/2021 | Benenato et al. |
| 2021/0163919 | A1 | 6/2021 | Issa et al. |
| 2021/0187097 | A1 | 6/2021 | Ciaramella et al. |
| 2021/0206818 | A1 | 7/2021 | Huang et al. |
| 2021/0217484 | A1 | 7/2021 | Giessel et al. |
| 2021/0228707 | A1 | 7/2021 | Mektar et al. |
| 2021/0268086 | A1 | 9/2021 | Zhong et al. |
| 2021/0309976 | A1 | 10/2021 | Dousis et al. |
| 2021/0378980 | A1 | 12/2021 | Horhota et al. |
| 2022/0031631 | A1 | 2/2022 | Almarsson et al. |
| 2022/0047518 | A1 | 2/2022 | Hennessy et al. |
| 2022/0054653 | A1 | 2/2022 | Martini et al. |
| 2022/0062175 | A1 | 3/2022 | Smith et al. |
| 2022/0062408 | A1 | 3/2022 | Kramarczyk et al. |
| 2022/0125899 | A1 | 4/2022 | Ashburn et al. |
| 2022/0145381 | A1 | 5/2022 | Elich et al. |
| 2022/0236253 | A1 | 7/2022 | Hopson |
| 2022/0241399 | A1 | 8/2022 | Lusso et al. |
| 2022/0347292 | A1 | 11/2022 | Panther et al. |
| 2022/0348900 | A1 | 11/2022 | Shamashkin et al. |
| 2022/0349006 | A1 | 11/2022 | Amato et al. |
| 2023/0000970 | A1 | 1/2023 | Nachbagauer et al. |
| 2023/0142529 | A1 | 5/2023 | White et al. |
| 2023/0181481 | A1 | 6/2023 | White et al. |
| 2023/0190761 | A1 | 6/2023 | Brader et al. |
| 2023/0212645 | A1 | 7/2023 | Marquardt et al. |
| 2023/0287437 | A1 | 9/2023 | Smith et al. |
| 2023/0338506 | A1 | 10/2023 | Shaw et al. |
| 2023/0346914 | A1 | 11/2023 | Stewart-Jones et al. |
| 2023/0355743 | A1 | 11/2023 | Stewart-Jones et al. |
| 2024/0100145 | A1 | 3/2024 | Bollman et al. |
| 2024/0100151 | A1 | 3/2024 | Carfi et al. |
| 2024/0139309 | A1 | 5/2024 | Carfi et al. |
| 2024/0173400 | A1 | 5/2024 | Ciaramella et al. |
| 2024/0181030 | A1 | 6/2024 | Himansu et al. |
| 2024/0207392 | A1 | 6/2024 | Chandramouli et al. |
| 2024/0209068 | A1 | 6/2024 | Deal et al. |
| 2024/0226028 | A1 | 7/2024 | Goldman et al. |
| 2024/0226277 | A1 | 7/2024 | Nachbagauer et al. |
| 2024/0229109 | A1 | 7/2024 | Rabideau et al. |
| 2024/0238211 | A1 | 7/2024 | Brader et al. |
| 2024/0263226 | A1 | 8/2024 | Schmitt |

(56) References Cited

U.S. PATENT DOCUMENTS

| | | | |
|---|---|---|---|
| 2024/0285754 A1 | 8/2024 | Stewart-Jones |
| 2024/0293534 A1 | 9/2024 | Stewart-Jones |
| 2024/0299531 A1 | 9/2024 | Stewart-Jones |

FOREIGN PATENT DOCUMENTS

| | | | |
|---|---|---|---|
| CN | 108048456 | A | 5/2018 |
| EP | 466688 | B1 | 8/1997 |
| EP | 491828 | B1 | 6/1999 |
| EP | 1462519 | A1 | 9/2004 |
| EP | 2092064 | | 9/2010 |
| JP | 2010-540468 | A | 12/2010 |
| JP | 2011184225 | A | 9/2011 |
| JP | 2012-522020 | A | 9/2012 |
| WO | WO 1995/008626 | A1 | 3/1995 |
| WO | WO 2005/118857 | | 12/2005 |
| WO | WO 2008/077592 | A1 | 7/2008 |
| WO | WO 2009/020710 | A2 | 2/2009 |
| WO | WO 2009/039657 | A1 | 4/2009 |
| WO | WO 2010/111787 | A1 | 10/2010 |
| WO | WO 2011/071931 | A2 | 6/2011 |
| WO | WO 2013/090648 | A1 | 6/2013 |
| WO | WO 2014/004281 | A1 | 1/2014 |
| WO | WO 2014/152031 | A1 | 3/2014 |
| WO | WO 2014/140211 | A1 | 9/2014 |
| WO | WO 2014/144711 | A1 | 9/2014 |
| WO | WO 2014/152030 | A1 | 9/2014 |
| WO | WO 2014/152966 | A1 | 9/2014 |
| WO | WO 2014/159813 | A1 | 10/2014 |
| WO | WO 2015/085318 | A2 | 6/2015 |
| WO | WO 2015/164773 | A1 | 10/2015 |
| WO | WO 2016/051170 | A1 | 4/2016 |
| WO | WO 2016/164762 | A1 | 10/2016 |
| WO | WO 2016/201377 | A1 | 12/2016 |
| WO | WO 2017/011773 | A2 | 1/2017 |
| WO | WO 2017/015457 | A1 | 1/2017 |
| WO | WO 2017/053297 | A1 | 3/2017 |
| WO | WO 2017/066789 | A1 | 4/2017 |
| WO | WO 2017/070601 | A1 | 4/2017 |
| WO | WO 2017/182524 | A1 | 4/2017 |
| WO | WO 2017/112865 | A1 | 6/2017 |
| WO | WO 2017/127750 | A1 | 7/2017 |
| WO | WO 2017/201333 | A1 | 11/2017 |
| WO | WO 2017/205477 | A1 | 11/2017 |
| WO | WO 2018/096179 | A1 | 5/2018 |
| WO | WO 2018/157009 | A1 | 8/2018 |
| WO | WO 2018/232355 | A1 | 12/2018 |
| WO | WO 2018/232357 | A1 | 12/2018 |
| WO | WO 2019/018765 | A1 | 1/2019 |
| WO | WO 2019/036683 | A1 | 2/2019 |
| WO | WO 2019/036685 | A1 | 2/2019 |
| WO | WO 2019/092153 | A1 | 5/2019 |
| WO | WO 2020/097509 | A1 | 11/2019 |
| WO | WO 2020/061367 | A1 | 3/2020 |
| WO | WO 2020/165158 | A1 | 8/2020 |
| WO | WO 2020/185811 | A1 | 9/2020 |
| WO | WO 2020/190750 | A1 | 9/2020 |
| WO | WO 2020/232371 | A1 | 11/2020 |
| WO | WO 2020/243561 | A1 | 12/2020 |
| WO | WO 2021/030533 | A1 | 2/2021 |
| WO | WO 2021/050864 | A1 | 3/2021 |
| WO | WO 2021/055811 | A1 | 3/2021 |
| WO | WO 2021/055849 | A1 | 3/2021 |
| WO | WO 2021/155243 | A1 | 8/2021 |
| WO | WO 2021/155274 | A1 | 8/2021 |
| WO | WO 2021/159040 | A2 | 8/2021 |
| WO | WO 2021/159130 | A2 | 8/2021 |
| WO | WO 2021/211343 | A1 | 10/2021 |
| WO | WO 2021/222304 | A1 | 11/2021 |
| WO | WO 2021/231929 | A1 | 11/2021 |
| WO | WO 2021/231963 | A1 | 11/2021 |
| WO | WO 2021/237084 | A1 | 11/2021 |
| WO | WO 2021/247817 | A1 | 12/2021 |
| WO | WO 2022/032154 | A2 | 2/2022 |
| WO | WO 2022/067010 | A1 | 3/2022 |
| WO | WO 2022/155524 | A1 | 7/2022 |
| WO | WO 2022/155530 | A1 | 8/2022 |
| WO | WO 2022/187698 | A1 | 9/2022 |
| WO | WO 2022/197624 | A1 | 9/2022 |
| WO | WO 2022/204491 | A1 | 9/2022 |
| WO | WO 2022/212191 | A1 | 10/2022 |
| WO | WO 2022/212442 | A1 | 10/2022 |
| WO | WO 2022/212711 | A1 | 10/2022 |
| WO | WO 2022/221335 | A1 | 10/2022 |
| WO | WO 2022/221336 | A1 | 10/2022 |
| WO | WO 2022/221359 | A1 | 10/2022 |
| WO | WO 2022/221440 | A1 | 10/2022 |
| WO | WO 2022/226277 | A1 | 10/2022 |
| WO | WO 2022/226318 | A1 | 10/2022 |
| WO | WO 2022/232585 | A1 | 11/2022 |
| WO | WO 2022/241103 | A1 | 11/2022 |
| WO | WO 2022/245888 | A1 | 11/2022 |
| WO | WO 2022/266010 | A1 | 12/2022 |
| WO | WO 2022/266012 | A1 | 12/2022 |
| WO | WO 2022/266389 | A1 | 12/2022 |
| WO | WO 2023/283642 | A1 | 1/2023 |
| WO | WO 2023/283645 | A1 | 1/2023 |
| WO | WO 2023/283651 | A1 | 1/2023 |
| WO | WO 2023/014649 | A1 | 2/2023 |
| WO | WO 2023/018773 | A1 | 2/2023 |
| WO | WO 2023/018923 | A1 | 2/2023 |
| WO | WO 2023/019181 | A1 | 2/2023 |
| WO | WO 2023/056401 | A1 | 4/2023 |
| WO | WO 2023/069625 | A1 | 4/2023 |
| WO | WO 2023/069895 | A1 | 4/2023 |
| WO | WO 2023/069900 | A1 | 4/2023 |
| WO | WO 2023/076658 | A1 | 5/2023 |
| WO | WO 2023/081311 | A1 | 5/2023 |
| WO | WO 2023/092069 | A1 | 5/2023 |
| WO | WO 2023/107999 | A2 | 6/2023 |
| WO | WO 2023/114307 | A1 | 6/2023 |
| WO | WO 2023/132885 | A1 | 7/2023 |
| WO | WO 2023/137149 | A1 | 7/2023 |
| WO | WO 2023/150256 | A1 | 8/2023 |
| WO | WO 2023/154818 | A1 | 8/2023 |
| WO | WO 2023/196914 | A1 | 10/2023 |
| WO | WO 2023/201204 | A1 | 10/2023 |
| WO | WO 2023/201294 | A1 | 10/2023 |
| WO | WO 2023/201296 | A1 | 10/2023 |
| WO | WO 2023/212696 | A1 | 11/2023 |
| WO | WO 2023/225524 | A1 | 11/2023 |
| WO | WO 2023/250119 | A1 | 12/2023 |
| WO | WO 2024/010993 | A1 | 1/2024 |
| WO | WO 2024/015890 | A1 | 1/2024 |
| WO | WO 2024/026005 | A1 | 2/2024 |
| WO | WO 2024/030369 | A1 | 2/2024 |
| WO | WO 2024/050483 | A1 | 3/2024 |
| WO | WO 2024/097874 | A1 | 5/2024 |
| WO | WO 2024/123978 | A1 | 6/2024 |
| WO | WO 2024/151811 | A1 | 7/2024 |
| WO | WO 2024/163465 | A1 | 8/2024 |
| WO | WO 2024/191860 | A2 | 9/2024 |
| WO | WO 2024/206835 | A1 | 10/2024 |
| WO | WO 2024/215721 | A1 | 10/2024 |

OTHER PUBLICATIONS

Karikó et al., Generating the optimal mRNA for therapy: HPLC purification eliminates immune activation and improves translation of nucleoside-modified, protein-encoding mRNA. Nucleic Acids Res. Nov. 2011;39(21):e142.

Kingston, 'Preparation of poly (A)+ RNA', Current protocols in molecular biology. 1993, vol. 21, No. 1, pp. 4.51-4.5.3.

Ötes et al., Scale-up of continuous multicolumn chromatography for the protein a capture step: From bench to clinical manufacturing. J Biotechnol. Sep. 10, 2018:281:168-174. doi: 10.1016/j.jbiotec.2018.07.022. Epub Jul. 17, 2018.

Ouranidis et al., Pharma 4.0 Continuous mRNA Drug Products Manufacturing. Pharmaceutics. Aug. 31, 2021;13(9):1371. doi: 10.3390/pharmaceutics13091371.

Schmidt et al., Fast and Flexible mRNA Vaccine Manufacturing as a Solution to Pandemic Situations by Adopting Chemical Engineer-

(56) References Cited

OTHER PUBLICATIONS ing Good Practice—Continuous Autonomous Operation in Stainless Steel Equipment Concepts. Processes. 2021;9(11):1874-93.
Slater, The purification of poly(a)-containing RNA by affinity chromatography. Methods Mol Biol. 1985;2:117-20. doi: 10.1385/0-89603-064-4:117.
Triana-Alonso et al., Self-coded 3'-extension of run-off transcripts produces aberrant products during in vitro transcription with T7 RNA polymerase. J Biol Chem. Mar. 17, 1995;270(11):6298-307. doi: 10.1074/jbc.270.11.6298.
Weissman et al., HPLC purification of in vitro transcribed long RNA. Methods Mol Biol. 2013;969:43-54. doi: 10.1007/978-1-62703-260-5_3.
U.S. Appl. No. 18/161,857, filed Jan. 30, 2023, Smith.
U.S. Appl. No. 17/523,034, filed Nov. 10, 2021, Hoge et al.
U.S. Appl. No. 17/523,060, filed Nov. 10, 2021, Hoge et al.
U.S. Appl. No. 17/852,974, filed Jun. 29, 2022, Marquardt et al.
U.S. Appl. No. 16/483,012, filed Aug. 1, 2019, Mauger et al.
U.S. Appl. No. 18/093,119, filed Jan. 4, 2023, Mauger et al.
U.S. Appl. No. 18/448,856, filed Aug. 11, 2023, Rabideau et al.
U.S. Appl. No. 18/318,689, filed May 16, 2023, Hoge et al.
U.S. Appl. No. 17/438,049, filed Sep. 10, 2021, Elich et al.
U.S. Appl. No. 17/634,939, filed Feb. 11, 2022, Shamashkin et al.
U.S. Appl. No. 17/816,696, filed Aug. 1, 2022, Dousis et al.
U.S. Appl. No. 17/761,420, filed Mar. 17, 2022, Amato et al.
U.S. Appl. No. 18/008,139, filed Dec. 2, 2022, Smith et al.
U.S. Appl. No. 17/926,353, filed Nov. 18, 2022, Brader et al.
U.S. Appl. No. 17/925,114, filed Nov. 14, 2022, White et al.
U.S. Appl. No. 18/294,279, filed Feb. 1, 2024, Packer et al.
U.S. Appl. No. 18/702,284, filed Apr. 17, 2024, Smith et al.
U.S. Appl. No. 18/284,938, filed Sep. 29, 2023, Rabideau et al.
U.S. Appl. No. 18/702,280, filed Apr. 17, 2024, Smith.
U.S. Appl. No. 18/560,444, filed Nov. 13, 2023, Schmitt.
U.S. Appl. No. 18/284,395, filed Sep. 27, 2023, Endo et al.
U.S. Appl. No. 18/288,328, filed Oct. 25, 2023, Goldman et al.
U.S. Appl. No. 17/925,125, filed Nov. 14, 2022, White et al.
U.S. Appl. No. 18/570,927, filed Dec. 15, 2023, Ladd Effio et al.
U.S. Appl. No. 18/703,189, filed Apr. 19, 2024, Goldman et al.
U.S. Appl. No. 18/682,685, filed Feb. 9, 2024, Smith.
U.S. Appl. No. 18/707,251, filed May 3, 2024, Smith.
U.S. Appl. No. 18/856,588, filed Oct. 11, 2024, Rabideau et al.
U.S. Appl. No. 18/836,530, filed Aug. 7, 2024, Edwards et al.
U.S. Appl. No. 18/728,664, filed Jul. 12, 2024, Rabideau et al.
U.S. Appl. No. 18/856,118, filed Oct. 11, 2024, Reid.
U.S. Appl. No. 18/085,457, filed Dec. 20, 2022, Joyal et al.
U.S. Appl. No. 18/706,043, filed Apr. 30, 2024, Schneeberger et al.
U.S. Appl. No. 18/719,476, filed Jun. 13, 2024, Brader.
U.S. Appl. No. 18/855,999, filed Oct. 10, 2024, Goldman.
U.S. Appl. No. 18/835,106, filed Aug. 1, 2024, Geng.
U.S. Appl. No. 18/725,999, filed Jul. 1, 2024, Smith.
PCT/US2022/040139, Dec. 2, 2022, International Search Report and Written Opinion.

* cited by examiner

MULTICOLUMN CHROMATOGRAPHY mRNA PURIFICATION

RELATED APPLICATIONS

This application is a national stage filing under 35 U.S.C. § 371 of international PCT Application PCT/US2022/040139, filed Aug. 12, 2022, which claims the benefit under 35 U.S.C. § 119(e) of U.S. provisional Application No. 63/233,171 filed Aug. 13, 2021 and U.S. provisional Application No. 63/270,821 filed Oct. 22, 2021, the contents of each of which are incorporated by reference herein in their entirety.

BACKGROUND

Messenger RNA (mRNA) is an emerging alternative to conventional small molecule and protein therapeutics due to the potency and programmability of mRNA. mRNA encoding a desired therapeutic protein can be administered to a subject for in vivo expression of the protein to therapeutic effect, such as vaccination or replacement of a protein encoded by a mutated gene. In vitro transcription of a DNA template using a bacteriophage RNA polymerase is a useful method of producing mRNAs for therapeutic applications. However, in vitro-transcribed mRNAs must be purified before downstream use.

SUMMARY

Some aspects of the disclosure relate to methods of purifying nucleic acids, such as mRNA, using continuous multicolumn chromatography (MCC) processes. Multicolumn chromatography can load multiple chromatography columns connected in series, such that the flowthrough from one column can be directed onto the stationary phase of one or more secondary columns in series. Any nucleic acids in the flowthrough, or breakthrough, that are not captured by the stationary phase of the first column may be captured by the stationary phase of the secondary columns. By capturing breakthrough from the first column, the secondary column(s) can prevent loss of nucleic acid without markedly reducing the productivity of the process. Thus, a larger amount of nucleic acid may be loaded onto the first column, beyond the resin's binding capacity. Once the first column has been saturated with nucleic acid, the multicolumn chromatography system can adjust the direction of inputs, so that the first column, now saturated with mRNA, is subjected to washing and eluting steps to isolate the bound mRNA. During the washing and elution steps, fresh feed solution can be loaded onto one of the secondary columns, which had previously been receiving flowthrough from the first column to prevent loss of breakthrough mRNA. Once bound nucleic acids have been eluted from the first column, the first column may be regenerated and equilibrated to restore its ability to continue capturing more nucleic acids.

Columns can go through this cycle of 1) equilibration; 2) receiving flowthrough containing nucleic acid from a previous column in series, with this step optionally being repeated; 3) receiving fresh feed solution containing concentrated nucleic acid; 4) washing to remove impurities; 5) elution to collect purified nucleic acid; and 6) regeneration to restore nucleic acid-binding capacity. This cycle allows the nucleic acid feed solution to spend more time in the "mass transfer zone" compared to traditional batch chromatography. In the idle zone of a chromatography column, resin is either already loaded with mRNA and awaiting a washing or elution step, or the resin is freshly regenerated and awaiting fresh nucleic acid load material. In the mass transfer zone, resin is either being actively loaded with nucleic acids, or resin previously loaded with nucleic acid is actively being washed, eluted, regenerated, or equilibrated. The idle zones are unproductive, and represent the majority of a column during traditional batch chromatography. With its simultaneous operation of multiple columns, multicolumn chromatography can divide this productive mass transfer zone across several smaller columns, leading to far higher process productivities compared to traditional batch chromatography. Additionally, by processing smaller columns in parallel, rather than a single column as in traditional batch chromatography methods, the amount of idle time, in which the stationary phase is not interacting with any nucleic acid, is reduced. Thus, multicolumn chromatography has a greater productivity, in terms of nucleic acid that can be purified using a given amount of stationary phase in a given length of time, than batch chromatography methods. Furthermore, the flowthrough of one column may be divided and directed into multiple secondary columns in parallel, allowing more concentrated mRNA feed solutions to be applied to a primary column while minimizing the risk of overloading any of the secondary columns. Use of more concentrated feed solutions, and consequently the ability to purify more mRNA in a given amount of time, offsets the need for additional resin in parallel columns, thereby increasing the productivity of parallel multicolumn chromatography methods relative to batch chromatography methods.

Accordingly, some aspects of the present disclosure comprise methods of purifying a nucleic acid using at least three chromatography columns capable of being used in series, the methods comprising:

(i)(a) loading a first chromatography column by contacting a first stationary phase of the first chromatography column with a feed solution comprising one or more nucleic acids, optionally wherein the one or more nucleic acids comprise mRNAs;

(ii)(a) loading a second chromatography column by contacting, in series with the first chromatography column, a second stationary phase of the second chromatography column with the feed solution that has contacted the first stationary phase of the first column;

(iii)(a) contacting the second stationary phase with a portion of the feed solution that has not been contacted with the first stationary phase;

(iii)(b) contacting, in series with the second chromatography column, a third stationary phase of a third chromatography column with the portion of the feed solution that has contacted the second stationary phase of the second chromatography column; and (iv)(a) eluting the one or more nucleic acids from the first chromatography column.

In some embodiments, the eluting from the first chromatography column is under conditions in which the first and second chromatography columns are not in series.

In some embodiments, the at least three chromatography columns capable of being used in series comprise 3, 4, 5, 6, 7, 8, or more chromatography columns.

In some embodiments, the first chromatography column is capable of being used in series with the eighth and second chromatography column; the second chromatography column is capable of being used in series with the third chromatography column; the third chromatography column is capable of being used in series with the fourth chromatography column; the fourth chromatography column is capable of being used in series with the fifth chromatography column; the fifth chromatography column is capable of being used in series with the sixth chromatography column; the sixth chromatography column is capable of being used in series with the seventh chromatography column; and the seventh chromatography column is capable of being used in series with the eight chromatography column in series.

In some embodiments, the method further comprises:

contacting a last stationary phase of a last chromatography column with an additional portion of the feed solution that has not been contacted with a stationary phase; and contacting, in series with a last chromatography column, the first stationary phase of the first chromatography column with a portion of the additional portion of the feed solution that has contacted the last stationary phase of the last chromatography column.

In some embodiments, output of each chromatography column is not directed into more than one other chromatography column.

In some embodiments, the method further comprises:

(ii)(b) loading a third chromatography column in parallel with the second chromatography column by contacting, in series with the first chromatography column, a third stationary phase of the third chromatography column with a portion the feed solution that has contacted the first stationary phase of the first column.

In some embodiments, the disclosure relates to a method of purifying a nucleic acid using at least four chromatography columns, wherein each column is capable of being used in series and in parallel with two or more other columns, the method comprising:

(i) loading a first chromatography column by contacting a first stationary phase of a first chromatography column with a feed solution comprising one or more nucleic acids, optionally wherein the one or more nucleic acids are mRNAs;

(ii) loading a second chromatography column and a third chromatography column in parallel by contacting, in series with the first chromatography column, (a) a second stationary phase of the second chromatography column with a first portion of the feed solution that has contacted the first stationary phase of the first chromatography column and (b) a third stationary phase of the third chromatography column with a second portion of the feed solution that has contacted the first stationary phase of the first chromatography column;

(iii) loading the second chromatography column by contacting the second stationary phase with a portion of the feed solution that has not been contacted with the first stationary phase;

(iv) loading the third chromatography column and a fourth chromatography column in parallel by contacting, in series with the second chromatography column, (a) the third stationary phase of the third chromatography column with a first portion of the feed solution that has contacted the second stationary phase of the second chromatography column and (b) a fourth stationary phase of the fourth chromatography column with a second portion of the feed solution that has contacted the second stationary phase of the second chromatography column; and (v)(a) eluting the one or more nucleic acids from the first chromatography column.

In some embodiments, the first portion of the feed solution that has contacted the first stationary phase of the first chromatography column is approximately equal to the second portion of the feed solution that has contacted the first stationary phase of the first chromatography column.

In some embodiments, the at least four chromatography columns comprise 4, 5, 6, 7, 8, 9, 10, or more chromatography columns In some embodiments, output of each chromatography column capable of being directed into 2, 3, 4, 5, 6, 7, or 8 other chromatography columns.

In some embodiments, the at least four columns comprise 8 chromatography columns, wherein:

i) the first chromatography column is capable of being used in series with the second and third chromatography columns in parallel;

ii) the second chromatography column is capable of being used in series with the third and fourth chromatography columns in parallel;

iii) the third chromatography column is capable of being used in series with the fourth and fifth chromatography columns in parallel;

iv) the fourth chromatography column is capable of being used in series with the fifth and sixth chromatography columns in parallel;

v) the fifth chromatography column is capable of being used in series with the sixth and seventh chromatography columns in parallel;

vi) the sixth chromatography column is capable of being used in series with the seventh and eighth chromatography columns in parallel;

vii) the seventh chromatography column is capable of being used in series with the eighth and first chromatography columns in parallel; and viii) the eighth chromatography column is capable of being used in series with the first and second chromatography columns in parallel.

In some embodiments, the method further comprises:

contacting a last stationary phase of a last chromatography column with an additional portion of the feed solution that has not been contacted with a stationary phase; and in series with the last chromatography column, contacting in parallel (a) the first stationary phase of the first chromatography column with a first portion of the additional feed solution that has contacted the last stationary phase of the last chromatography column and (b) the second stationary phase of the second chromatography column with a second portion of the additional portion of the feed solution that has contacted the last stationary phase of the last chromatography column.

In some embodiments, the method is an automated method.

In some embodiments, wherein each chromatography column is independently capable of receiving input material from the feed solution, a wash solution, an elution solution, a cleaning solution, and an equilibration solution.

In some embodiments, each chromatography column is independently capable of directing material to a different chromatography column used in series, a waste collection area, and a product collection area.

In some embodiments, the following steps are conducted at the same time: at least one column is loaded; at least one column is washed; at least one column is eluted; at least once column is cleaned; and at least one column is equilibrated.

In some embodiments, the method further comprises:

(ii)(b) contacting the first stationary phase with a washing solution, wherein output comprising the washing solution is directed to a waste collection area.

In some embodiments, the method further comprises:

(iv)(b) contacting the first stationary phase with a cleaning solution, wherein the output comprising the rejuvenation solution is directed to a waste collection area.

In some embodiments, the method further comprises:

(iv)(c) contacting the first stationary phase with an equilibration solution, wherein the output comprising the equilibration solution is directed to a waste collection area.

In some embodiments, each of the at least three stationary phases comprise resin particles.

In some embodiments, the each of the stationary phases comprise oligo-dT.

In some embodiments, each of the at least three chromatography columns comprise a total of about 0.5 L to about 2 L, about 2 L to about 5 L, about 5 L to about 10 L, or about 10 L to about 20 L of stationary phase.

In some embodiments, the feed solution comprises about 2 mg/mL to about 5 mg/mL mRNA, about 2.25 mg/mL to about 4 mg/mL mg/mL mRNA, or about 2.5 mg/mL to about 3 mg/mL mRNA.

In some embodiments, the loading of the first chromatography column comprises contacting the first stationary phase with at least 2 g, at least 3 g, at least 4 g, at least 5 g, at least 6 g, at least 7 g, at least 8 g, at least 9 g, at least 10 g, or more mRNA per L of stationary phase present in the first chromatography column.

In some embodiments, the feed solution has a salt concentration of about 300 mM to about 600 mM. In some embodiments, wherein the feed solution has a salt concentration of about 500 mM, In some embodiments, the salt concentration is the concentration of sodium chloride in the feed solution.

In some embodiments a high-salt buffer is added to the feed solution before the loading of (i)(a), wherein the loading of (i)(a) occurs within 5 minutes or less, 4 minutes or less, 3 minutes or less, 2 minutes or less, or 1 minute or less of the addition of the high-salt buffer.

In some embodiments, the contacting of step (i)(a) is performed for about 2 minutes to about 10 minutes, about 3 minutes to about 7 minutes, or about 5 minutes to about 6 minutes.

In some embodiments, the eluting of (iv)(a) is performed for about 1 minute to about 4 minutes, about 1.25 minutes to about 3 minutes, or about 1.5 minutes to about 2 minutes.

In some embodiments, at least 0.25 g, at least 0.5 g, at least 0.75, at least 2 g, at least 3 g, at least 4 g, at least 5 g, at least 6 g, at least 7 g, at least 8 g, at least 9 g, or up to 10 g of mRNA is eluted per liter of stationary phase comprised in all columns per hour of performing the method, optionally wherein at least 4 g of mRNA is eluted per liter of stationary phase comprised in all columns per hour of performing the method.

In some embodiments, at least 80%, at least 85%, at least 90%, at least 95%, at least 96%, at least 97%, at least 98%, at least 99%, or up to 100% of eluted mRNAs comprise a polyA tail, optionally wherein at least 95% of eluted mRNAs comprise a polyA tail.

In some embodiments, at least 80%, at least 85%, at least 90%, at least 95%, at least 96%, at least 97%, at least 98%, at least 99%, or up to 100% of eluted mRNAs have about the same length, optionally wherein at least 85% of eluted mRNAs have about the same length.

In some embodiments, at least 80%, at least 85%, at least 90%, at least 95%, at least 96%, at least 97%, at least 98%, at least 99%, or up to 100% of the mRNAs of the feed solution are eluted, optionally wherein at least 75% of the mRNAs of the feed solution are eluted.

In some embodiments, the productivity of the method is a least about 0.25 g/L·hr, optionally wherein the productivity of the method is about 0.5 g/L·hr, about 0.75 g/L·hr, about 2 g/L·hr, about 3 g/L·hr, about 4 g/L·hr, about 5 g/L·hr, about 6 g/L·hr, about 7 g/L·hr, about 8 g/L·hr, about 9 g/L·hr, about 10 g/L·hr, or more.

BRIEF DESCRIPTION OF THE DRAWINGS

FIG. 2A describes a first step in a multicolumn chromatography process, in which a feed solution containing mRNA is added to column 1, breakthrough from column 1 is directed into column 2, column 3 is equilibrated to prepare for binding of mRNA, column 4 is cleaned to regenerate its ability to bind mRNA, mRNA is eluted from column 5 into a product collection chamber, and column 6 is washed to remove impurities. FIG. 2B describes a second step in the multicolumn chromatography process in which the feed solution containing mRNA is added to column 2, breakthrough from column 2 is directed into column 3, column 4 is equilibrated to prepare for binding of mRNA, column 5 is cleaned to regenerate its ability to bind mRNA, and mRNA is eluted from column 6 into a product collection chamber.

FIG. 4A shows the percentage of mRNAs containing polyA tails. FIG. 4B shows the percentage of mRNAs that were of the expected length.

FIG. 6A shows how increasing the scale of an IVT reaction increases the amount of buffer required (squares), dT chromatography elution volume (triangles), and column internal diameter (ID, inverted triangles) required for mRNA purification. FIGS. 6B-6D shows how intensifying the dT chromatography process reduces the required column internal diameter (FIG. 6B), amount of buffer required (FIG. 6C), and volume required for elution of purified mRNA (FIG. 6D). Dotted lines indicate maximum column diameter (FIGS. 6A-6B) and/or maximum elution volume (FIGS. 6A and 6D) in process.

FIG. 7A shows the relationship between salt concentration and column static binding capacity (SBC), dynamic binding capacity (DBC), and the purity, in terms of mRNAs having poly(A) tails and expected lengths. FIGS. 7B-7C show the relationship between salt concentration and the solubility of mRNA following salt addition and incubation either overnight at 4° C. (FIG. 7B) or for 1 hour at 25° C. (FIG. 7C).

DETAILED DESCRIPTION

Figure 1:
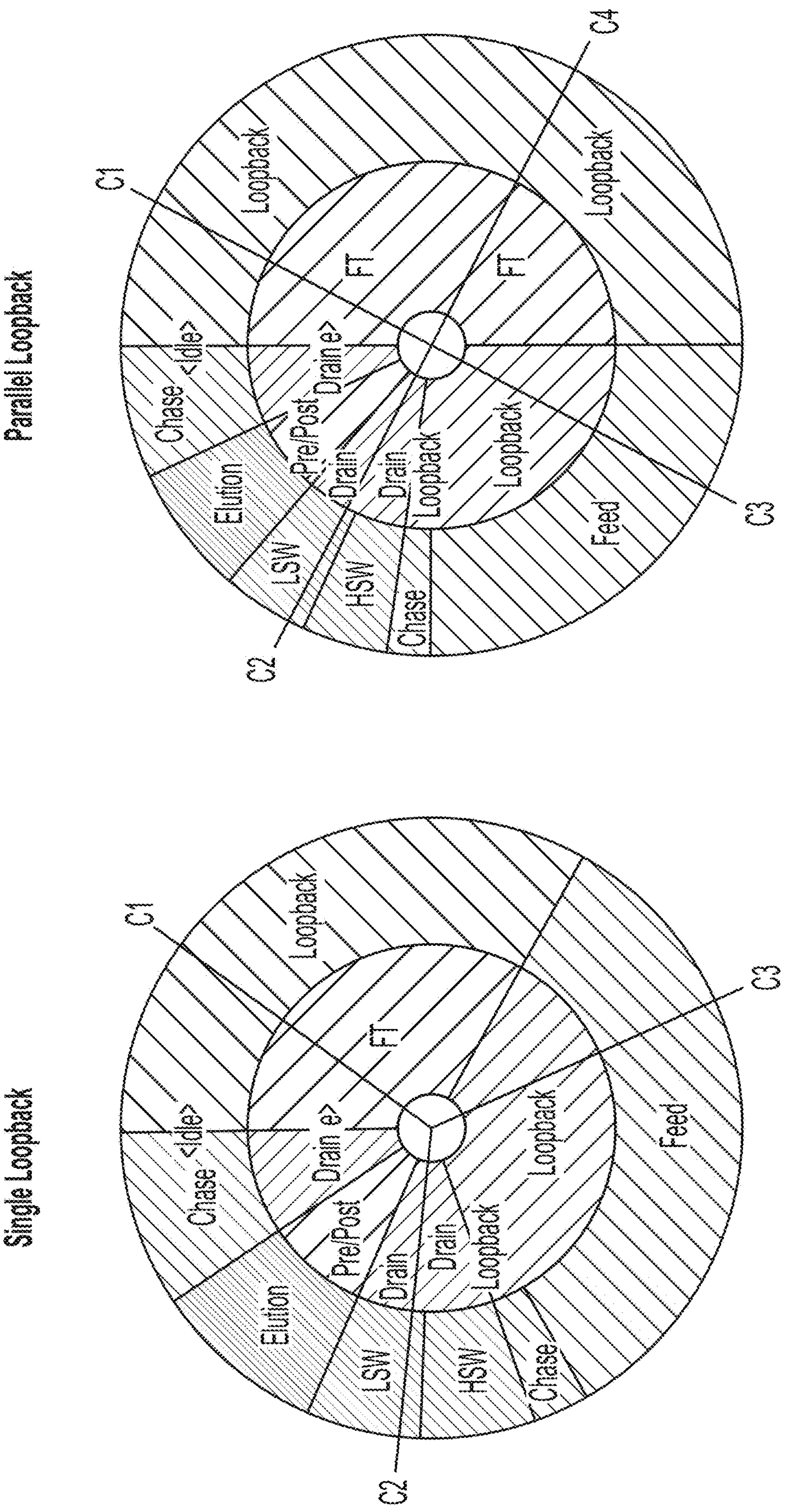
FIG. 1 shows a comparison of single loopback and a parallel loopback process. Outer circles refer to inputs to a column, while inner circles refer to where that input is directed after it leaves the column. HSW=high-salt wash; LSW=low-salt wash; FT=flowthrough.

The present disclosure relates to methods of purifying nucleic acids, such as mRNA, from an in vitro transcription (IVT) or in vitro capping reaction. mRNA can be produced by IVT, but the presence of IVT reaction components, including nucleotide triphosphates, DNA templates, DNases used to cleave DNA templates, and RNA polymerases, can catalyze degradation of the mRNA, inhibit encapsulation in lipid nanoparticles, and inhibit mRNA translation in vivo. Thus, mRNAs must be separated from IVT reaction components and other products, such as double-stranded RNAs (dsRNAs), before use in downstream applications, such as encapsulation in lipid nanoparticles and/or administration to subjects. Multicolumn chromatography utilizes multiple chromatography columns, which can be connected in series, to load nucleic acids (e.g., mRNAs), such that the flowthrough from one column can be directed onto the stationary phase of the next column in series. Nucleic acids in the flowthrough, or breakthrough, that are not captured by the stationary phase of the first column may be captured by the stationary phase of one or more secondary columns. By capturing breakthrough from the first column, the secondary column(s) prevents loss of nucleic acid without significant losses in process productivity. Thus, a larger amount of nucleic acid may be added to the first column without a risk of loss due to exceeding the dynamic binding capacity of the first column. Once the first column has been saturated with nucleic acid, the input solution containing nucleic acid may be applied directly to one of the secondary columns, while nucleic acid is eluted from the first column. Once bound nucleic acids have been eluted from the first column, the first column may be regenerated and equilibrated to restore its ability to capture more nucleic acids, such as those present in the flowthrough from the last column in the series of columns. With all columns in the set going through this cycle of 1) equilibration; 2) receiving flowthrough containing nucleic acid from a previous column in series, with this step optionally being repeated; 3) receiving feed solution containing concentrated nucleic acid; 4) washing to remove impurities; 5) elution to collect nucleic acid; and 6) regeneration to restore nucleic acid-binding capacity, the nucleic acid feed solution spends more time in the "mass transfer zone," in which nucleic acids are actively binding to the stationary phase rather than moving through stationary phase that is saturated with nucleic acids. In the idle zone of a chromatography column, resin is either already loaded with mRNA and awaiting a washing or elution step, or the resin is freshly regenerated and awaiting fresh nucleic acid load material. In the mass transfer zone, resin is either being actively loaded with nucleic acids, or resin previously loaded with nucleic acid is actively being washed, eluted, regenerated, or equilibrated. The idle zones are unproductive, and represent the majority of a column during traditional batch chromatography. With its simultaneous operation of multiple columns, multicolumn chromatography divides this productive mass transfer zone across several smaller columns, leading to far higher process productivities compared to traditional batch chromatography. Additionally, by processing smaller columns in parallel, rather than a single column as in traditional batch chromatography, the amount of idle time, in which the stationary phase is not interacting with any nucleic acid, is reduced. Thus, multicolumn chromatography has a greater productivity, in terms of nucleic acid that can be purified using a given amount of stationary phase in a given length of time, than batch chromatography methods. Furthermore, the flowthrough of one column may be divided and directed into multiple secondary columns in parallel, allowing more concentrated mRNA feed solutions to be applied to a primary column while minimizing the risk of overloading any of the secondary columns. Use of more concentrated feed solutions, and consequently the ability to purify more mRNA in a given amount of time, offsets the need for additional resin in parallel columns, thereby increasing the productivity of parallel multicolumn chromatography methods relative to batch chromatography methods.

Column Chromatography

Aspects of the present disclosure relate to methods of purifying nucleic acids using multicolumn chromatography. Multicolumn chromatography refers to a column chromatography method in which multiple columns are connected in series, such that liquid flowing out of one column can be directed into the next column in the series, if desired, or directed into a separate container, if not. Column chromatography, described in more detail below, separates components of a mixture by passing a mobile phase containing the mixture through a column containing a stationary phase. In some embodiments, the compositions to be purified are added to the top of the stationary phase of the column, and a mobile phase is added to dissolve the compositions. The mobile phase passes through the stationary phase of the column, and dissolved components of the mobile phase interact with the stationary phase of the column with different affinities. Components that interact weakly with the stationary phase migrate faster, reaching the bottom of the column sooner. By contrast, components that interact more strongly are retained in the column for longer. Because different components of a composition reach the bottom of the column at different times, they can be collected separately into distinct collection vessels, allowing for the collection of a desired component from a composition containing multiple components. In some embodiments, the mRNA composition is purified using reverse phase column chromatography. In reverse phase column chromatography, the stationary phase is non-polar, while the mobile phase is polar.

In some embodiments of chromatography methods, the chromatography columns are ionic exchange columns. Ionic exchange chromatography allows for the separation of ionizable molecules, such as nucleic acids and proteins, based on their net charge, which can be manipulated by changing the pH of a solution comprising one or more molecules to be separated. When a solution comprising one or more molecules to be separated is loaded onto a stationary phase of an ionic exchange column, molecules with a complementary charge to that of the stationary phase (e.g., negatively charged molecules in contact with a positively charged stationary phase) will be retained in the column, while molecules without a complementary charge will pass through the stationary phase. One or more mobile phases of different pHs can then be applied to the stationary phase to change the charge of retained molecules, such that a fraction containing a desired molecule, such as a nucleic acid, can be eluted from the column.

In some embodiments, the chromatography columns are affinity columns. Affinity columns comprise a stationary phase that has an affinity for a desired molecule. For example, proteins comprising an amino acid sequence of at least six consecutive histidine residues (e.g., a His-Tag) are readily bound by nickel ions on a stationary phase, allowing proteins containing the His-Tag to be retained while other proteins pass through the stationary phase. The column can then be washed to remove any residual impurities, followed by eluting the bound desired molecule by applying a solution that disrupts binding of the molecule to the stationary phase. Multiple stationary phases are suitable for purification of nucleic acids by affinity chromatography, including oligo-dT, poly(rI), and poly(rC), and nucleic acid probes comprising one or more nucleic acid sequences that are complementary to a nucleic acid sequence on the desired nucleic acid. See, e.g., Morales et al. *Bio-protocol.* 2013. 3(13): e808.

In some embodiments, the chromatography columns are hydrophobic interaction columns. Hydrophobic interaction chromatography allows for the separation of molecules based on their hydrophobicity. Typically, a high-salt solution comprising a desired molecule and one or more impurities is applied to a stationary phase, with the high salt content reducing solubility and promoting binding to the stationary phase. Then, one or more mobile phases with progressively lower salt concentrations are applied to the column, such that eluted fractions contain progressively more hydrophobic molecules.

In some embodiments, the chromatography columns are mixed mode chromatography columns. In mixed mode chromatography, multiple properties of a desired molecule, such as ionization status and solubility based on hydrophobicity, are used to separate the desired molecule from one or more impurities. A solution containing a desired molecule is applied to the stationary phase of the column to allow for binding of the desired molecule to the stationary phase, and one or more mobile phases are passed through the stationary phase to remove impurities. Each mobile phase may have a different ionic strength, pH, and/or salt concentration, to promote release of one or more impurities, but allow the desired molecule to remain bound to the stationary phase. After removal of impurities, an eluting solution with a desired ionic strength, pH, and salt concentration is applied to the stationary phase to promote release of the desired molecule from the stationary phase.

In some embodiments the chromatography columns are size exclusion chromatography columns. Size exclusion chromatography separates molecules based on their rate of filtration through a gel or other porous stationary phase, which is determined by their size. Smaller molecules, such as shorter proteins or nucleic acids, diffuse through pores of the gel and thus take longer to pass through the column, while larger molecules traverse the column more quickly, as they are not retained by pores of the gel.

In some embodiments, a chromatography column comprises a hollow fiber membrane. A hollow fiber membrane (HFM) refers to a hollow cylinder, with the walls of the cylinder comprising a fibrous membrane. The walls of the hollow fiber membrane may comprise a stationary phase, such as oligo-dT resin or beads, that allows for binding of a desired molecule, such as an mRNA. A solution containing the desired molecule may then be passed through the hollow center of the hollow fiber membrane, allowing the desired molecule to be retained, followed by one or more washing and/or eluting steps to separate the desired molecule from any impurities. In this manner, the walls of the membrane function as the stationary phase of the chromatography column, as an alternative to a particulate stationary phase that is packed into the interior space of a chromatography column. However, the empty space within the center of the hollow fiber membrane allows solutions to be passed through at greater pressures than are typically feasible with a packed chromatography column. Hollow fiber membranes may be used as an alternative to a stationary phase packed into the interior of the chromatography column, or the interior of a hollow fiber membrane may be packed with a particulate stationary phase, such as resin or beads, allowing both the packed stationary phase and the walls of the membrane to retain a desired molecule. Hollow fiber membranes may comprise one or more stationary phases described herein, such as a stationary phase of an ionic exchange chromatography column, an affinity chromatography column, a mixed mode chromatography column, or a reverse phase chromatography column. In some embodiments, each hollow fiber membrane comprises oligo-dT.

In some embodiments, one or more chromatography columns are replaced with one or more sheet membranes comprising stationary phases. In contrast to cylindrical hollow fiber membranes, which contain a hollow center through which a solution is passed, a solution is applied to one side of a sheet, and exits the other side after passing through one or more sheets. In some embodiments, a sheet membrane comprises a single flat sheet. In some embodiments, a sheet membrane comprises a sheet wound into a spiral. In some embodiments, a sheet membrane comprises multiple sheets that take the place of a single chromatography column, with a solution being applied to a first sheet in the stack, and the solution exiting the stack after passing through each sheet. Sheet membranes may comprise one or more stationary phases described herein, such as a stationary phase of an ionic exchange chromatography column, an affinity chromatography column, a mixed mode chromatography column, or a reverse phase chromatography column. In some embodiments, each sheet membrane comprises oligo-dT.

In some embodiments, the stationary phase of a column and/or membrane comprises oligo-dT reverse phase media (e.g., resin or beads). In some embodiments, the particles, resin, and/or beads of the stationary phase comprise oligo-dT. In some embodiments, the hollow fiber membrane of a column comprise oligo-dT. Oligo-dT refers to a DNA oligonucleotide comprising multiple repeated thymidine bases. This sequence of repeated thymidine bases bind to the polyA tail of mRNAs. Immobilization of oligo-dT by bonding (e.g., covalent bonding) to particles of the stationary phase promotes binding of mRNAs to the stationary phase. In some embodiments, one or more mRNAs of the mRNA composition bind to the stationary phase and migrate through the column slower than other components. In some embodiments, the column retains one or more mRNAs of the mRNA composition while impurities are removed. In some embodiments, the impurities are removed by adding another mobile phase (e.g., a washing solution) to the column, with the passage of the washing solution carrying impurities through the column while mRNA remains bound to the stationary phase. In some embodiments, after impurities are removed from the column, another mobile phase (e.g., an elution buffer) is added to the column to elute one or more mRNAs from the column. In some embodiments, after one or more mRNAs are eluted from the column, a cleaning solution is passed through the column to regenerate the capacity of the column to bind mRNA. In some embodiments, after the column is regenerated, an equilibration solution is passed through the column to remove residual cleaning solution and to prepare the column to bind mRNA.

The pH of the mobile phase can vary. In some embodiments, the pH of the mobile phase is between about pH 5.0 and pH 9.5 (e.g., about 5.0, about 5.5, about 6.0, about 6.5, about 7.0, about 7.5, about 8.0, about 8.5, about 9.0, or about 9.5). In some embodiments, the pH of the mobile phase is between about pH 6.8 and pH 8.5 (e.g., about 6.8, about 7.0, about 7.2, about 7.4, about 7.6, about 7.8, about 8.0, about 8.3, or about 8.5). In some embodiments, the pH of the mobile phase is about 7.0.

The particle size (e.g., as measured by the diameter of the particle) of a stationary phase of a column can vary. In some embodiments, the particle size of the stationary phase ranges from about 1 μm to about 100 μm (e.g., any value between 1 and 100, inclusive) in diameter. In some embodiments, the particle size of the column stationary phase ranges from about 2 μm to about 10 μm, about 2 μm to about 6 μm, or about 4 μm in diameter. The pore size of particles (e.g., as measured by the diameter of the pore) can also vary. In some embodiments, the particles comprise pores having a diameter of about 500 Å to about 5000 Å, about 800 Å to about 3000 Å, or about 1000 to about 2000 Å. In some embodiments, the particles comprise pores having a diameter of about 100 Å to about 10,000 Å. In some embodiments, the particles comprise pores having a diameter of about 100 Å to about 5000 Å, about 100 Å to about 1000 Å, or about 1000 Å to about 2000 Å. In some embodiments, the stationary phase comprises polystyrene divinylbenzene. In some embodiments, the stationary phase comprises oligo-dT reverse phase media (e.g., resin or beads).

The temperature of the column (e.g., the stationary phase within the column during purification) can vary. In some embodiments, the column has a temperature from about 4° C. to about 99° C. (e.g., any temperature between 4° C. and 99° C.). In some embodiments, the column has a temperature from about 4° C. to about 40° C. (e.g., any temperature between 4° C. and 40° C., for example about 4° C., about 10° C., about 20° C., about 25° C., about 30° C., about 35° C., or about 40° C.). In some embodiments, the column has a temperature from about 20° C. to about 40° C. (e.g., any temperature between 20° C. and 40° C.). In some embodiments, the column has a temperature of about 30° C. In some embodiments, the binding of the RNA to the oligo-dT resin occurs at a temperature of lower than 40° C. In some embodiments, the binding of the RNA to the oligo-dT resin occurs at a temperature of 4° C. to 30° C., 4° C. to 25° C., 4° C. to 20° C., 4° C. to 15° C., 4° C. to 10° C., 4° C. to 8° C., 10° C. to 30° C., 10° C. to 25° C., 10° C. to 20° C., 10° C. to 15° C., or 15° C. to 25° C.

In some embodiments of purification methods, the mobile phase comprises Tris and/or chelator, such as EDTA (e.g., Tris-EDTA, also referred to as TAE). As used herein, a "mobile phase" is an aqueous solution comprising water and/or one or more organic solvents used to carry an analyte (or analytes), such as a nucleic acid or mixture of nucleic acids through a column. In some embodiments, a mobile phase comprises a polar organic solvent. Examples of polar organic solvents suitable for inclusion in a mobile phase include but are not limited to alcohols, ketones, nitrates, esters, amides and alkylsulfoxides. In some embodiments, a mobile phase comprises one or more organic solvents selected from the group consisting of acetonitrile, methanol, ethanol, propanol, isopropanol, dimethylformamide, methyl acetate, acetone, and dimethyl sulfoxide (DMSO), hexaline glycol, polar aprotic solvents (including, e.g., tetrahydrofuran (THF), dimethyl sulfoxide (DMSO), dimethylformamide (DMF), acetonitrile, acetone, etc.), $C_{1-4}$ alkanols, $C_{1-6}$ alkandiols, and $C_{2-4}$ alkanoic acids. The concentration of organic solvent in a mobile phase can vary. For example, in some embodiments, the volume percentage (v/v) of an organic solvent in a mobile phase varies from 0% (absent) to about 100% of a mobile phase. In some embodiments, the volume percentage of organic solvent in a mobile phase is between about 5% and about 75% v/v. In some embodiments, the volume percentage of organic solvent in a mobile phase is between about 25% and about 60% v/v. In some embodiments, the concentration of organic solvent in a mobile phase is about 5%, about 10%, about 15%, about 20%, about 25%, about 30%, about 35%, about 40%, about 45%, about 50%, about 55%, about 60%, about 65%, about 70%, about 75%, about 80%, about 85%, or about 90% v/v. In some embodiments, a mobile phase comprises acetonitrile. In some embodiments, a mobile phase comprises additional components, for example as described in U.S. Patent Publication US 2005/0011836, the entire contents of which are incorporated herein by reference.

In some embodiments, one or more solvent solutions (e.g., 1, 2, 3, 4, 5, or more) of the mobile phase comprise a combination of at least two ion pairing agents (e.g., 2, 3, 4, 5, or more). As used herein, an "ion pairing agent" or an "ion pair" refers to an agent (e.g., a small molecule) that functions as a counter ion to a charged (e.g., ionized or ionizable) functional group on an HPLC analyte (e.g., a nucleic acid) and thereby changes the retention time of the analyte as it moves through the stationary phase of an HPLC column. Generally, ion paring agents are classified as cationic ion pairing agents (which interact with negatively charged functional groups) or anionic ion pairing agents (which interact with positively charged functional groups). The terms "ion pairing agent" and "ion pair" further encompass an associated counter-ion (e.g., acetate, phosphate, bicarbonate, bromide, chloride, citrate, nitrate, nitrite, oxide, sulfate and the like, for cationic ion pairing agents, and sodium, calcium, and the like, for anionic ion pairing agents). In some embodiments, one or more ion pairing agents utilized in the methods described by the disclosure is a cationic ion pairing agent. Examples of cationic ion pairing agents include but are not limited to certain protonated or quaternary amines (including e.g., primary, secondary and tertiary amines) and salts thereof, such as a trietheylammonium salt (e.g., triethylammonium acetate (TEAA)), a tributylammonium salt (e.g., tetrabutylammonium phosphate (TBAP) or tetrabutylammonium chloride (TBAC)), a hexylammonium salt (e.g., hexylammonium acetate (HAA)), a dibutylammonium salt (e.g., dibutylammonium acetate (DBAA)), a tetrapropylammonium salt (e.g., tetrapropylammonium bromide (TPAB)), a dodecyltrimethylammonium salt (e.g., dodecyltrimethylammonium chloride (DTMAC)), or a tetra(decyl)ammonium salt (e.g., tetra(decyl)ammonium bromide (TDAB)), a dihexylammonium salt (e.g., dihexylammonium acetate (DHAA)), a dipropylammonium salt (e.g., dipropylammonium acetate (DPAA)), a myristyltrimethylammonium salt (e.g., myristyltrimethylammonium bromide (MTEAB)), a tetraethylammonium salt (e.g., tetraethylammonium bromide (TEAB)), a tetraheptylammonium salt (e.g., tetraheptylammonium bromide (THepAB)), a tetrahexylammonium salt (e.g., tetrahexylammonium bromide (THexAB)), a tetrakis(decyl)ammonium salt (e.g., tetrakis(decyl)ammonium bromide (TrDAB)), a tetramethylammonium salt (e.g., tetramethylammonium bromide (TMAB)), a tetraoctylammonium salt (e.g., tetraoctylammonium bromide (TOAB)), or a tetrapentylammonium salt (e.g., tetrapentylammonium bromide (TPeAB)). In some embodiments, one or more solvent solutions of the mobile phase comprise a combination of two or more ion pairing agents selected from the group consisting of a trietheylammonium salt, tributylammonium salt, hexylammonium salt, dibutylammonium salt, tetrapropylammonium salt, dodecyltrimethylammonium salt, tetra(decyl)ammonium salt, dihexylammonium salt, dipropylammonium salt, myristyltrimethylammonium salt, tetraethylammonium salt, tetraheptylammonium salt, tetrahexylammonium salt, tetrakis(decyl)ammonium salt, tetramethylammonium salt, tetraoctylammonium salt, and tetrapentylammonium salt. In some embodiments, one or more solvent solutions of the mobile phase comprise a combination of two or more ion pairing agents selected from the group consisting of HAA, TBAP, TPAB, TBAC, DBAA, TEAA, DTMAC, TDAB, DHAA, DPAA MTEAB, TEAB, THepAB, THexAB, TrDAB, TMAB, TOAB, and TPeAB. In some embodiments, one or more solvent solutions of the mobile phase comprise a combination of (i) TPAB and TBAC, (ii) DBAA and TEAA, or (iii) TBAP and TEAA. In some embodiments, one or more solvent solutions of the mobile phase comprise a combination of TPAB and TBAC.

In some embodiments, one or more solvent solutions (e.g., 1, 2, 3, 4, 5, or more) of the mobile phase comprise a single ion pairing agent. In some embodiments, one or more ion pairing agents utilized in the methods described by the disclosure is a cationic ion pairing agent. In some embodiments, the ion pairing agent is a cationic ion pairing agent. In some embodiments, one or more solvent solutions of the mobile phase comprise a salt selected from the group consisting of a trietheylammonium salt, tributylammonium salt, hexylammonium salt, dibutylammonium salt, tetrapropylammonium salt, dodecyltrimethylammonium salt, tetra (decyl)ammonium salt, dihexylammonium salt, dipropylammonium salt, myristyltrimethylammonium salt, tetraethylammonium salt, tetraheptylammonium salt, tetrahexylammonium salt, tetrakis(decyl)ammonium salt, tetramethylammonium salt, tetraoctylammonium salt, and tetrapentylammonium salt. In some embodiments, one or more solvent solutions of the mobile phase comprise HAA, TBAP, TPAB, TBAC, DBAA, TEAA, DTMAC, TDAB, DHAA, DPAA MTEAB, TEAB, THepAB, THexAB, TrDAB, TMAB, TOAB, TPeABHAA, TBAP, TPAB, TBAC, DBAA, TEAA, DTMAC, or TDAB. In some embodiments, each of one or more solvents of the mobile phase comprises one ion pairing agent. In some embodiments, each of one or more solvents of the mobile phase comprises the same ion pairing agent. In some embodiments, each of one or more solvents of the mobile phase comprises a salt selected from the group consisting of a trietheylammonium salt, tributylammonium salt, hexylammonium salt, dibutylammonium salt, tetrapropylammonium salt, dodecyltrimethylammonium salt, tetra(decyl)ammonium salt, dihexylammonium salt, dipropylammonium salt, myristyltrimethylammonium salt, tetraethylammonium salt, tetraheptylammonium salt, tetrahexylammonium salt, tetrakis(decyl)ammonium salt, tetramethylammonium salt, tetraoctylammonium salt, and tetrapentylammonium salt. In some embodiments, each of one or more solvents of the mobile phase comprises HAA, TBAP, TPAB, TBAC, DBAA, TEAA, DTMAC, TDAB, DHAA, DPAA MTEAB, TEAB, THepAB, THexAB, TrDAB, TMAB, TOAB, TPeABHAA, TBAP, TPAB, TBAC, DBAA, TEAA, DTMAC, or TDAB. A salt of a cation, as used herein, refers to a composition comprising the cation and an anionic counter ion. For example, a "tetrabutylammonium salt" may refer to tetrabutylammonium phosphate, tetrabutylammonium chloride, tetrabutylammonium bromide, tetrabutylammonium phosphate, or another composition comprising the cation tetrabutylammonium and an anionic counter ion. In some embodiments, the ion pairing agent comprises a cation and an anionic counter ion, wherein the cation is selected from the group consisting of trietheylammonium, tributylammonium, hexylammonium, dibutylammonium, tetrapropylammonium, dodecyltrimethylammonium, tetra(decyl)ammonium, dihexylammonium, dipropylammonium, myristyltrimethylammonium, tetraethylammonium, tetraheptylammonium, tetrahexylammonium, tetrakis(decyl)ammonium, tetramethylammonium, tetraoctylammonium, and tetrapentylammonium, and the anionic counter ion is selected from the group consisting of a bromide, chloride, phosphate, and acetate.

Protonated and quaternary amine ion pairing agents can be represented by the following formula:

$$R_4N^{\oplus}A^{\ominus}$$

wherein each R independently is hydrogen, optionally substituted aliphatic, optionally substituted heteroaliphatic, optionally substituted aryl or optionally substituted heteroaryl; provided that at least one instance of R is not hydrogen; and A is an anionic counter ion. The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups. The term "aryl" refers to a radical of a monocyclic or polycyclic (e.g., bicyclic or tricyclic) 4n+2 aromatic ring system (e.g., having 6, 10, or 14 $\pi$ electrons shared in a cyclic array) having 6-14 ring carbon atoms and zero heteroatoms provided in the aromatic ring system ("C6-14 aryl"). The term "heteroaryl" refers to a radical of a 5-14 membered monocyclic or polycyclic (e.g., bicyclic, tricyclic) 4n+2 aromatic ring system (e.g., having 6, 10, or 14 $\pi$ electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). Suitable anionic counter ions include, but are not limited to, acetate, trifluoroacetate, phosphate, chloride, bromide hexafluorophosphate, sulfate, methylsulfonate, trifluoromethylsulfonate, 1,1,1,3,3,3-hexafluoro-2-propanol (HFIP), 1,1,1,3,3,3-hexafluoro-2-methyl-2-propanol (HFMIP) and the like.

The term "optionally substituted" refers to being substituted or unsubstituted. In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction.

In some embodiments, a solvent solution of the mobile phase (e.g., a first solvent solution or a second solvent solution) comprising at least two ion pairing agents are in a molar ratio of between about 1:1,000 to about 1,000:1, such that the nucleic acids and if present, lipids, traverse the column at different rates. In some embodiments, the at least two ion pairing agents are in a molar ratio between about 1:1,000 to about 1,000:1, 1:900 to about 900:1, 1:800 to about 800:1, 1:700 to about 700:1, 1:600 to about 600:1, 1:500 to about 500:1, 1:400 to about 400:1, about 1:300 to about 300:1, about 1:200 to about 200:1, about 1:100 to about 100:1, about 50:1 to about 1:50, about 40:1 to about 1:40, about 30:1 to about 1:30, about 20:1 to about 1:20, or about 10:1 to about 1:10. In some embodiments, each solvent solution comprises at least two ion pairing agents in a molar ratio of between about 1:100 to about 100:1. In some embodiments, the at least two ion pairing agents are in a molar ratio between about 1:100 to about 100:1, 1:90 to about 90:1, 1:80 to about 80:1, 1:70 to about 70:1, 1:60 to about 60:1, 1:50 to about 50:1, 1:40 to about 40:1, about 1:30 to about 30:1, about 1:20 to about 20:1, about 1:10 to about 10:1, about 5:1 to about 1:5, about 4:1 to about 1:4, about 3:1 to about 1:3, or about 2:1 to about 1:2. In some embodiments, the at least two ion pairing agents are in a 1:1 molar ratio.

In some embodiments, a solvent solution of the mobile phase (e.g., a first solvent solution or a second solvent solution) comprises at least two ion pairing agents that are in a molar ratio of between about 1:6 to about 6:1, such that the nucleic acids and if present, lipids, traverse the column at different rates. In some embodiments, each solvent solution comprises at least two ion pairing agents in a molar ratio of between about 1:4 to about 4:1. In some embodiments, the at least two ion pairing agents are in a molar ratio between about 1:3 to about 3:1, about 1:2 to about 2:1, or about 1:1.5 to about 1.5:1. In some embodiments, the at least two ion pairing agents are in a 1:1 molar ratio.

The concentration of each ion pairing agent in a solvent solution (e.g., a first solvent solution or a second solvent solution) may range from about 1 mM to about 25 M (e.g., about 1 mM, about 2 mM, about 5 mM, about 10 mM, about 50 mM, about 100 mM, about 200 mM, about 500 mM, about 1 M, about 1.2 M, about 1.5 M, about 1.75 M, about 2M, about 2.25 M, about 2.5 M, about 2.75 M, about 3 M, about 3.25 M, about 3.5 M, about 3.75 M, about 4 M, about 4.25 M, about 4.5 M, about 4.75 M, about 5 M, about 5.5 M, about 6 M, about 6.5 M, about 7 M, about 7.5 M, about 8 M, about 8.5 M, about 9 M, about 9.5 M, about 10 M, about 11 M, about 12 M, about 13 M, about 14 M, about 15 M, about 16 M, about 17 M, about 18 M, about 19 M, or about 20 M), inclusive. In some embodiments, the concentration of an ion pairing agent in a mobile phase (e.g., a first solvent solution or a second solvent solution) ranges from about, 10 mM-20 M, 20 mM-15 M, 30 mM-12 M, 40 mM-10 M, 50 mM-8 M, 75 mM-5 M, 100 mM-2.5 M, 125 mM-2 M, 150 mM-1.5 M, 175 mM-1 M, or 200 mM-500 mM. In some embodiments, the concentration of each of the ion pairing agents independently ranges from about, 10 mM-20 M, 20 mM-15 M, 30 mM-12 M, 40 mM-10 M, 50 mM-8 M, 75 mM-5 M, 100 mM-2.5 M, 125 mM-2 M, 150 mM-1.5 M, 175 mM-1 M, or 200 mM-500 mM. In some embodiments, a first or second solvent solution comprises a single ion pairing agent, which is present in an amount from about, 10 mM-20 M, 20 mM-15 M, 30 mM-12 M, 40 mM-10 M, 50 mM-8 M, 75 mM-5 M, 100 mM-2.5 M, 125 mM-2 M, 150 mM-1.5 M, 175 mM-1 M, or 200 mM-500 mM.

The concentration of each ion pairing agent in a solvent solution (e.g., a first solvent solution or a second solvent solution) may range from about 1 mM to about 2 M (e.g., about 1 mM, about 2 mM, about 5 mM, about 10 mM, about 50 mM, about 100 mM, about 200 mM, about 500 mM, about 1 M, about 1.2 M, about 1.5 M, or about 2M), inclusive. In some embodiments, the concentration of an ion pairing agent in a mobile phase (e.g., a first solvent solution or a second solvent solution) ranges from about, 10 mM-1M, 40 mM-300 mM, 50 mM-500 mM, 75 mM-400 mM, 100 mM-300 mM, 200-300 mM, 200-250 mM, or 250-300 mM. In some embodiments, the concentration of each of the ion pairing agents independently ranges from about, 10 mM-1M, 40 mM-300 mM, 50 mM-500 mM, 75 mM-400 mM, 100 mM-300 mM, 200-300 mM, 200-250 mM, or 250-300 mM. In some embodiments, two ion pairing agents are present at concentrations of about 20 mM: 40 mM, 50 mM: 50 mM, 50 mM: 60 mM, 50 mM: 75 mM, 50 mM: 100 mM, 50 mM:150 mM, 100 mM: 100 mM, 100 mM: 125 mM, 100 mM: 150 mM, 100 mM: 175 mM, 100 mM: 200 mM, 100 mM: 200 mM, 100 mM: 250 mM, 100 mM: 300 mM, 125 mM: 125 mM, 125 mM: 150 mM, 125 mM: 175 mM, 125 mM: 200 mM, 125 mM: 250 mM, 125 mM: 300 mM, 150 mM: 175 mM, 150 mM: 200 mM, 150 mM: 250 mM, 150 mM: 300 mM, 200 mM: 200 mM, 200 mM: 250 mM, 200 mM: 300 mM, 250 mM: 250 mM, 250 mM: 300 mM, or 300 mM: 300 mM.

Examples of ion pairing agent concentrations include but are not limited to 40 mM TEAA: 20 mM DBAA, 100 mM TEAA: 50 mM DBAA, 50 mM TBAP: 50 mM TEAA, 250 mM TBAP: 250 mM TEAA, 300 mM TBAP: 300 mM TEAA, 50 mM TBAP: 150 mM TEAA, 125 mM TBAP: 250 mM TEAA, 250 mM TBAP: 250 mM TEAA, 300 mM TBAP: 300 mM TEAA, 50 mM DBAA: 50 mM TEAA, 60 mM DBAA: 50 mM TEAA, 75 mM DBAA: 50 mM TEAA, 175 mM DBAA: 125 mM TEAA, 100 mM DBAA: 100 mM TEAA, 50 mM TBAP: 100 mM TEAA, 100 mM TBAP: 200 mM TEAA, 125 mM TBAP: 250 mM TEAA, 150 mM TABP: 200 mM TEAA, 150 mM TBAP: 200 mM TEAA, 150 mM TBAP: 250 mM TEAA, 50 mM TBAP: 150 mM TEAA, 100 mM TBAP: 150 mM TEAA, 250 mM TBAP: 200 mM TEAA, 250 mM TBAP: 250 mM TEAA, or 200 mM TBAP: 300 mM TEAA. In some embodiments, one or more solvent solutions of the mobile phase comprise a combination of TPAB and TBAC. In some embodiments, the concentrations of TPAB and TBAC independently range from 50 mM-300 mM. In some embodiments, one or more solvent solutions of the mobile phase comprise 200 mM TPAB: 200 mM TBAC, 250 mM TPAB: 250 mM TBAC, or 300 mM TPAB: 300 mM TBAC. In some embodiments, one or more solvent solutions of the mobile phase comprise 250 mM TPAB: 250 mM TBAC.

Ion pairing agents are generally dispersed within a mobile phase. As used herein, a "mobile phase" is an aqueous solution comprising water and/or one or more organic solvents used to carry an HPLC analyte (or analytes), such as a nucleic acid encapsulated in a lipid nanoparticle, mixture of nucleic acids in lipid nanoparticles, or a pharmaceutical composition comprising a nucleic acid or mixture of nucleic acids in lipid nanoparticles, through an HPLC column. In some embodiments, a mobile phase for use in HPLC methods as described by the disclosure is comprised of multiple (e.g., 2, 3, 4, 5, or more) solvent solutions. In some embodiments of the HPLC methods described by the disclosure, the mobile phase comprises two solvent solutions, a first solvent solution and a second solvent solution (e.g., Mobile Phase A, and Mobile Phase B). In some embodiments, a solvent solution comprises at least two ion pairing agents in a molar ratio of 1:1,000 to 1,000:1. In some embodiments, each solvent solution (e.g., the first solvent solution and the second solvent solution) comprises at least two ion pairing agents in a molar ratio of 1:1,000 to 1,000:1. In some embodiments, a solvent solution comprises at least two ion pairing agents in a molar ratio of 1:100 to 100:1. In some embodiments, each solvent solution (e.g., the first solvent solution and the second solvent solution) comprises at least two ion pairing agents in a molar ratio of 1:100 to 100:1. In some embodiments, a solvent solution comprises at least two ion pairing agents in a molar ratio of 1:75 to 75:1. In some embodiments, each solvent solution (e.g., the first solvent solution and the second solvent solution) comprises at least two ion pairing agents in a molar ratio of 1:75 to 75:1. In some embodiments, a solvent solution comprises at least two ion pairing agents in a molar ratio of 1:50 to 50:1. In some embodiments, each solvent solution (e.g., the first solvent solution and the second solvent solution) comprises at least two ion pairing agents in a molar ratio of 1:50 to 50:1. In some embodiments, a solvent solution comprises at least two ion pairing agents in a molar ratio of 1:25 to 25:1. In some embodiments, each solvent solution (e.g., the first solvent solution and the second solvent solution) comprises at least two ion pairing agents in a molar ratio of 1:25 to 25:1. In some embodiments, a solvent solution comprises at least two ion pairing agents in a molar ratio of 1:10 to 10:1. In some embodiments, each solvent solution (e.g., the first solvent solution and the second solvent solution) comprises at least two ion pairing agents in a molar ratio of 1:10 to 10:1. In some embodiments, a solvent solution comprises at least two ion pairing agents in a molar ratio of 1:6 to 6:1. In some embodiments, each solvent solution (e.g., the first solvent solution and the second solvent solution) comprises at least two ion pairing agents in a molar ratio of 1:6 to 6:1. In some embodiments, a solvent solution comprises at least two ion pairing agents in a molar ratio of 1:4 to 4:1. In some embodiments, each solvent solution (e.g., the first solvent solution and the second solvent solution) comprises at least two ion pairing agents in a molar ratio of 1:4 to 4:1.

In some embodiments, at least one solvent solution of the mobile phase comprises an organic solvent. Generally, an IP-RP HPLC mobile phase comprises a polar organic solvent. Examples of polar organic solvents suitable for inclusion in a mobile phase include but are not limited to alcohols, ketones, nitrates, esters, amides and alkylsulfoxides. In some embodiments, the mobile phase (e.g., at least one solvent solution of the mobile phase) comprises one or more organic solvents selected from the group consisting of polar aprotic solvents, $C_{1-4}$ alkanols, $C_{1-6}$ alkanediols, and $C_{2-4}$ alkanoic acids. In some embodiments, the mobile phase (e.g., at least one solvent solution of the mobile phase) comprises one or more organic solvents selected form the group consisting of acetone, acetonitrile, dimethylformamide, dimethylsulfoxide (DMSO), ethanol, hexylene glycol, isopropanol, methanol, methyl acetate, propanol, and tetrahydrofuran. In some embodiments, the mobile phase (e.g., at least one solvent solution of the mobile phase) comprises acetonitrile. In some embodiments, a mobile phase (e.g., at least one solvent solution of the mobile phase) comprises additional components, for example as described in U.S. Patent Publication US 2005/0011836, the entire contents of which is incorporated herein by reference.

The concentration of organic solvent in a mobile phase (e.g., each solvent solution of the mobile phase) can vary. For example, in some embodiments, the volume percentage (v/v) of an organic solvent in a mobile phase varies from 0% (absent) to about 100% of a mobile phase. In some embodiments, the volume percentage of organic solvent in a mobile phase (e.g., at least one solvent solution of the mobile phase) is between about 5% and about 75% v/v. In some embodiments, the volume percentage of organic solvent in a mobile phase (e.g., at least one solvent solution of the mobile phase) is between about 25% and about 60% v/v. In some embodiments, the volume percentage of organic solvent in a mobile phase (e.g., at least one solvent solution of the mobile phase) is at least about 50% v/v. In some embodiments, the volume percentage of organic solvent in a mobile phase (e.g., at least one solvent solution of the mobile phase) is about 50% to about 95%, about 55% to about 90%, about 60% to about 85%, about 65% to about 80%, or about 70% v/v to about 75% v/v. In some embodiments, the concentration of organic solvent in a mobile phase (e.g., at least one solvent solution of the mobile phase) is about 5%, about 10%, about 15%, about 20%, about 25%, about 30%, about 35%, about 40%, about 45%, about 50%, about 55%, about 60%, about 65%, about 70%, about 75%, about 80%, about 85%, about 90% v/v, or about 95% v/v.

In some embodiments, the first solvent solution does not comprise an organic solvent. In some embodiments, the volume percentage of organic solvent in the second solvent solution is at least about 50% v/v. In some embodiments, the volume percentage of organic solvent in the second solvent solution is about 50% to about 95%, about 55% to about 90%, about 60% to about 85%, about 65% to about 80%, or about 70% v/v to about 75% v/v. In some embodiments, the volume percentage of organic solvent in the second solvent solution is about 50%, about 55%, about 60%, about 65%, about 70%, about 75%, about 80%, about 85%, about 90% v/v, or about 95% v/v.

The pH of the mobile phase (e.g., the pH of each solvent solution of the mobile phase) can vary. In some embodiments, the pH of the mobile phase is between about pH 5.0 and pH 9.5 (e.g., about 5.0, about 5.5, about 6.0, about 6.5, about 7.0, about 7.5, about 8.0, about 8.5, about 9.0, or about 9.5). In some embodiments, the pH of the mobile phase is between about pH 6.8 and pH 9.0 (e.g., about 6.8, about 7.0, about 7.2, about 7.4, about 7.6, about 7.8, about 8.0, about 8.3, about 8.5, or about 9.0). In some embodiments, the pH of the mobile phase is about 8.0.

In some embodiments, the pH of the first solvent solution is between about pH 5.0 and pH 9.5 (e.g., about 5.0, about 5.5, about 6.0, about 6.5, about 7.0, about 7.5, about 8.0, about 8.5, about 9.0, or about 9.5). In some embodiments, the pH of the first solvent solution is between about pH 6.8 and pH 9.0 (e.g., about 6.8, about 7.0, about 7.2, about 7.4, about 7.6, about 7.8, about 8.0, about 8.3, about 8.5, or about 9.0). In some embodiments, the pH of the first solvent solution is about 8.0.

In some embodiments, the pH of the second solvent solution is between about pH 5.0 and pH 9.5 (e.g., about 5.0, about 5.5, about 6.0, about 6.5, about 7.0, about 7.5, about 8.0, about 8.5, about 9.0, or about 9.5). In some embodiments, the pH of the second solvent solution is between about pH 6.8 and pH 9.0 (e.g., about 6.8, about 7.0, about 7.2, about 7.4, about 7.6, about 7.8, about 8.0, about 8.3, or about 8.5). In some embodiments, the pH of the second solvent solution is about 8.0.

The concentration of two or more solvent solutions in a mobile phase can vary. For example, in a mobile phase comprising two solvent solutions (e.g., a first solvent solution and a second solvent solution), the volume percentage of the first solvent solution may range from about 0% (absent) to about 100%. In some embodiments, the volume percentage of the first solvent solution may range from about 5%, about 10%, about 15%, about 20%, about 25%, about 30%, about 35%, about 40%, about 45%, about 50%, about 55%, about 60%, about 65%, about 70%, about 75%, about 80%, about 85%, or about 90% v/v.

Conversely, in some embodiments, the volume percentage of the second solvent solution of a mobile phase may range from about 5%, about 10%, about 15%, about 20%, about 25%, about 30%, about 35%, about 40%, about 45%, about 50%, about 55%, about 60%, about 65%, about 70%, about 75%, about 80%, about 85%, or about 90% v/v.

In some embodiments, the ratio of the first solvent solution to the second solvent solution is held constant (e.g., isocratic) during elution of the nucleic acid. However, the skilled artisan will appreciate that in other embodiments, the relative ratio of the first solvent solution to the second solvent solution can vary throughout the elution step. For example, in some embodiments, the ratio of the first solvent solution is increased relative to the second solvent solution during the elution step. In some embodiments, the ratio of the first solvent solution is decreased relative to the second solvent solution during the elution step.

The concentration of one or more ion pairing agents in a mobile phase (e.g., a solvent solution) can vary. The relative ratios of the at least two ion pairing agents in a mobile phase (or solvent solution) may vary or be held constant (e.g., isocratic) during the eluting step. In some embodiments, the ratio of a first ion pairing agent is increased relative to a second ion pairing agent during the elution step. In some embodiments, the ratio of a first ion pairing agent is increased relative to a second ion pairing agent during the elution step. For example, in some embodiments, the ratio of TPAB to TBAC ranges from about 4:1 to about 1:4, about 3:1 to about 1:3, about 2:1 to about 1:2, or about 1:1 to 1:3.

The mobile phase (e.g., a solvent solution) may be gradient or isocratic with respect to the concentration of one or more organic solvents.

Multicolumn Chromatography

Aspects of the disclosure methods of purifying nucleic acids using multicolumn chromatography. Multicolumn chromatography refers to a column chromatography method in which multiple columns are capable of being connected in series, such that liquid flowing out of one column can be directed into one or more next columns in the set, if desired, or directed into a separate container, if not. Some aspects relate to methods of purifying a nucleic acid using at least three chromatography columns capable of being used in series, the method comprising:

(i)(a) loading a first chromatography column by contacting a first stationary phase of the first chromatography column with a feed solution comprising one or more nucleic acids, optionally wherein the one or more nucleic acids are mRNAs;

(ii)(a) loading a second chromatography column by contacting, in series with the first chromatography column, a second stationary phase of the second chromatography column with a portion of the feed solution that has contacted the first stationary phase of the first chromatography column; and (iv)(a) eluting the one or more nucleic acids from the first chromatography column. In some embodiments, a last chromatography column in a set of chromatography columns is capable of being used in series with the first chromatography column. "Loading" a column refers to adding a solution containing a desired molecule, such as a nucleic acid (e.g., mRNA), to the stationary phase of the column, whereby the solution traverses the stationary phase of the column, allowing the molecule to bind to the stationary phase. In some embodiments, a column is loaded by adding feed solution directly from a storage vessel, such as a vessel in which IVT was used to produce mRNAs. In some embodiments, a second column in series is loaded by adding output of the first column in series onto the stationary phase of the second column in series. Unless otherwise clear from context, "input" of a column refers to material, such as nucleic acids and/or mobile phases, that is added to the stationary phase of a column. Unless otherwise clear from context, "output" of a column refers to a liquid, such as a solution comprising impurities, waste, and/or nucleic acids, that flows out of a column after passing through the stationary phase. Unless otherwise clear from context, "flowthrough" or "breakthrough" of a column refers to a liquid that flows out of a column after passing through the stationary phase, the liquid comprising nucleic acids that were not bound by the stationary phase of the column. Two columns are said to be "capable of being used in series" if the output of a first column is capable of being directed into the second column, thereby becoming input for the second column. In a set of columns having more than two columns, the set of columns is "capable of being used in series" if each column in the set is capable of being used in series with at least 1 other column in the set. For instance, if a set of columns contains 3 columns, in some embodiments, the first column is capable of being used in series with the second column, the second column is capable of being used in series with the first and third columns, and the third column is capable of being used in series with the second column; in some embodiments, the first and third columns are also capable of being used in series.

Two columns may be capable of being used in series, such that flowthrough comprising nucleic acid may be directed into a next column in series if desired, but are not said to be "used in series" if the output is instead directed elsewhere, such as into a waste collection area or product collection area. For example, if the output of a first column flows into a valve, which may direct the output into either a second column, or another direction, such as a collection vessel, the two columns are capable of being used in series, but are said to be used in series if the valve actually directs the output into the second column (note that both columns are considered to be used in series, even though one column is producing output material and the other is receiving the material as input). Two columns are said to be "used in series" if the output of a first column is directed into the second column (e.g., using tubing, ports, valves, or any other manner of directing the output of the first column to the second column), thereby becoming input for the second column. In some embodiments, two or more columns are capable of being used in series, but not all columns are used in series simultaneously. In some embodiments, two or more columns are used in series when a first column is loaded with feed solution comprising a nucleic acid, thereby allowing the output of the first column to be added to a second column in series, such that any nucleic acids present in the flowthrough of the first column may be captured by the stationary phase of the second column. In some embodiments, columns capable of being used in series are not used in series, such as when one column is being washed, eluted, cleaned, or equilibrated. In some embodiments, a solution used to wash, clean, or equilibrate the column is directed into a waste collection area. In some embodiments, a solution used to elute nucleic acid from the column is directed into a product collection area (e.g., container, vessel, or vial). In some embodiments, a group of columns comprises a first column, a last column, and N intermediate columns, wherein the output of the first column is capable of being directed into an intermediate column, wherein the output of each of N-1 intermediate columns is capable of being directed into one other intermediate column, and the output of one intermediate column is capable of being directed into the last column. In such a group of columns connected in series, an input of the first column is capable of being directed into successive intermediate columns, then directed into the last column, finally flowing through as output of the last column. In some embodiments, the last column is connected in series to the first column, wherein the output of the last column is capable of being directed into the first column. In such a group of columns, an input of a given column may be passed through any successive series of columns starting with the given column, and any column may be treated as the "first column" to which an external input is added. In some embodiments, the number of intermediate columns N is any whole number (e.g., 0, 1, 2, 3, 4, 5, 6, 7, 8, 9, 10, 11, 12, 13, 14, 15, 16, 17, 18, 19, 20). In some embodiments, N is 0, wherein the method uses only a first column and a last column connected in series, with no intermediate columns. In some embodiments, N is 1, 2, 3, 4, 5, 6, 7, 8, 9, 10, 11, 12, 13, 14, 15, 16, 17, 18, 19, or 20. In some embodiments, N is at least 6.

Some aspects relate to methods of purifying a nucleic acid using at least four chromatography columns, wherein each column is capable of being used in series and in parallel with two or more other columns, the method comprising:

- (i) loading a first chromatography column by contacting a first stationary phase of the first chromatography column with a feed solution comprising one or more nucleic acids, optionally wherein the one or more nucleic acids are mRNAs;
- (ii) loading a second chromatography column and a third chromatography column in parallel by contacting, in series with the first chromatography column, (a) a second stationary phase of the second chromatography column with a first portion of the feed solution that has contacted the first stationary phase of the first chromatography column and (b) a third stationary phase of the third chromatography column with a second portion of the feed solution that has contacted the first stationary phase of the first chromatography column;
- (iii) loading the second chromatography column by contacting the second stationary phase with a portion of the feed solution that has not been contacted with the first stationary phase;
- (iv) loading the third chromatography column and a fourth chromatography column in parallel by contacting, in series with the second chromatography column, (a) the third stationary phase of the third chromatography column with a first portion of the feed solution that has contacted the second stationary phase of the second chromatography column and (b) a fourth stationary phase of the fourth chromatography column with a second portion of the feed solution that has contacted the second stationary phase of the second chromatography column; and
- (iv)(a) eluting the one or more nucleic acids from the first chromatography column.

In some embodiments, the loading of (ii) further comprises loading one or more additional chromatography columns in parallel with the second and third chromatography columns by contacting, in series with the first chromatography column, one or more additional stationary phases of one or more additional chromatography columns with one or more additional portions of the feed solution that have contacted the first stationary phase of the first chromatography column.

In some embodiments, the second and third chromatography columns of (ii) are loaded at about the same time. In some embodiments, one or more additional chromatography columns of (ii) are loaded at about the same time as the second and third chromatography columns. In some embodiments, the third and fourth chromatography columns of (iv)(a) are loaded at about the same time. In some embodiments, a first column is capable of being used in series and in parallel with multiple columns. For instance, a first column is capable of being used in series and in parallel with a second and third column if the output of the first column is capable of being divided and directed into both the second column and the third column. In some embodiments, the output of a first column is divided into approximately equal amounts, such that each column connected in series receives an approximately equal amount of output from the first column. In some embodiments, the output of a first column is divided into unequal amounts, such that one or more columns connected in series receive different amounts of output from the first column. In some embodiments, the last chromatography column in the set is capable of being used in series with the first and second chromatography columns in parallel. In some embodiments, the last chromatography column in a set is capable of being used in series with 2, 3, 4, 5, 6, 7, 8, or more chromatography columns in parallel.

In some embodiments, a group of columns comprises a first column, N intermediate columns, wherein in N is at least 2, and a last column, wherein the output of the first column is capable of being directed in parallel into two or more intermediate columns, the output of each intermediate column is capable of being directed in parallel into two or more other columns, the output of at least one intermediate column is capable of being directed in parallel into another intermediate column and into the last column, the output of at least one intermediate column is capable of being directed in parallel into the last column and into the first column, and the output of the last column is capable of being directed in parallel into the first column and into at least one intermediate column. In some embodiments, the number of intermediate columns N is any whole number greater than 1 (e.g. 2, 3, 4, 5, 6, 7, 8, 9, 10, 11, 12, 13, 14, 15, 16, 17, 18, 19, 20). In some embodiments, N is 2, wherein the method uses four columns, and each column is connected in series to 2 other columns in parallel. In some embodiments, N is 2, 3, 4, 5, 6, 7, 8, 9, 10, 11, 12, 13, 14, 15, 16, 17, 18, 19, or 20. In some embodiments, N is at least 6. In some embodiments, the output of each column is capable of being directed into P other columns in parallel, wherein P is at least 2, but less than the number of columns in a set. In some embodiments, P is 2, 3, 4, 5, 6, 7, 8, 9, 10, 11, 12, 13, 14, 15, 16, 17, 18, or 19. In some embodiments, P is at least 5.

In some embodiments, the step of contacting a column with the feed solution or output from a previous column in series is performed for about 2 minutes to about 10 minutes, about 3 minutes to about 7 minutes, or about 5 minutes to about 6 minutes. In some embodiments, the eluting of (iv)(a) is performed for about 1 minute to about 4 minutes, about 1.25 minutes to about 3 minutes, or about 1.5 minutes to about 2 minutes.

In some embodiments, the eluting from the first chromatography column is under conditions in which the first and second chromatography columns are not in series. Two columns are "not in series" if the output of neither column is directed into the other column (i.e., the output of the first column is not added as input to the second column, and the output of the second column is not added to the first column). In chromatography methods for use in purifying nucleic acids, the eluate containing nucleic acid may be directed into a product collection area, such as a vessel for storing purified nucleic acid.

In some embodiments, the second chromatography column is the last chromatography column. If the second chromatography column is the last chromatography column, then the method uses only two chromatography columns that are capable of being connected in series. In embodiments using only two chromatography columns, the output of a column is not directed into more than one column.

In some embodiments, the at least three chromatography columns capable of being used in series comprise 3, 4, 5, 6, 7, 8, or more chromatography columns. In some embodiments, 3 chromatography columns are capable of being connected in series. In some embodiments, 4 chromatography columns are capable of being connected in series. In some embodiments, 5 chromatography columns are capable of being connected in series. In some embodiments, 6 chromatography columns are capable of being connected in series. In some embodiments, 7 chromatography columns are capable of being connected in series. In some embodiments, 8 chromatography columns are capable of being connected in series. In some embodiments, 9 chromatography columns are capable of being connected in series. In some embodiments, 10 chromatography columns are capable of being connected in series.

Some embodiments comprise a first chromatography column, a last chromatography column, and one or more additional chromatography columns. In some embodiments, each additional chromatography column is capable of being used in consecutive series with two other chromatography columns: one as a receiver of material and one as a giver of material. In some embodiments, each chromatography column is capable of being used in series with two other chromatography columns in parallel. In some embodiments, the first chromatography column is capable of being used in consecutive series with the last (e.g., eighth) and second chromatography column (e.g., receiving input from the last chromatography column, and output being directed into the second chromatography column); the second chromatography column is capable of being used in consecutive series with the first and third chromatography columns; the third chromatography column is capable of being used in consecutive series with the second and fourth chromatography columns; the fourth chromatography column is capable of being used in consecutive series with the third and fifth chromatography columns; the fifth chromatography column is capable of being used in consecutive series with the fourth and sixth chromatography columns; the sixth chromatography column is capable of being used in consecutive series with the fifth and seventh chromatography columns; the seventh chromatography column is capable of being used in consecutive series with the sixth and eighth chromatography columns; and the eighth chromatography column is capable of being used in consecutive series with the seventh and first chromatography columns.

Some embodiments comprise at least four chromatography columns, wherein a given chromatography column is capable of being used in series with multiple other columns in parallel, wherein the output of a given column is divided and applied to each of the one or more other columns. In some embodiments, a set of columns comprises eight chromatography columns, wherein the first chromatography column is capable of being used in series with the second and third columns in parallel; the second chromatography column is capable of being used in series with the third and fourth columns in parallel; the third chromatography column is capable of being used in series with the fourth and fifth columns in parallel; the fourth column is capable of being used in series with the fifth and sixth columns in parallel; the fifth column is capable of being used in series with the sixth and seventh columns in parallel; the sixth column is capable of being used in series with the seventh and eighth columns in parallel; the seventh column is capable of being used in series with the eighth and first columns in parallel; and the eighth column is capable of being used in series with the first and second columns in parallel.

In some embodiments, the method further comprises:

(iii)(a) contacting the second stationary phase with a portion of the feed solution that has not been contacted with the first stationary phase; and (iii)(b) contacting, in series with the second chromatography column, a third stationary phase of a third chromatography column with the portion of the feed solution that has contacted the second stationary phase of the second chromatography column.

In some embodiments, the method further comprises:

(iii) loading the second chromatography column by contacting the second stationary phase with a portion of the feed solution that has not been contacted with the first stationary phase;

(iv) loading a third and fourth chromatography column in parallel by contacting, in series with the second chromatography column, (a) a third stationary phase of the third chromatography column with a first portion of the feed solution that has contacted the second stationary phase of the second chromatography column; and (b) a fourth stationary phase of the fourth chromatography column with a second portion of the feed solution that has contacted the second stationary phase of the second chromatography column.

In some embodiments, the loading of (iv) further comprises loading one or more additional chromatography columns in parallel with the third and fourth chromatography columns by contacting, in series with the second chromatography column, one or more additional stationary phases of one or more additional chromatography columns with one or more additional portions of the feed solution that have contacted the second stationary phase of the second chromatography column.

In some embodiments, the method further comprises: contacting a last stationary phase of a last chromatography column with an additional portion of the feed solution that has not been contacted with a stationary phase; and contacting, in series with the last chromatography column, the first stationary phase of the first chromatography column with an additional portion of the feed solution that has contacted the last stationary phase of the last chromatography column. In some embodiments, the method further comprises in series with the last chromatography column, contacting in parallel (a) the first stationary phase of the first chromatography column with a first portion of the additional feed solution that has contacted the last stationary phase of the last chromatography column and (b) the second stationary phase of the second chromatography column with a second portion of the additional feed solution that has contacted the last stationary phase of the last chromatography column. In some embodiments, the method further comprises in series with the last chromatography column, contacting in parallel with the first and second chromatography columns (c) one or more additional stationary phases of one or more additional chromatography columns with one or more additional portions of the additional feed solution that have contacted the last stationary phase of the last chromatography column. In some embodiments, the flowthrough of the last stationary phase comprises nucleic acid and is added to the first stationary phase of the first chromatography column. In some embodiments, the flowthrough of the last stationary phase comprises nucleic acid and is also added to the second stationary phase of the second chromatography column in parallel to being added to the first chromatography column. In some embodiments, the flowthrough of the last stationary phase comprises nucleic acid and is also added to the additional stationary phases of the one or more additional chromatography columns in parallel with being added to the first and second chromatography columns. In some embodiments, the first, second, and one or more additional chromatography columns have been washed, eluted, cleaned, and equilibrated prior to the addition of the flowthrough from the last chromatography column.

In some embodiments, the method is an automated method. In some embodiments of an automated method, a computer and/or pump controls an apparatus containing one or more solutions including feed solution, washing solution, eluting solution, cleaning solution, and equilibration solution, and controls the direction of each solution into one or more columns, to ensure that inputs and outputs are directed according to a desired method. In some embodiments, the computer controls the direction of the outputs of each chromatography column, determining whether each output is directed into another chromatography column, a waste collection area, or a product collection area.

In some embodiments, each chromatography column is independently capable of receiving output from a previous column in series, input material from the feed solution, a wash solution, an elution solution, a cleaning solution, and an equilibration solution.

In some embodiments, each chromatography column is independently capable of directing material to one or more different chromatography column used in series alone or in parallel, a waste collection area, and a product collection area. In some embodiments, output of a column is directed through a valve that is capable of directing the output into one or more different chromatography columns used in series alone or in parallel, a waste collection area, or a product collection area. In some embodiments, the valve is manually adjusted by a user to direct the output to a different chromatography column, waste collection area, or product collection area. In some embodiments, a computer controls whether the valve directs the output to a different chromatography column, waste collection area, or product collection area.

In some embodiments, the following steps are conducted at the same time: at least one column is loaded with feed solution; at least one column is washed; at least one column is eluted; at least one column is cleaned; and at least one column is equilibrated. In some embodiments, each of a feed solution, washing solution, elution solution, cleaning solution, and equilibration solution are added to a different column at about the same time. In some embodiments, each of a feed solution, washing solution, elution solution, cleaning solution, and equilibration solution, is present in a separate column at about the same time. In some embodiments, one or more other columns are loaded, at about the same time, with output from the column that is loaded with feed solution. In some embodiments, output from a column loaded with feed solution is present in one or more other columns at about the same time.

In some embodiments, the method further comprises:

(ii)(b) contacting the first stationary phase with a washing solution, wherein output comprising the washing solution is directed to a waste collection area. Washing solution refers to a mobile phase that interacts more strongly with other components of a mixture, such as salts, nucleotide triphosphates, and enzymes used in an in vitro transcription reaction, than with mRNA. Passage of a washing solution through the stationary phase of a column comprising mRNA bound to the stationary phase thus carries impurities through the column, which can be directed into a waste container, while allowing mRNA to remain bound to the stationary phase. "Washing" a column refers to the process of passing a washing solution through the column. Washing a column comprising mRNA bound to the stationary phase allows for the removal of impurities from the column, thereby allowing for subsequent elution of mRNA with a reduced concentration of impurities.

In some embodiments, the washing solution comprises Tris. In some embodiments, the concentration of Tris in the washing solution is about 0.1 mM to 500 mM. In some embodiments, the concentration of Tris in the washing solution is about 0.1 mM to about 1 mM, about 1 mM to about 10 mM, about 10 mM to about 100 mM, or about 100 mM to about 500 mM. In some embodiments, the washing solution comprises about 10 mM Tris.

In some embodiments, the washing solution comprises EDTA. In some embodiments, the concentration of EDTA in the washing solution is about 0.01 mM to 100 mM. In some embodiments, the concentration of EDTA in the washing solution is about 0.01 mM to about 0.1 mM, about 0.1 mM to about 1 mM, about 1 mM to about 10 mM, or about 10 mM to about 100 mM. In some embodiments, the washing solution comprises about 1 mM EDTA.

In some embodiments, the washing solution comprises a salt selected from the group consisting of sodium acetate (NaCOOH), ammonium acetate ($NH_4COOH$), potassium acetate (KCOOH), sodium chloride (NaCl), lithium chloride (LiCl), and potassium chloride (KCl). In some embodiments, the concentration of salt in the washing solution is between about 0.01 mM to about 10 M. In some embodiments, the concentration of salt in the washing solution is about 0.01 mM to about 0.1 mM, about 0.1 mM to about 1 mM, about 1 mM to about 10 mM, about 10 mM to about 100 mM, about 100 mM to about 1 M, or about 1 M to about 10 M. In some embodiments, the washing solution comprises NaCl. In some embodiments, the concentration of NaCl in the washing solution is between about 0.01 mM to about 10 M. In some embodiments, the concentration of NaCl in the washing solution is about 0.01 mM to about 0.1 mM, about 0.1 mM to about 1 mM, about 1 mM to about 10 mM, about 10 mM to about 100 mM, about 100 mM to about 1 M, or about 1 M to about 10 M. In some embodiments, the washing solution comprises about 0.1 M NaCl. In some embodiments, the washing solution comprises about 0.5 M NaCl.

In some embodiments, the pH of the washing solution is about 6.5 to about 8.5. In some embodiments, the pH of the washing solution is about 6.5 to about 7.0, about 7.0 to about 7.5, about 7.5 to about 8.0, and about 8.0 to about 8.5. In some embodiments, the pH of the washing solution is about 7.2 to about 7.6. In some embodiments, the washing solution has a pH of about 7.4.

In some embodiments, the washing solution comprises about 10 mM Tris, about 1 mM EDTA, about 0.1 M NaCl, and has a pH of about 7.4. In some embodiments, the washing solution comprises about 10 mM Tris, about 1 mM EDTA, about 0.5 M NaCl, and has a of about pH 7.4. In some embodiments, the volume of washing solution added to the stationary phase of a column is about 1, 2, 3, 4, 5, 6, 7, 8, 9, or 10 times the volume of the stationary phase of the column.

In some embodiments, the method further comprises:

(iv)(c) contacting the first stationary phase with a cleaning solution, wherein the output comprising the cleaning solution is directed to a waste collection area. "Cleaning solution," "rejuvenation solution," or "rejuvenating solution" refer to a solution that removes residual nucleic acid and other impurities from the column, so that it can be used to capture a new nucleic acid species without contamination from previously captured nucleic acids. In some embodiments, the cleaning solution comprises NaOH. In some embodiments, the concentration of NaOH in the cleaning solution is about 0.01 mM to about 0.1 mM, about 0.1 mM to about 1 mM, about 1 mM to about 10 mM, about 10 mM to about 100 mM, about 100 mM to about 1 M, or about 1 M to about 10 M. In some embodiments, the cleaning solution comprises about 0.05 M NaOH to 0.5 M NaOH. In some cleaning, the cleaning solution comprises 0.1 M NaOH. In some embodiments, the volume of cleaning solution added to the stationary phase of a column is about 1, 2, 3, 4, 5, 6, 7, 8, 9, or 10 times the volume of the stationary phase of the column. In some embodiments, about the volume of cleaning solution that is added to the column is about 3 times the volume of the stationary phase of a column. In some embodiments, cleaning solution is applied to the column for at least 5, at least 10, at least 15, at least 20, at least 25, at least 30, at least 35, at least 40, at least 45, at least 50, at least 55, or at least 60 minutes.

In some embodiments, the method further comprises:

(iii)(d) contacting the first stationary phase with an equilibration solution, wherein the output comprising the equilibration solution is directed to a waste collection area. "Equilibration solution" or "equilibrating solution" refers to a solution that is capable of enhancing the ability of a stationary phase to bind nucleic acid. "Equilibrating" a column refers to the process of passing an equilibration solution through the column. When a solution comprising nucleic acid passes through the stationary phase, the pH, conductivity, and salt concentrations at the interface between the solution and stationary phase affect the efficiency with which nucleic acids are captured. Equilibrating the column adjusts the pH, conductivity, and/or salt concentrations of the stationary phase, such nucleic acids passing through the column after equilibration are bound more efficiently than if the column had not been equilibrated.

In some embodiments, the equilibration solution comprises Tris. In some embodiments, the concentration of Tris in the equilibration solution is about 0.1 mM to 500 mM. In some embodiments, the concentration of Tris in the equilibration solution is about 0.1 mM to about 1 mM, about 1 mM to about 10 mM, about 10 mM to about 100 mM, or about 100 mM to about 500 mM. In some embodiments, the equilibration solution comprises 50 mM Tris.

In some embodiments, the equilibration solution comprises EDTA. In some embodiments, the concentration of EDTA in the equilibration solution is about 0.01 mM to 100 mM. In some embodiments, the concentration of EDTA in the equilibration solution is about 0.01 mM to about 0.1 mM, about 0.1 mM to about 1 mM, about 1 mM to about 10 mM, or about 10 mM to about 100 mM. In some embodiments, the equilibration solution comprises 5 mM EDTA.

In some embodiments, the pH of the equilibration solution is about 6.5 to about 8.5. In some embodiments, the pH of the equilibration solution is about 6.5 to about 7.0, about 7.0 to about 7.5, about 7.5 to about 8.0, and about 8.0 to about 8.5. In some embodiments, the pH of the equilibration solution is about 7.2 to about 7.6. In some embodiments, the equilibration solution has a pH of about 7.4.

In some embodiments, the equilibration solution comprises about 50 mM Tris, about 5 mM EDTA, and has a pH of about 7.4.

In some embodiments, the volume of equilibration solution added to the stationary phase of a column is about 1, 2, 3, 4, 5, 6, 7, 8, 9, or 10 times the volume of the stationary phase of the column. In some embodiments, about the volume of equilibration solution that is added to the column is about 3 times the volume of the stationary phase of a column.

In some embodiments, each column in a group of columns is capable of receiving input from a previous column capable of being used in series, or alternatively one or more inputs from external sources. In some embodiments, the input from an external source is a feed solution comprising mRNA, a washing solution, an elution buffer, a cleaning solution, or an equilibrating solution. In some embodiments, a column in a group of columns receives the following inputs, in order:

(i) output from a previous column in series, wherein the output from the previous column comprises nucleic acid, optionally wherein the nucleic acid is mRNA;

(ii) feed solution comprising nucleic acid, optionally wherein the nucleic acid is mRNA;

(iii) washing solution;

(iv) elution buffer;

(v) cleaning solution;

(vi) equilibration buffer;

wherein the addition of one input to the column is ceased before the next input is added.

In some embodiments, step (i) is repeated two or more times, with the column receiving output from a different previous column in series each time step (i) is repeated. In some embodiments, the method comprises waiting a period of at least 30 seconds, 60 seconds, 90 seconds, 120 seconds, 150 seconds, 180 seconds, 210 seconds, 240 seconds, 270 seconds, or 300 seconds after the addition of one input is ceased before the next input is added. In some embodiments, the next input is not added until at least 70%, at least 80%, at least 90%, or up to 100% of the previous input has left the column. In some embodiments, after the output from the previous column in series of (vi) is added, the feed solution comprising nucleic acid is added to the column, beginning a new cycle. In some embodiments, the cycle is repeated until the feed solution comprising nucleic acid is exhausted. In some embodiments, after the feed solution comprising nucleic acid is exhausted, washing solution is added to the column to remove impurities, followed by elution buffer to elute bound nucleic acid. In some embodiments, the cycle of inputs is performed in parallel on multiple columns. In some embodiments, the cycle is performed in parallel on all columns in the group. In some embodiments, after the feed solution comprising nucleic acid is exhausted, washing solution is added to each of the columns comprising bound nucleic acid to remove impurities, followed by elution buffer to elute bound nucleic acid.

In some embodiments, the method comprises repeating steps (i)(a) through (iv)(c), wherein the first chromatography column is treated as the last chromatography column of steps (iv)(a) through (iv)(c), and the first of the one or more additional chromatography columns is treated as the first chromatography column of steps (i)(a) through (iv)(c).

In some embodiments, the pH of the feed solution comprising nucleic acid is between about 6.8 and 8.5. In some embodiments, the pH of the feed solution comprising nucleic acid is about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, or about 8.5. In some embodiments, the pH of the feed solution is about 7.0. In some embodiments, the pH of the solution in contact with the stationary phase of a column is between about 6.8 and 8.5. In some embodiments, the pH of the solution in contact with the stationary phase of a column is about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, or about 8.5. In some embodiments, the pH of the solution in contact with the stationary phase of a column is about 6.8. In some embodiments, the pH of the solution in contact with the stationary phase of a column is about 6.9. In some embodiments, the pH of the solution in contact with the stationary phase of a column is about 7.0. In some embodiments, the pH of the solution in contact with the stationary phase of a column is about 7.1. In some embodiments, the pH of the solution in contact with the stationary phase of a column is about 7.2. In some embodiments, the pH of the solution in contact with the stationary phase of a column is about 7.3. In some embodiments, the pH of the solution in contact with the stationary phase of a column is about 7.4. In some embodiments, the pH of the solution in contact with the stationary phase of a column is about 7.5. In some embodiments, the pH of the solution in contact with the stationary phase of a column is about 7.6. In some embodiments, the pH of the solution in contact with the stationary phase of a column is about 7.7. In some embodiments, the pH of the solution in contact with the stationary phase of a column is about 7.8. In some embodiments, the pH of the solution in contact with the stationary phase of a column is about 7.9. In some embodiments, the pH of the solution in contact with the stationary phase of a column is about 8.0.

In some embodiments, each of the first and one or more additional chromatography columns comprise a total of about 0.5 L to about 2 L, about 2 L to about 5 L, about 5 L to about 10 L, or about 10 L to about 20 L of stationary phase. The volume of stationary phase in a column refers to the volume of a three-dimensional shape formed by the interfaces of the stationary phase with interior walls of the column and/or air. For example, in a cylindrical column with an area of 25π $cm^2$ and packed with stationary phase to form a 100 cm cylinder, the total volume of stationary phase in the column would be 2,500π $cm^3$, approximately 7,854 $cm^3$ or 7.854 L.

The temperature of the column (e.g., the stationary phase within the column) can vary. In some embodiments, each of the first and one or more additional chromatography columns has a temperature from about 20° C. to about 100° C. (e.g., any temperature between 20° C. and 99° C.). In some embodiments, each of the first and one or more additional chromatography columns has a temperature from about 40° C. to about 100° C. (e.g., any temperature between 40° C. and 99° C., for example about 40° C., about 50° C., about 60° C., about 70° C., about 80° C., about 90° C., about 95° C., or about 100° C.). In some embodiments, each of the first and one or more additional chromatography columns has a temperature from about 70° C. to about 90° C. (e.g., any temperature between 70° C. and 90° C.). In some embodiments, each of the first and one or more additional chromatography columns has a temperature of about 80° C.

The temperature of the column (e.g., the stationary phase within the column) can vary. In some embodiments, each of the first and one or more additional chromatography columns has a temperature from about 4° C. to about 99° C. (e.g., any temperature between 4° C. and 99° C.). In some embodiments, each of the first and one or more additional chromatography columns has a temperature from about 4° C. to about 40° C. (e.g., any temperature between 4° C. and 40° C., for example about 4° C., about 10° C., about 20° C., about 25° C., about 30° C., about 35° C., or about 40° C.). In some embodiments, each of the first and one or more additional chromatography columns has a temperature from about 20° C. to about 40° C. (e.g., any temperature between 20° C. and 40° C.). In some embodiments, each of the first and one or more additional chromatography columns has a temperature of about 30° C. In some embodiments, the binding of the RNA to the oligo-dT resin occurs at a temperature of lower than 40° C. In some embodiments, the binding of the RNA to the oligo-dT resin occurs at a temperature of 4° C. to 30° C., 4° C. to 25° C., 4° C. to 20° C., 4° C. to 15° C., 4° C. to 10° C., 4° C. to 8° C., 10° C. to 30° C., 10° C. to 25° C., 10° C. to 20° C., 10° C. to 15° C., or 15° C. to 25° C.

In some embodiments, the conductivity of the feed solution is about 2-5 mS/cm, 2-7 mS/cm, 5-10 mS/cm, 5-15 mS/cm, 5-7 mS/cm, 6-9 mS/cm, 8-10 mS/cm, 9-12 mS/cm, 10-15 mS/cm, 15-20 mS/cm, 20-25 mS/cm, 25-30 mS/cm, 30-35 mS/cm, 35-40 mS/cm, 40-45 mS/cm, 45-50 mS/cm, 50-60 mS/cm, 60-70 mS/cm, 70-80 mS/cm, 80-90 mS/cm, or 90-100 mS/cm. In some embodiments, the conductivity of the feed solution is at least 10 mS/cm. In some embodiments, the conductivity of the feed solution is about 40 mS/cm. In some embodiments, the conductivity of the solution in contact with the stationary phase of a column is about 2-5 mS/cm, 2-7 mS/cm, 5-10 mS/cm, 5-15 mS/cm, 5-7 mS/cm, 6-9 mS/cm, 8-10 mS/cm, 9-12 mS/cm, 10-15 mS/cm, 15-20 mS/cm, 20-25 mS/cm, 25-30 mS/cm, 30-35 mS/cm, 35-40 mS/cm, 40-45 mS/cm, 45-50 mS/cm, 50-60 mS/cm, 60-70 mS/cm, 70-80 mS/cm, 80-90 mS/cm, or 90-100 mS/cm. In some embodiments, the conductivity of the solution in contact with the stationary phase is at least 10 mS/cm. In some embodiments, the conductivity of the solution in contact with the stationary phase is about 40 mS/cm. Interaction of mRNA with oligo-dT, and thus binding of the mRNA to the stationary phase of the column, requires that the adenine nucleotides of the polyA tail be exposed in order to form hydrogen bonds with the thymidine bases of oligo-dT. If the polyA tail of an mRNA forms a secondary structure in which fewer adenine bases are exposed, the mRNA is more likely to pass through the stationary phase without binding to oligo-dT, reducing the efficiency of the chromatography process. Adjusting the conductivity of the feed solution, or at the interface of a solution and the stationary phase, promotes the unfolding of secondary structures in the polyA tail of mRNAs, and exposure of adenine bases, thereby promoting binding of the mRNA to the stationary phase.

In some embodiments, the conductivity of the feed solution is increased or achieved by the addition of a high-salt buffer. In some embodiments, a high-salt buffer (e.g., that may be mixed with feed solution) comprises a salt concentration of at least 50 mM, at least 60 mM, at least 70 mM, at least 80 mM, at least 90 mM, at least 100 mM, at least 125 mM, at least 150 mM, at least 200 mM, at least 250 mM, at least 300 mM, at least 350 mM, at least 400 mM, at least 500 mM, at least 600 mM, at least 700 mM, at least 800 mM, at least 900 mM, or at least 1000 mM. In some embodiments, a high-salt buffer comprises a salt concentration of 50-500 mM, 50-250 mM, 50-100 mM, 50-75 mM, 60-150 mM, 75-500 mM, 75-200 mM, 100-500 mM, 100-250 mM, 150-350 mM, 200-400 mM, 250-500 mM, 300-400 mM, 350-450 mM, 400-500 mM, 400-600 mM, 500-700 mM, 500-750 mM, 700-1000 mM, 750-900 mM, or 850-1000 mM. In some embodiments, a high-salt buffer comprises a salt concentration of 1-2 M, 2-3 M, 3-4 M, or 4-5 M. In some embodiments, a high-salt buffer comprises a conductivity of at least 5 mS/cm, at least 6 mS/cm, at least 7 mS/cm, at least 8 mS/cm, at least 9 mS/cm, at least 10 mS/cm, at least 12 mS/cm, or at least 15 mS/cm. In some embodiments, a high-salt buffer comprises a conductivity of 5-10 mS/cm, 5-15 mS/cm, 5-7 mS/cm, 6-9 mS/cm, 8-10 mS/cm, 9-12 mS/cm, or 10-15 mS/cm. In some embodiments, the salt concentration of the feed solution after high-salt buffer addition is at least 100 mM, at least 200 mM, at least 300 mM, at least 400 mM, at least 500 mM, at least 600 mM, at least 700 mM, at least 800 mM, at least 900 mM, at least 1 M, or more. In some embodiments, after high-salt buffer addition, the feed solution has a salt concentration of about 100 mM to about 200 mM, about 200 mM to about 400 mM, about 400 mM to about 600 mM, about 600 mM to about 800 mM, about 800 mM to about 1 M, about 1 M to about 1.5 M, about 1.5 M to about 2 M, about 2 M to about 2.5 M, about 2.5 M to about 3 M, about 3 M to about 4 M, or about 4 M to about 5 M. In some embodiments, after high-salt buffer addition, the feed solution has a salt concentration of about 400 mM to about 600 mM. In some embodiments, after high-salt buffer addition, the feed solution comprises a salt concentration of about 500 mM. In some embodiments, the salt concentration of the feed solution refers to the concentration of sodium chloride, potassium chloride, lithium chloride, monosodium phosphate, or trisodium phosphate in the composition.

In some embodiments, the feed solution comprises about 0.25 mg/ml to about 10 mg/ml mRNA, about 0.5 mg/ml to about 8 mg/ml mRNA, about 0.75 to about 7 mg/ml mRNA, about 1 mg/ml to about 6 mg/ml mRNA, about 2 mg/mL to about 5 mg/mL mRNA, about 2.25 mg/mL to about 4 mg/mL mg/mL mRNA, or about 2.5 mg/mL to about 3 mg/mL mRNA. In some embodiments, the feed solution comprises at least 5 mg/mL, at least 6 mg/mL, at least 7 mg/mL, at least 8 mg/mL, at least 9 mg/mL, at least 10 mg/mL, or more mRNA. In some embodiments, the feed solution comprises about 5 mg/mL to about 10 mg/mL mRNA. In some embodiments, the feed solution comprises about 6 mg/mL to about 10 mg/mL mRNA. In some embodiments, the feed solution comprises about 7 mg/mL to about 10 mg/mL mRNA. In some embodiments, the feed solution comprises about 8 mg/mL to about 10 mg/mL mRNA. In some embodiments, the feed solution comprises about 9 mg/mL to about 10 mg/mL mRNA. In some embodiments, feed solution is added to a column for a duration of time sufficient to deliver an amount of mRNA corresponding to at least 80%, at least 90%, at least 95%, or up to 100% of the binding capacity of the column. In some embodiments, feed solution is added to the column for a duration of time sufficient to saturate the stationary phase of the column with mRNA. In some embodiments, after the stationary phase of a column is saturated with mRNA, the feed solution is added to the next column in series.

In some embodiments, loading of the first chromatography column comprises contacting the first stationary phase with at least 2 g, at least 3 g, at least 4 g, at least 5 g, at least 6 g, at least 7 g, at least 8 g, at least 9 g, at least 10 g, or more mRNA per L of stationary phase present in the first chromatography column. The mass of nucleic acid (e.g., mRNA) that is added to a given volume of stationary phase is referred to as a "load challenge." For example, in a method where a feed solution containing a total of 4 g mRNA is added to a column containing 0.5 L of stationary phase, the load challenge is 8 g/L. In some embodiments, the load challenge is about 2-50 g/L, 2-40 g/L, 2-30 g/L, 2-10 g/L, 5-50 g/L, 5-40 g/L, 5-30 g/L, 5-20 g/L, 5-10 g/L, 10-50 g/L, 10-40 g/L, 10-30 g/L, or 10-20 g/L. In some embodiments, the load challenge is about 2 g/L to about 5 g/L, about 5 g/L to about 10 g/L, about 10 g/L to about 15 g/L, about 15 g/L to about 20 g/L, about 20 g/L to about 30 g/L, about 30 g/L to about 40 g/L, or about 40 g/L to about 50 g/L. In some embodiments, the load challenge is at least 2 g/L, at least 3 g/L, at least 4 g/L, at least 5 g/L, at least 6 g/L, at least 7 g/L, at least 8 g/L, at least 9 g/L, at least 10 g/L, at least 15 g/L, at least 20 g/L, at least 25 g/L, at least 30 g/L, at least 35 g/L, at least 40 g/L, at least 45 g/L, or at least 50 g/L.

In some embodiments, at least 0.25 g, at least 0.5 g, at least 0.75 g, at least 1 g, at least 2 g, at least 3 g, at least 4 g, at least 5 g, at least 6 g, at least 7 g, at least 8 g, at least 9 g, or up to 10 g of mRNA is eluted per liter of stationary phase comprised in all columns per hour of performing the method. In some embodiments, at least 4 g of mRNA is eluted per liter of stationary phase comprised in all columns per hour of performing the method. In some embodiments, at least 5 g of mRNA is eluted per liter of stationary phase comprised in all columns per hour of performing the method. In some embodiments, at least 6 g of mRNA is eluted per liter of stationary phase comprised in all columns per hour of performing the method. In some embodiments, at least 7 g of mRNA is eluted per liter of stationary phase comprised in all columns per hour of performing the method. In some embodiments, at least 8 g of mRNA is eluted per liter of stationary phase comprised in all columns per hour of performing the method. In some embodiments, at least 9 g of mRNA is eluted per liter of stationary phase comprised in all columns per hour of performing the method. In some embodiments, at least 10 g of mRNA is eluted per liter of stationary phase comprised in all columns per hour of performing the method. In some embodiments, at least 10 g of impure RNA is loaded onto the columns (i.e., is purified), such as 20 g, 30 g, 40 g, 50 g, 75 g, 100 g, 200 g, 300 g, 400 g, 500 g, 600 g, 700 g, 800 g, 900 g, 1,000 g, or more. In some embodiments, the amount of time spent performing the method is measured starting from when feed solution is first added to any column, and ending when feed solution is exhausted. In some embodiments the amount of time spent performing the method is measured starting from when feed solution is first added to any column, and ending after elution of any bound mRNA in any columns that contained mRNA when the feed solution became exhausted.

In some embodiments, at least 60%, at least 65%, at least 70%, at least 75%, at least 80%, at least 85%, at least 90%, at least 95%, at least 96%, at least 97%, at least 98%, at least 99%, or up to 100% of eluted mRNAs comprise a poly(A) tail. In some embodiments, at least 70% of the eluted mRNAs comprise a poly(A) tail. In some embodiments, at least 80% of the eluted mRNAs comprise a poly(A) tail. In some embodiments, at least 90% of the eluted mRNAs comprise a poly(A) tail. In some embodiments, at least 95% of eluted mRNAs comprise a poly(A) tail. In some embodiments, at least 80%, at least 85%, at least 90%, at least 95%, at least 96%, at least 97%, at least 98%, at least 99%, or up to 100% of eluted mRNAs have about the same length. In some embodiments, at least 85% of eluted mRNAs have about the same length. In some embodiments, at least 80%, at least 85%, at least 90%, at least 95%, at least 96%, at least 97%, at least 98%, at least 99%, or up to 100% of eluted mRNAs are of an expected length. In some embodiments, at least 85% of eluted mRNAs are of an expected length. Expected length refers to the length of the sequence that is encoded by a DNA template for in vitro transcription.

In some embodiments, at least 80%, at least 85%, at least 90%, at least 95%, at least 96%, at least 97%, at least 98%, at least 99%, or up to 100% of the mRNAs of the feed solution are eluted. In some embodiments, at least 75% of the mRNAs of the feed solution are eluted.

The multicolumn chromatography methods disclosed herein result in greater productivity. "Productivity," as used herein, refers to a quantitative value of output product (i.e., nucleic acid) obtained from the process. More specifically, productivity is the quantitative measure of nucleic acid purified using a given volume of stationary phase in a given length of time, expressed in units of (mass)(volume of stationary phase)$^{-1}$·(time)$^{-1}$ (e.g., g·L$^{-1}$·hr$^{-1}$). In some embodiments, the productivity of the method is a least about 0.25 g/L·hr, optionally wherein the productivity of the method is about 0.5 g/L·hr, about 0.75 g/L·hr, about 3 g/L·hr, about 4 g/L·hr, about 5 g/L·hr, about 6 g/L·hr, about 7 g/L·hr, about 8 g/L·hr, about 9 g/L·hr, about 10 g/L·hr, or more. A greater productivity is assessed relative to the amount of nucleic acid purified using batch chromatography methods under equivalent conditions. In some embodiments, the method results in an increase of at least 50%, at least 100%, at least 150%, at least 200%, at least 250%, at least 300%, at least 350%, at least 400%, at least 450%, at least 500%, at least 550%, at least 600%, at least 650%, at least 700%, at least 750%, at least 800%, at least 850%, at least 900%, at least 950%, at least 1000%, at least 1100%, at least 1200%, at least 1300%, at least 1400%, at least 1500%, at least 1600%, at least 1700%, at least 1800%, at least 1900%, or up to 2000% relative to a batch chromatography process. In some embodiments, the multicolumn chromatography results in an increase in productivity from about 50% to about 300%, about 300% to about 500%, about 500% to about 700%, about 700% to about 1000%, about 1000% to about 1500%, or about 1500% to about 2000%. A batch chromatography process refers to a method of column chromatography in which one or more columns that are not connected in series are used to purify a nucleic acid. In some embodiments, the increase in productivity resulting from a multicolumn chromatography process is measured relative to a batch chromatography process using an equivalent amount of resin. In some embodiments, the increase in productivity is measured relative to a batch chromatography process using an equivalent amount of resin distributed among multiple columns. In some embodiments, the increase in productivity is measured relative to a batch chromatography process using an equivalent amount of resin in a single column. In some embodiments, the increase in productivity is measured relative to a batch chromatography process in which the same nucleic acid species (e.g., a nucleic acid comprising the same nucleic acid sequence) is purified. In some embodiments, the total volume of resin comprised within the columns of the multicolumn chromatography method is between about 0.1 L to about 100 L. In some embodiments, the total volume of resin is about 0.1 L to about 0.5 L, 0.5 L to about 2 L, about 2 L to about 4 L, about 4 L to about 6 L, about 6 L to about 8 L, about 8 L to about 10 L, about 10 L to about 15 L, about 15 L to about 20 L, about 20 L to about 25 L, about 25 L to about 30 L, about 30 L to about 40 L, about 40 L to about 50 L, about 50 L to about 75 L, or about 75 L to about 100 L.

Salt Intensification of Column Chromatography

In some embodiments, a high-salt buffer is added to the feed solution to increase the salt concentration, adding the composition to a stationary phase to bind mRNA to the stationary phase, and eluting bound mRNA from the stationary phase to obtain eluted mRNA. Addition of a high-salt buffer promotes formation of compact secondary structures by mRNAs, but leaving the poly(A) tail exposed. Exposure of the poly(A) tail allows mRNAs to bind to stationary phases such as oligo-dT resin, but the compact structure induced by high salt concentrations reduces steric interactions in which a portion of a stationary phase-bound first mRNA prevents a second mRNA from binding to the stationary phase. Thus, adding a high-salt feed solution to a stationary phase causes more mRNA molecules to bind to the stationary phase than addition of an equivalent feed solution with a lower salt concentration. However, mRNA must be dissolved in a solution in order to pass through a stationary phase. The benefits of high salt concentrations for increasing binding of mRNA to stationary phase must therefore be balanced with the risk of mRNA precipitation. Surprisingly, precipitation requires an extended amount of time even at high salt concentrations. Accordingly, addition of a high-salt buffer to a feed solution to produce a high-salt feed solution followed by adding the high-salt feed solution to a stationary phase shortly thereafter, allows the benefits of high salt concentrations for stationary phase binding to be realized without a consequent reduction in yield due to mRNA precipitation.

In some embodiments, the method comprises heating the feed solution to denature RNA before the high-salt buffer is added (i.e., the high-salt buffer is added to a composition comprising denatured RNA). Denaturation disrupts the secondary structure of nucleic acids (e.g., mRNAs), promoting release of bound impurities and the formation of linear nucleic acid structures. RNA may be denatured using any method. In some embodiments, RNA is denatured by heating a feed solution before the high-salt buffer is added. In some embodiments, RNA is denatured by heating the feed solution after the high-salt buffer is added. In some embodiments, RNA is denatured by heating the feed solution to 60° C. to 90° C., 60° C. to 80° C., 60° C. to 70° C., 65° C. to 85° C., 65° C. to 75° C., 70° C. to 90° C., 70° C. to 80° C., 65° C. to 70° C., 70° C. to 75° C., or 75° C. to 95° C. In some embodiments, the feed solution is heated for less than 2 minutes, less than 90 seconds, less than 1 minute, less than 50 seconds, less than 40 seconds, less than 30 seconds, less than 20 seconds, or less than 10 seconds. In some embodiments, the feed solution is heated for 5-90 seconds, 5-60 seconds, 5-30 seconds, 5-15 seconds, 10-60 seconds, 10-30 seconds, 20-60 seconds, 20-40 seconds, 30-90 seconds, 30-60 seconds, 40-90 seconds, 40-60 seconds, 60-120 seconds, 60-90 seconds, or 90-120 seconds. In some embodiments, the high-salt feed solution is heated in the presence of a denaturant molecule (e.g., a chemical small molecule that destabilizes or denatures RNA). A denaturant molecule may include dimethyl sulfoxide (e.g., at a concentration of 0.05-1% v/v, 0.1-0.5% v/v, 0.05-0.5% v/v, or 0.25-0.75% v/v), guanidine (e.g., at a concentration of 50-250 mM, 100-500 mM, 250-1000 mM, 1-8 M, 2-6 M, 3-5 M, or 5-8 M), or urea (e.g., at a concentration of 50-250 mM, 100-500 mM, 250-1000 mM, 1-8 M, 2-6 M, 3-5 M, or 5-8 M).

In some embodiments, a change in the relative amount of denatured RNA in an feed solution during a denaturation process (e.g., heating the feed solution to 60° C. to 90° C., 60° C. to 80° C., 60° C. to 70° C., 65° C. to 85° C., 65° C. to 75° C., 70° C. to 90° C., 70° C. to 80° C., 65° C. to 70° C., 70° C. to 75° C., or 75° C. to 95° C.) is determined by hyperchromicity curves (e.g., spectroscopic melting curves). In some embodiments, a change in the relative amount of denatured RNA is determined by measuring the change in secondary structure of the total RNA in a composition (e.g., by determining a change in ultraviolet absorption). In some embodiments, a change in the relative amount of denatured RNA is determined by monitoring the change in secondary structure of the total RNA in a composition (e.g., by determining a change in ultraviolet absorption) before and after the denaturation process (e.g., heating the feed solution to 60° C. to 90° C., 60° C. to 80° C., 60° C. to 70° C., 65° C. to 85° C., 65° C. to 75° C., 70° C. to 90° C., 70° C. to 80° C., 65° C. to 70° C., 70° C. to 75° C., or 75° C. to 95° C.).

In some embodiments, at least 50%, 55%, 60%, 65%, 70%, 75%, 80%, or 85% of the total RNA in a denatured RNA feed solution comprises denatured RNA. In some embodiments, at least 90% (e.g., at least 91%, 92%, 93%, 94%, 95%, 96%, 97%, 98%, 99% or 100%) of the total RNA in a denatured RNA feed solution comprises denatured RNA. In some embodiments, 50-70%, 45-60%, 55-70%, 60-80%, 60-100%, 75-100%, 50-95%, 75-95%, 80-100%, 80-90%, 90-95%, 95-100%, 90-99%, or 95-99% of the total RNA in a denatured RNA feed solution comprises denatured RNA. In some embodiments, the relative amount of denatured RNA in a denatured RNA feed solution is determined by hyperchromicity curves (e.g., spectroscopic melting curves). Hyperchromicity, the property of nucleic acids such as RNA to exhibit an increase in extinction coefficient upon the loss of structure during heating, may be measured (e.g., during denaturation of RNA, e.g., by heating) using a spectrophotometer. In some embodiments, the extinction coefficient of RNA is measured at 205 nm, 220 nm, 260 nm, or 200-300 nm. In some embodiments, the relative amount of denatured RNA in a denatured RNA feed solution is determined using a method as described in S. J. Schroeder and D. H. Turner, "Optical melting measurements of nucleic acid thermodynamics", Methods Enzymol. 468 (2009) 371-387; or Gruenwedel, D. W., "Nucleic Acids: Properties and Determination", Encyclopedia of Food Sciences and Nutrition, 2003, Pages 4147-4152.

In some embodiments, the high-salt buffer is added to the RNA feed solution by in-line mixing. In some embodiments, in-line mixing refers to mixing of a first continuous stream of a solution with a second continuous stream of a solution. In some embodiments, the first and second continuous streams are controlled by independent pumps (e.g., independent peristaltic pumps). In some embodiments, in-line mixing relies on flow control conditions, for example, process flow conditions wherein flow parameters (e.g., flow rate, temperature) are controlled by a flow regulating device comprising at least one pump system. In some embodiments, the first continuous stream is a high-salt buffer (e.g., comprising at least 100 mM salt), and the second continuous stream is a composition comprising RNA. In some embodiments, the RNA feed solution has been desalted (e.g., is a low-salt RNA feed solution) and/or comprises denatured RNA. In-line mixing typically occurs shortly prior to binding a composition comprising RNA to a stationary phase. In some embodiments, in-line mixing occurs for less than 2 minutes, less than 90 seconds, less than 1 minute, less than 50 seconds, less than 40 seconds, less than 30 seconds, less than 20 seconds, or less than 10 seconds. In some embodiments, in-line mixing occurs for 5-90 seconds, 5-60 seconds, 5-30 seconds, 5-15 seconds, 10-60 seconds, 10-30 seconds, 20-60 seconds, 20-40 seconds, 30-90 seconds, 30-60 seconds, 40-90 seconds, 40-60 seconds, 60-120 seconds, 60-90 seconds, or 90-120 seconds. In some embodiments, in-line mixing occurs at a temperature of 4° C. to 30° C., 4° C. to 25° C., 4° C. to 20° C., 4° C. to 15° C., 4° C. to 10° C., 4° C. to 8° C., 10° C. to 30° C., 10° C. to 25° C., 10° C. to 20° C., 10° C. to 15° C., or 15° C. to 25° C.

In some embodiments, the high-salt buffer is added to the RNA feed solution by bolus addition. In contrast to in-line mixing in which two liquid streams are combined continuously, bolus addition involves the discrete addition of one composition to another. Bolus addition may occur over several seconds or minutes, and be followed by mixing to incorporate the high-salt buffer throughout the RNA feed solution, thereby distributing salts of the high-salt buffer throughout the RNA feed solution.

In some embodiments, the high-salt buffer is added to the RNA feed solution 5-90 seconds, 5-60 seconds, 5-30 seconds, 5-15 seconds, 10-60 seconds, 10-30 seconds, 20-60 seconds, 20-40 seconds, 30-90 seconds, 30-60 seconds, 40-90 seconds, 40-60 seconds, 60-120 seconds, 60-90 seconds, or 90-120 seconds prior to binding a composition comprising RNA to a stationary phase. In some embodiments, addition of the high-salt buffer occurs 1-60 minutes, 1-45 minutes, 1-30 minutes, 1-25 minutes, 1-20 minutes, 1-15 minutes, 1-10 minutes, 1-5 minutes, or 1-2 minutes prior to adding the high-salt RNA feed solution to the stationary phase. In some embodiments, adding the high-salt RNA feed solution to the stationary phase occurs within 1 hour or less, 45 minutes or less, 30 minutes or less, 25 minutes or less, 20 minutes or less, 15 minutes or less, 10 minutes or less, 9 minutes or less, 8 minutes or less, 7 minutes or less, 6 minutes or less, 5 minutes or less, 4 minutes or less, 3 minutes or less, 2 minutes or less, or 1 minute or less of adding the high-salt buffer to the RNA feed solution. In some embodiments, the high-salt buffer, the RNA feed solution, and/or the high-salt RNA feed solution produced by adding the high-salt buffer has a temperature of 4° C. to 30° C., 4° C. to 25° C., 4° C. to 20° C., 4° C. to 15° C., 4° C. to 10° C., 4° C. to 8° C., 10° C. to 30° C., 10° C. to 25° C., 10° C. to 20° C., 10° C. to 15° C., or 15° C. to 25° C.

In some embodiments, a high-salt buffer (e.g., that may be mixed with an RNA feed solution) comprises a salt concentration of at least 50 mM, at least 60 mM, at least 70 mM, at least 80 mM, at least 90 mM, at least 100 mM, at least 125 mM, at least 150 mM, at least 200 mM, at least 250 mM, at least 300 mM, at least 350 mM, at least 400 mM, at least 500 mM, at least 600 mM, at least 700 mM, at least 800 mM, at least 900 mM, or at least 1000 mM. In some embodiments, a high-salt buffer comprises a salt concentration of 50-500 mM, 50-250 mM, 50-100 mM, 50-75 mM, 60-150 mM, 75-500 mM, 75-200 mM, 100-500 mM, 100-250 mM, 150-350 mM, 200-400 mM, 250-500 mM, 300-400 mM, 350-450 mM, 400-500 mM, 400-600 mM, 500-700 mM, 500-750 mM, 700-1000 mM, 750-900 mM, or 850-1000 mM. In some embodiments, a high-salt buffer comprises a salt concentration of 1-2 M, 2-3 M, 3-4 M, or 4-5 M. In some embodiments, a high-salt buffer comprises a conductivity of at least 5 mS/cm, at least 6 mS/cm, at least 7 mS/cm, at least 8 mS/cm, at least 9 mS/cm, at least 10 mS/cm, at least 12 mS/cm, or at least 15 mS/cm. In some embodiments, a high-salt buffer comprises a conductivity of 5-10 mS/cm, 5-15 mS/cm, 5-7 mS/cm, 6-9 mS/cm, 8-10 mS/cm, 9-12 mS/cm, or 10-15 mS/cm.

In some embodiments, mixing a composition comprising RNA with a high-salt buffer produces a high-salt RNA feed solution comprising RNA and salt at a concentration of at least 100 mM. In some embodiments, mixing a composition comprising RNA with a high-salt buffer produces a composition comprising RNA and salt at a concentration of 100-500 mM, 100-250 mM, 150-350 mM, 200-400 mM, 250-500 mM, 300-400 mM, 350-450 mM, 400-500 mM, 400-600 mM, 500-700 mM, 500-750 mM, 700-1000 mM, 750-900 mM, or 850-1000 mM. In some embodiments, the salt concentration of the high-salt RNA feed solution is at least 100 mM, at least 200 mM, at least 300 mM, at least 400 mM, at least 500 mM, at least 600 mM, at least 700 mM, at least 800 mM, at least 900 mM, at least 1 M, or more. In some embodiments, the high-salt RNA feed solution has a salt concentration of about 100 mM to about 200 mM, about 200 mM to about 400 mM, about 400 mM to about 600 mM, about 600 mM to about 800 mM, about 800 mM to about 1 M, about 1 M to about 1.5 M, about 1.5 M to about 2 M, about 2 M to about 2.5 M, about 2.5 M to about 3 M, about 3 M to about 4 M, or about 4 M to about 5 M. In some embodiments, the high-salt mRNA feed solution has a salt concentration of about 400 mM to about 600 mM. In some embodiments, the high-salt RNA feed solution comprises a salt concentration of about 500 mM. In some embodiments, the salt concentration of the high-salt RNA feed solution refers to the concentration of sodium chloride, potassium chloride, ammonium chloride, ammonium sulfate, monosodium phosphate, disodium phosphate, or trisodium phosphate in the composition. In some embodiments, mixing a composition comprising RNA with a high-salt buffer produces a composition comprising RNA and salt having a conductivity of less than 2 mS/cm. In some embodiments, mixing a composition comprising RNA with a high-salt buffer produces a composition comprising RNA and salt having a conductivity of 2-5 mS/cm, 2-7 mS/cm, 5-10 mS/cm, 5-15 mS/cm, 5-7 mS/cm, 6-9 mS/cm, 8-10 mS/cm, 9-12 mS/cm, or 10-15 mS/cm.

In some embodiments, a buffer (e.g., a low-salt or high-salt buffer) comprises NaCl, KCl, LiCl, $NaH_2PO_4$, $Na_2HPO_4$, or $Na_3PO_4$. In some embodiments, a buffer (e.g., a low-salt or high-salt buffer) comprises any source of sodium, potassium, magnesium, phosphate, chloride, or any other source of salt ions. In some embodiments, a buffer (e.g., a low-salt or high-salt buffer) may further comprise a buffering agent in order to maintain a consistent pH. In some embodiments, a buffer (e.g., a low-salt or high-salt buffer) comprises a neutral pH. In some embodiments, a buffer (e.g., a low-salt or high-salt buffer) comprises a pH of about 6, about 6.5, about 7, about 7.4, about 8, or about 6-8. Examples of buffering agents for use herein include ethylenediamine tetraacetic acid (EDTA), succinate, citrate, aspartic acid, glutamic acid, maleate, cacodylate, 2-(N-morpholino)-ethanesulfonic acid (MES), N-(2-acetamido)-2-aminoethanesulfonic acid (ACES), piperazine-N,N'-2-ethanesulfonic acid (PIPES), 2-(N-morpholino)-2-hydroxy-propanesulfonic acid (MOPSO), N,N-bis-(hydroxyethyl)-2-aminoethanesulfonic acid (BES), 3-(N-morpholino)-propanesulfonic acid (MOPS), N-2-hydroxyethyl-piperazine-N-2-ethanesulfonic acid (HEPES), 3-(N-tris-(hydroxymethyl)methylamino)-2-hydroxypropanesulfonic acid (TAPSO), 3-(N,N-bis[2-hydroxyethyl]amino)-2-hydroxypropanesulfonic acid (DIPSO), N-(2-hydroxyethyl) piperazine-N'-(2-hydroxypropanesulfonic acid) (HEPPSO), 4-(2-hydroxyethyl)-1-piperazine propanesulfonic acid (EPPS), N-[tris(hydroxymethyl)-methyl]glycine (Tricine), N,N-bis(2-hydroxyethyl)glycine (Bicine), [(2-hydroxy-1,1-bis(hydroxymethyl)ethyl)amino]-1-propanesulfonic acid (TAPS), N-(1,1-dimethyl-2-hydroxyethyl)-3-amino-2-hydroxypropanesulfonic acid (AMPSO), tris(hydroxymethyl) aminomethane (Tris), and bis[2-hydroxyethyl]iminotris-[hydroxymethyl]methane (Bis-Tris). Other buffers compositions, buffer concentrations, and additional components of a solution for use herein will be apparent to those skilled in the art.

In some embodiments, mixing comprises cooling of a composition comprising RNA to a temperature of 4° C. to 30° C., 4° C. to 25° C., 4° C. to 20° C., 4° C. to 15° C., 4° C. to 10° C., 4° C. to 8° C., 10° C. to 30° C., 10° C. to 25° C., 10° C. to 20° C., 10° C. to 15° C., or 15° C. to 25° C. In some embodiments, mixing comprises cooling of a composition comprising RNA to a temperature below 60° C., 55° C., 50° C., 45° C., 40° C., 35° C., 30° C., 25° C., 20° C., 15° C., 10° C., or 5° C. In some embodiments, cooling occurs simultaneously with mixing of a composition comprising RNA and low salt buffer with a high salt buffer. In some embodiments, during cooling, a composition comprising RNA is maintained at a total salt concentration of less than 20 mM, less than 15 mM, less than 10 mM, less than 5 mM, or less than 1 mM. In some embodiments, during cooling, a composition comprising RNA is maintained at a total salt concentration of 1-20 mM, 1-15 mM, 1-10 mM, 1-5 mM, 5-20 mM, 5-10 mM, 10-20 mM, 10-15 mM or 15-20 mM. In some embodiments, cooling occurs simultaneously with mixing of a composition comprising RNA and low salt buffer with a high salt buffer. In some embodiments, during cooling, a composition comprising RNA is maintained at less than 2.5 mS/cm, less than 2 mS/cm, less than 1.5 mS/cm, less than 1 mS/cm, or less than 0.5 mS/cm. In some embodiments, cooling occurs simultaneously with mixing of a composition comprising RNA and low salt buffer with a high salt buffer. In some embodiments, during cooling, a composition comprising RNA is maintained at 0.1-2.5 mS/cm, 0.1-2 mS/cm, 0.5-2 mS/cm, 0.5-1 mS/cm, 1-2 mS/cm, 1-1.5 mS/cm, or 1-1.25 mS/cm.

Some embodiments of chromatography methods involve the production of high-salt RNA feed solutions in which most or all RNA molecules are dissolved in solution. In some embodiments, the high-salt RNA feed solution comprises at least 2.0 g/L, 2.5 g/L, 3.0 g/L, 3.5 g/L, 4.0 g/L, 4.5 g/L, 5.0 g/L, 6.0 g/L, 7.0 g/L, 8.0 g/L, 9.0 g/L, 10.0 g/L, or more dissolved RNA. In some embodiments, the high-salt RNA feed solution comprises about 2.0 g/L to about 4.0 g/L, about 4.0 g/L to about 6.0 g/L, about 6.0 g/L to about 8.0 g/L, or about 8.0 g/L to about 10.0 g/L dissolved RNA. In some embodiments, the high-salt RNA feed solution comprises about 4.0 g/L to about 6.0 g/L dissolved RNA. In some embodiments, at least at least 80%, at least 85%, at least 90%, at least 95%, at least 97%, at least 98%, at least 99%, or up to 100% of RNAs in the high-salt mRNA feed solution are dissolved mRNAs. In some embodiments, the concentration of precipitated (i.e., solid) RNA in the composition is 0.5 g/L or less, 0.4 g/L or less, 0.3 g/L or less, 0.2 g/L or less, 0.1 g/L or less, or 0.05 g/L or less. In some embodiments, the high-salt RNA feed solution does not comprise precipitated RNA. Methods of measuring the mass of precipitated RNA in a composition are generally known in the art, and include separation and weighing of the precipitate, or desalting and resolubilizing the precipitate to quantify the amount of RNA by spectroscopy. In some embodiments, the percentage of RNAs in a composition that are dissolved RNAs is calculated by determining the mass of precipitated RNA in the composition, determining the mass of dissolved RNA in the composition, and calculating the percentage of all RNA in the composition that is precipitated RNA. In some embodiments, absence of a precipitate, or absence of RNA in the precipitate, indicates that all RNAs in the composition are dissolved RNAs. Some embodiments of the methods herein involve binding (i.e., contacting) compositions comprising RNA to a stationary phase. In some embodiments, methods herein comprise binding compositions comprising RNA to the stationary phase following mixing of RNA feed solutions with high-salt buffers.

In some embodiments, the stationary phase comprises fiber, particles, resin, and/or beads, Examples of stationary phases include but are not limited to resin, silica (e.g., alkylated and non-alkylated silica), polystyrenes (e.g., alkylated and non-alkylated polystyrenes), polystyrene divinylbenzenes, etc. In some embodiments, a stationary phase comprises particles, for example porous particles. In some embodiments, a stationary phase (e.g., particles of a stationary phase) is hydrophobic (e.g., made of an intrinsically hydrophobic material, such as polystyrene divinylbenzene), or comprise hydrophobic functional groups. In some embodiments, a stationary phase is a membrane or monolithic stationary phase. A monolithic stationary phase is a continuous, unitary, porous structure prepared by in situ polymerization or consolidation inside the column tubing. In some embodiments, the surface is functionalized to convert it into a sorbent with the desired chromatographic binding properties.

The particle size (e.g., as measured by the diameter of the particle) of an HPLC stationary phase can vary. In some embodiments, the particle size of a HPLC stationary phase ranges from about 1 μm to about 100 μm (e.g., any value between 1 and 100, inclusive) in diameter. In some embodiments, the particle size of a HPLC stationary phase ranges from about 2 μm to about 10 μm, about 2 μm to about 6 μm, or about 4 μm in diameter. The pore size of particles (e.g., as measured by the diameter of the pore) can also vary. In some embodiments, the particles comprise pores having a diameter of about 100 Å to about 10,000 Å. In some embodiments, the particles comprise pores having a diameter of about 100 Å to about 5000 Å, about 100 Å to about 1000 Å, or about 1000 Å to about 2000 Å. In some embodiments, the stationary phase comprises polystyrene divinylbenzene, for example as used in PLRP-S 4000 columns or DNAPac-RP columns.

In some embodiments, the stationary phase comprises a hydrophobic interaction chromatography (HIC) stationary phase, such as an HIC resin. Some embodiments of the methods described here may comprise any HIC resin. In some embodiments, the HIC resin comprises one or more butyl, phenyl, octyl, t-butyl, methyl, and/or ethyl functional groups. In some embodiments, the HIC resin is a HiTrap Butyl HP resin, CaptoPhenyl resin, Phenyl Sepharose 6 resin, Phenyl Sepharose™ High Performance resin, Octyl Sepharose™ High Performance resin, Fractogel™ EMD Propyl resin, Fractogel™ EMD Phenyl resin, Macro-Prep™ Methyl resin, HiScreen Butyl FF, HiScreen Octyl FF, or Tosoh Hexyl. In some embodiments, the HIC resin is a (poly)styrene-divinylbenzene (PS-DVB) R150 bead resin with 2000 Angstrom pores.

In some embodiments, the stationary phase comprises a capture nucleic acid (e.g. oligonucleotide or polynucleotide) that comprises a nucleotide sequence that is complementary to a nucleotide sequence of an mRNA of the high-salt RNA feed solution. Watson-Crick base pairing between the capture nucleic acid and the complementary sequence on the mRNA in the high-salt RNA feed solution promote retention of the mRNA by the stationary phase, while nucleic acids that lack the complementary sequence pass over the stationary phase due to lack of hybridization to the capture nucleic acid. In some embodiments, the capture nucleic acid is a DNA. In other embodiments, the capture nucleic acid is an RNA. In some embodiments, the capture nucleic acid comprises a nucleotide sequence that is 5-200, 10-50, 10-100, 50-200, 100-150, or 125-200 nucleotides in length that is complementary to a nucleotide sequence of an mRNA in the high-salt composition. In some embodiments, the capture nucleic acid is 5-200, 10-50, 10-100, 50-200, 100-150, or 125-200 nucleotides in length. In some embodiments, the capture nucleic acid is linked to a bead and/or resin of the stationary phase by a linker.

In some embodiments, the stationary phase comprises oligo-dT resin. In some embodiments, the oligo-dT resin is a (poly)styrene-divinylbenzene (PS-DVB) bead resin with 2000 Angstrom pores derivatized with poly dT. In some embodiments, poly dT comprises 5-200, 10-50, 10-100, 50-200, 100-150, or 125-200 thymidines and/or uracils. In some embodiments, poly dT comprises 20 thymidines in length. In some embodiments, poly dT is linked directly to the bead resin. In some embodiments, poly dT is linked to the bead resin via a linker.

In some embodiments, the stationary phase is equilibrated with a buffer prior to binding the RNA to the resin. In some embodiments, the stationary phase is equilibrated with a buffer comprising 100 mM NaCl, 10 mM Tris, and 1 mM EDTA at pH 7.4. In some embodiments, the stationary phase is washed with a buffer after the RNA is bound to the stationary phase. In some embodiments, the washing step comprises a buffer comprising 100 mM NaCl, 10 mM Tris, and 1 mM EDTA, at pH 7.4.

In some embodiments, the binding of the RNA to the stationary phase occurs at a temperature of lower than 40° C. In some embodiments, the binding of the RNA to the stationary phase occurs at a temperature of 4° C. to 30° C., 4° C. to 25° C., 4° C. to 20° C., 4° C. to 15° C., 4° C. to 10° C., 4° C. to 8° C., 10° C. to 30° C., 10° C. to 25° C., 10° C. to 20° C., 10° C. to 15° C., or 15° C. to 25° C.

In some embodiments, the high-salt RNA feed solution comprising RNA is bound to or in contact with the stationary phase for a total residence time of less than 20 minutes, less than 18 minutes, less than 15 minutes, less than 12 minutes, less than 10 minutes, less than 9 minutes, less than 8 minutes, less than 7 minutes, less than 6 minutes, less than 5 minutes, less than 4 minutes, less than 3 minutes, less than 2 minutes, or less than 1 minute. In some embodiments, the composition comprising RNA is bound to or in contact with the stationary phase for a total residence time of 1-2, 1-5, 2-5, 2-10, 5-20, 5-10, 5-15, 8-15, 10-15, 12-20, or 15-20 minutes.

In some embodiments, the stationary phase is comprised in a column. In some embodiments, the concentration of RNA in the high-salt RNA feed solution is less than 100%, less than 90%, less than 80%, less than 70%, less than 60%, or less than 50% of the dynamic binding capacity of the column. Dynamic binding capacity refers to the amount or concentration of an analyte (e.g., RNA) that can be passed through a column without significant breakthrough of the analyte. Contacting a column or stationary phase with a composition comprising an analyte concentration that exceeds the dynamic binding capacity causes analyte to pass through the stationary phase without being bound, reducing analyte yield. In some embodiments, at least 70%, at least 75%, at least 80%, at least 85%, at least 90%, at least 91%, at least 92%, at least 93%, at least 94%, at least 95%, at least 96%, at least 97%, at least 98%, at least 99%, or up to 100% of mRNAs in the high-salt RNA feed solution bind to the stationary phase.

In some embodiments, addition of a high-salt buffer prior to binding the RNA to the stationary phase increases the productivity of the method. In some embodiments, the productivity of the method is a least about 0.25 g/L·hr, optionally wherein the productivity of the method is about 0.5 g/L·hr, about 0.75 g/L·hr, about 3 g/L·hr, about 4 g/L·hr, about 5 g/L·hr, about 6 g/L·hr, about 7 g/L·hr, about 8 g/L·hr, about 9 g/L·hr, about 10 g/L·hr, or more. In some embodiments, the total volume of stationary phase comprised within the column is between about 0.1 L to about 100 L. In some embodiments, the total volume of stationary phase is about 0.1 L to about 0.5 L, 0.5 L to about 2 L, about 2 L to about 4 L, about 4 L to about 6 L, about 6 L to about 8 L, about 8 L to about 10 L, about 10 L to about 15 L, about 15 L to about 20 L, about 20 L to about 25 L, about 25 L to about 30 L, about 30 L to about 40 L, about 40 L to about 50 L, about 50 L to about 75 L, or about 75 L to about 100 L.

In some embodiments, the methods comprise eluting RNA from the stationary phase. In some embodiments, the RNA is eluted from the stationary phase using water or a buffer (e.g., a buffer comprising 10 mM Tris, 1 mM EDTA, at pH 8.0).

In some embodiments, the RNA eluted from the stationary phase comprises at least 50%, 55%, 60%, 65%, 70%, 75%, 80%, or 85% poly-A tailed RNA. In some embodiments, the RNA eluted from the stationary phase comprises about 20-100%, 20-90%, 20-80%, 20-70%, 20-60%, 20-50%, 20-40%, 20-30%, 25-75%, 30-50%, 40-60%, 50-70%, 45-60%, 55-70%, 60-80%, 60-100%, 75-100%, 50-95%, 75-95%, 80-100%, 80-90%, 90-95%, 95-100%, 90-99%, or 95-99% poly-A tailed mRNA. In some embodiments, the RNA eluted from the stationary phase comprises at least 91%, 92%, 93%, 94%, 95%, 96%, 97%, 98%, 99% or 100% poly-A tailed mRNA.

In some embodiments, mixtures comprising RNA are desalted to produce low-salt RNA feed solutions (e.g., having less than 50 mM total salt concentration). In some embodiments, a mixture comprising RNA (e.g., a mixture produced by an IVT reaction) is desalted prior to denaturation of the RNA and/or mixing with a high-salt buffer. In some embodiments, a desalting occurs after denaturation (e.g., by heating), but before addition of the high-salt buffer. In some embodiments, desalting occurs before denaturation, and the low-salt mRNA feed solution is heated to denature the mRNA. In some embodiments, the RNA feed solution is desalted, but not denatured, before addition of the high-salt buffer.

In some embodiments, a low-salt RNA feed solution comprises sodium, potassium, magnesium, manganese, calcium, sulfate, phosphate, and/or chloride salts. In some embodiments, a low-salt RNA feed solution comprises sodium chloride, sodium phosphate, sodium sulfate, potassium chloride, potassium phosphate, potassium sulfate, magnesium chloride, magnesium phosphate, magnesium sulfate, calcium chloride, calcium phosphate, and/or calcium sulfate. In some embodiments, a low-salt RNA feed solution comprises a total salt concentration of less than 20 mM, less than 15 mM, less than 10 mM, less than 5 mM, or less than 1 mM. In some embodiments, a low-salt RNA feed solution comprises a salt concentration of 1-20 mM, 1-15 mM, 1-10 mM, 1-5 mM, 5-20 mM, 5-10 mM, 10-20 mM, 10-15 mM or 15-20 mM. In some embodiments, a low-salt RNA feed solution results in a conductivity of less than 2.5 mS/cm, less than 2 mS/cm, less than 1.5 mS/cm, less than 1 mS/cm, or less than 0.5 mS/cm. In some embodiments, a low-salt RNA feed solution comprises a conductivity of 0.1-2.5 mS/cm, 0.1-2 mS/cm, 0.5-2 mS/cm, 0.5-1 mS/cm, 1-2 mS/cm, 1-1.5 mS/cm, or 1-1.25 mS/cm.

In some embodiments, desalting a mixture comprising RNA is accomplished by binding the RNA to a hydrophobic interaction chromatography (HIC) resin and eluting the RNA from the HIC resin to produce the low-salt RNA feed solution. In some embodiments, the HIC resin is equilibrated with a buffer prior to binding the RNA to the resin. In some embodiments, the HIC resin is equilibrated with a buffer comprising 100 mM NaCl, 10 mM Tris, 1 mM EDTA pH 7.4. In some embodiments, the RNA is eluted from the HIC resin using water or a buffer. Some embodiments of the methods described here may comprise any HIC resin. In some embodiments, the HIC resin comprises butyl, phenyl, octyl, t-butyl, methyl, and/or ethyl functional groups. In some embodiments, the HIC resin is a HiTrap Butyl HP resin, CaptoPhenyl resin, Phenyl Sepharose 6 resin, Phenyl Sepharose™ High Performance resin, Octyl Sepharose™ High Performance resin, Fractogel™ EMD Propyl resin, Fractogel™ EMD Phenyl resin, Macro-Prep™ Methyl resin, HiScreen Butyl FF, HiScreen Octyl FF, or Tosoh Hexyl. In some embodiments, the HIC resin is a (poly)styrene-divinylbenzene (PS-DVB) R150 bead resin with 2000 Angstrom pores.

In some embodiments, desalting a mixture comprising RNA is accomplished by dilution of the mixture with water (e.g., a lOx water dilution), tangential flow filtration (TFF) of the mixture into water, or ambient oligo-dT (i.e., under native, non-denaturing RNA conditions). In some embodiments, desalting a mixture comprising RNA is accomplished by tangential flow filtration.

In some embodiments, an RNA feed solution (e.g., a low-salt RNA feed solution) is denatured. In some embodiments, a low-salt RNA feed solution is denatured prior to (e.g., immediately prior to) mixing with a high-salt buffer and subsequent binding of the denatured RNA to a stationary phase.

Nucleic Acids

Aspects of the present disclosure relate to compositions comprising nucleic acids and methods of producing nucleic acids. As used herein, the term "nucleic acid" includes multiple nucleotides (i.e., molecules comprising a sugar (e.g., ribose or deoxyribose) linked to a phosphate group and to an exchangeable organic base, which is either a substituted pyrimidine (e.g., cytosine (C), thymine (T) or uracil (U)) or a substituted purine (e.g., adenine (A) or guanine (G))). The term nucleic acid includes polyribonucleotides as well as polydeoxyribonucleotides. The term nucleic acid also includes polynucleosides (i.e., a polynucleotide minus the phosphate) and any other organic base containing polymer. Non-limiting examples of nucleic acids include chromosomes, genomic loci, genes or gene segments that encode polynucleotides or polypeptides, coding sequences, non-coding sequences (e.g., intron, 5'-UTR, or 3'-UTR) of a gene, pri-mRNA, pre-mRNA, cDNA, mRNA, etc. A nucleic acid (e.g., mRNA) may include a substitution and/or modification. In some embodiments, the substitution and/or modification is in one or more bases and/or sugars. For example, in some embodiments a nucleic acid (e.g., mRNA) includes nucleotides having an organic group, such as a methyl group, attached to a nucleic acid base at the N6 position. Thus, in some embodiments, an mRNA includes one or more N6-methyladenosine nucleotides. A phosphate, sugar, or nucleic acid base of a nucleotide may also be substituted for another phosphate, sugar, or nucleic acid base. For example, a uridine base may be substituted for a pseudouridine base, in which the uracil base is attached to the sugar by a carbon-carbon bond rather than a nitrogen-carbon bond. Thus, in some embodiments, a nucleic acid (e.g., mRNA) is heterogeneous in backbone composition thereby containing any possible combination of polymer units linked together such as peptide-nucleic acids (which have an amino acid backbone with nucleic acid bases).

Some embodiments of nucleic acid sequences include nucleic acid sequences that have been removed from their naturally occurring environment, recombinant or cloned DNA isolates, and chemically synthesized analogues or analogues biologically synthesized by heterologous systems.

An "engineered nucleic acid" is a nucleic acid that does not occur in nature. It should be understood, however, that while an engineered nucleic acid as a whole is not naturally-occurring, it may include nucleotide sequences that occur in nature. In some embodiments, an engineered nucleic acid comprises nucleotide sequences from different organisms (e.g., from different species). For example, in some embodiments, an engineered nucleic acid includes a bacterial nucleotide sequence, a human nucleotide sequence, and/or a viral nucleotide sequence.

Engineered nucleic acids include recombinant nucleic acids and synthetic nucleic acids. A "recombinant nucleic acid" is a molecule that is constructed by joining nucleic acids (e.g., isolated nucleic acids, synthetic nucleic acids or a combination thereof) and, in some embodiments, can replicate in a living cell. A "synthetic nucleic acid" is a molecule that is amplified or chemically, or by other means, synthesized. A synthetic nucleic acid includes those that are chemically modified, or otherwise modified, but can base pair with naturally-occurring nucleic acid molecules. Recombinant and synthetic nucleic acids also include those molecules that result from the replication of either of the foregoing. A nucleic may comprise naturally occurring nucleotides and/or non-naturally occurring nucleotides such as modified nucleotides.

In some embodiments, a nucleic acid is present in (or on) a vector. Examples of vectors include but are not limited to bacterial plasmids, phage, cosmids, phasmids, fosmids, bacterial artificial chromosomes, yeast artificial chromosomes, viruses and retroviruses (for example vaccinia, adenovirus, adeno-associated virus, lentivirus, herpes-simplex virus, Epstein-Barr virus, fowlpox virus, pseudorabies, baculovirus) and vectors derived therefrom. In some embodiments, a nucleic acid (e.g., DNA) used as an input molecule for in vitro transcription (IVT) is present in a plasmid vector.

When applied to a nucleic acid sequence, the term "isolated" denotes that the polynucleotide sequence has been removed from its natural genetic milieu and is thus free of other extraneous or unwanted coding sequences (but may include naturally occurring 5' and 3' untranslated regions such as promoters and terminators), and is in a form suitable for use within genetically engineered protein production systems. Such isolated molecules are those that are separated from their natural environment.

In some embodiments, an input DNA for IVT is a nucleic acid vector. A "nucleic acid vector" is a polynucleotide that carries at least one foreign or heterologous nucleic acid fragment. A nucleic acid vector may function like a "molecular carrier", delivering fragments of nucleic acids or polynucleotides into a host cell or as a template for IVT. An "in vitro transcription template" (IVT template), or "input DNA" as used herein, refers to deoxyribonucleic acid (DNA) suitable for use in an IVT reaction for the production of messenger RNA (mRNA). In some embodiments, an IVT template encodes a 5' untranslated region, contains an open reading frame, and encodes a 3' untranslated region and a polyA tail. The particular nucleotide sequence composition and length of an IVT template will depend on the mRNA of interest encoded by the template.

In some embodiments the nucleic acid vector is a circular nucleic acid such as a plasmid. In other embodiments it is a linearized nucleic acid. According to some embodiments the nucleic acid vector comprises a predefined restriction site, which can be used for linearization. The linearization restriction site determines where the vector nucleic acid is opened/linearized. The restriction enzymes chosen for linearization should preferably not cut within the critical components of the vector.

A nucleic acid vector may include an insert which may be an expression cassette or open reading frame (ORF). An "open reading frame" is a continuous stretch of DNA beginning with a start codon (e.g., methionine (ATG)), and ending with a stop codon (e.g., TAA, TAG or TGA) and encodes a protein or peptide (e.g., a therapeutic protein or therapeutic peptide). In some embodiments, an expression cassette encodes an RNA including at least the following elements: a 5' untranslated region, an open reading frame region encoding the mRNA, a 3' untranslated region and a polyA tail. The open reading frame may encode any mRNA sequence, or portion thereof.

In some embodiments, a nucleic acid vector comprises a 5' untranslated region (UTR). A "5' untranslated region (UTR)" refers to a region of an mRNA that is directly upstream (i.e., 5') from the start codon (i.e., the first codon of an mRNA transcript translated by a ribosome) that does not encode a protein or peptide. 5' UTRs are further described herein, for example in the section entitled "Untranslated Regions".

In some embodiments, a nucleic acid vector comprises a 3' untranslated region (UTR). A "3' untranslated region (UTR)" refers to a region of an mRNA that is directly downstream (i.e., 3') from the stop codon (i.e., the codon of an mRNA transcript that signals a termination of translation) that does not encode a protein or peptide. 3' UTRs are further described herein, for example in the section entitled "Untranslated Regions".

The terms 5' and 3' are used herein to describe features of a nucleic acid sequence related to either the position of genetic elements and/or the direction of events (5' to 3'), such as e.g. transcription by RNA polymerase or translation by the ribosome which proceeds in 5' to 3' direction. Synonyms are upstream (5') and downstream (3'). Conventionally, DNA sequences, gene maps, vector cards and RNA sequences are drawn with 5' to 3' from left to right or the 5' to 3' direction is indicated with arrows, wherein the arrowhead points in the 3' direction. Accordingly, 5' (upstream) indicates genetic elements positioned towards the left-hand side, and 3' (downstream) indicates genetic elements positioned towards the right-hand side, when following this convention.

Aspects of the disclosure relate to populations of molecules. As used herein, a "population" of molecules (e.g., DNA molecules) generally refers to a preparation (e.g., a plasmid preparation) comprising a plurality of copies of the molecule (e.g., DNA) of interest, for example a cell extract preparation comprising a plurality of expression vectors encoding a molecule of interest (e.g., a DNA encoding an RNA of interest).

A nucleic acid (e.g., mRNA) typically comprises a plurality of nucleotides. A nucleotide includes a nitrogenous base, a five-carbon sugar (ribose or deoxyribose), and at least one phosphate group. Nucleotides include nucleoside monophosphates, nucleoside diphosphates, and nucleoside triphosphates. A nucleoside monophosphate (NMP) includes a nucleobase linked to a ribose and a single phosphate; a nucleoside diphosphate (NDP) includes a nucleobase linked to a ribose and two phosphates; and a nucleoside triphosphate (NTP) includes a nucleobase linked to a ribose and three phosphates. Nucleotide analogs are compounds that have the general structure of a nucleotide or are structurally similar to a nucleotide. Nucleotide analogs, for example, include an analog of the nucleobase, an analog of the sugar and/or an analog of the phosphate group(s) of a nucleotide.

A nucleoside includes a nitrogenous base and a 5-carbon sugar. Thus, a nucleoside plus a phosphate group yields a nucleotide. Nucleoside analogs are compounds that have the general structure of a nucleoside or are structurally similar to a nucleoside. Nucleoside analogs, for example, include an analog of the nucleobase and/or an analog of the sugar of a nucleoside.

It should be understood that the term "nucleotide" includes naturally-occurring nucleotides, synthetic nucleotides and modified nucleotides, unless indicated otherwise. Examples of naturally-occurring nucleotides used for the production of RNA, e.g., in an IVT reaction, include adenosine triphosphate (ATP), guanosine triphosphate (GTP), cytidine triphosphate (CTP), uridine triphosphate (UTP), and 5-methyluridine triphosphate ($m^5$UTP). In some embodiments, adenosine diphosphate (ADP), guanosine diphosphate (GDP), cytidine diphosphate (CDP), and/or uridine diphosphate (UDP) are used.

Examples of nucleotide analogs include, but are not limited to, antiviral nucleotide analogs, phosphate analogs (soluble or immobilized, hydrolyzable or non-hydrolyzable), dinucleotide, trinucleotide, tetranucleotide, e.g., a cap analog, or a precursor/substrate for enzymatic capping (vaccinia or ligase), a nucleotide labeled with a functional group to facilitate ligation/conjugation of cap or 5' moiety (IRES), a nucleotide labeled with a 5' $PO_4$ to facilitate ligation of cap or 5' moiety, or a nucleotide labeled with a functional group/protecting group that can be chemically or enzymatically cleaved. Examples of antiviral nucleotide/nucleoside analogs include, but are not limited, to Ganciclovir, Entecavir, Telbivudine, Vidarabine and Cidofovir.

Modified nucleotides may include modified nucleobases. For example, an RNA transcript (e.g., mRNA transcript) of the present disclosure may include a modified nucleobase selected from pseudouridine (ψ), 1-methylpseudouridine (m1ψ), 1-ethylpseudouridine, 2-thiouridine, 4'-thiouridine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methoxyuridine (mo5U) and 2'-O-methyl uridine. In some embodiments, an RNA transcript (e.g., mRNA transcript) includes a combination of at least two (e.g., 2, 3, 4 or more) of the foregoing modified nucleobases.

In Vitro Transcription

Aspects of the present disclosure relate to methods of producing (e.g., synthesizing) an RNA transcript (e.g., mRNA transcript) comprising contacting a DNA template (e.g., a first input DNA and a second input DNA) with an RNA polymerase (e.g., a T7 RNA polymerase, a T7 RNA polymerase variant, etc.) under conditions that result in the production of the RNA transcript. This process is referred to as "in vitro transcription" or "IVT". IVT conditions typically require a purified DNA template containing a promoter, nucleoside triphosphates, a buffer system that includes dithiothreitol (DTT) and magnesium ions, and an RNA polymerase. The exact conditions used in the transcription reaction depend on the amount of RNA needed for a specific application. Typical IVT reactions are performed by incubating a DNA template with an RNA polymerase and nucleoside triphosphates, including GTP, ATP, CTP, and UTP (or nucleotide analogs) in a transcription buffer. An RNA transcript having a 5' terminal guanosine triphosphate is produced from this reaction.

In some embodiments, an IVT reaction uses an RNA polymerase selected from the group consisting of T7 RNA polymerase, T3 RNA polymerase, K11 RNA polymerase, and SP6 RNA polymerase. In some embodiments, an IVT reaction uses a T3 RNA polymerase. In some embodiments, an IVT reaction uses an SP6 RNA polymerase. In some embodiments, an IVT reaction uses a K11 RNA polymerase. In some embodiments, an IVT reaction uses a T7 RNA polymerase. In some embodiments, a wild-type T7 polymerase is used in an IVT reaction. In some embodiments, a mutant T7 polymerase is used in an IVT reaction. In some embodiments, a T7 RNA polymerase variant comprises an amino acid sequence that shares at least 50%, 60%, 70%, 80%, 90%, 95%, or 99% identity with a wild-type T7 (WT T7) polymerase. In some embodiments, the T7 polymerase variant is a T7 polymerase variant described by International Application Publication Number WO2019/036682 or WO2020/172239, the entire contents of each of which are incorporated herein by reference. T7 RNA polymerase variants with one or more mutations relative to WT T7 RNA polymerase have several advantages in IVT reactions, including improved speed, fidelity, and reduced production of double-stranded RNA (dsRNA) transcripts. Double-stranded RNA transcripts, in which at least a portion of an RNA transcript is hybridized to another RNA molecule, elicit an innate immune response when introduced into a cell, causing degradation of both strands of a dsRNA. Minimizing the formation of dsRNA transcripts during IVT enables the production of less immunogenic, and thus more stable, RNA compositions. In some embodiments, the concentration of double-stranded RNA in a composition comprising RNA is 5% (% w/w) or less, 4% or less, 3% or less, 2.5% or less, 2% or less, 1.75% or less, 1.5% or less, 1.25% or less, 1% or less, 0.9% or less, 0.8% or less, 0.7% or less, 0.6% or less, 0.5% or less, 0.4% or less, 0.3% or less, 0.25% or less, 0.2% or less, 0.175% or less, 0.15% or less, 0.125% or less, or 0.1% or less. In some embodiments, the concentration of double-stranded RNA in a composition comprising RNA is 0.05% (% w/w) or less, 0.04% or less, 0.03% or less, 0.02% or less, or 0.01% or less. Methods of measuring the presence and/or amount of dsRNA in a composition are known in the art. Non-limiting examples of methods for measuring dsRNA content of a sample include ELISAs and immunoblotting using antibodies specific to dsRNA. Additionally, the total mass of RNA in a sample can be measured using techniques such as spectroscopy (NanoDrop), qRT-PCR, and/or ddPCR, and the mass of dsRNA can be measured using an intercalating agent that fluoresces when bound to dsRNA, such as acridine orange, with the dsRNA concentration being calculated by division. In some embodiments, the concentration of dsRNA in a composition refers to the mass of RNA nucleotides that are part of a double-stranded RNA:RNA hybrid, with other unhybridized nucleotides from either RNA in the hybrid not contributing to the amount of dsRNA in a composition. In other embodiments, the concentration of dsRNA in a sample refers to the concentration of RNA molecules containing nucleotides that are part of an RNA:RNA hybrid. In some embodiments, the RNA polymerase (e.g., T7 RNA polymerase or T7 RNA polymerase variant) is present in a reaction (e.g., an IVT reaction) at a concentration of 0.01 mg/ml to 1 mg/ml. For example, the RNA polymerase may be present in a reaction at a concentration of 0.01 mg/mL, 0.05 mg/ml, 0.1 mg/ml, 0.5 mg/ml or 1.0 mg/ml.

The "percent identity," "sequence identity," "% identity," or "% sequence identity" (as they may be interchangeably used herein) of two sequences (e.g., nucleic acid or amino acid) refers to a quantitative measurement of the similarity between two sequences (e.g., nucleic acid or amino acid). Percent identity can be determined using the algorithms of Karlin and Altschul, Proc. Natl. Acad. Sci. USA 87:2264-68, 1990, modified as in Karlin and Altschul, Proc. Natl. Acad. Sci. USA 90:5873-77, 1993. Such algorithms are incorporated into the NBLAST and XBLAST programs (version 2.0) of Altschul et al., J. Mol. Biol. 215:403-10, 1990. BLAST protein searches can be performed with the XBLAST program, score=50, word length=3, to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used. When a percent identity is stated, or a range thereof (e.g., at least, more than, etc.), unless otherwise specified, the endpoints shall be inclusive and the range (e.g., at least 70% identity) shall include all ranges within the cited range.

The input deoxyribonucleic acid (DNA) serves as a nucleic acid template for RNA polymerase. A DNA template may include a polynucleotide encoding a polypeptide of interest (e.g., an antigenic polypeptide). A DNA template, in some embodiments, includes an RNA polymerase promoter (e.g., a T7 RNA polymerase promoter) located 5' from and operably linked to polynucleotide encoding a polypeptide of interest. A DNA template may also include a nucleotide sequence encoding a polyadenylation (polyA) region located at the 3' end of the gene of interest. In some embodiments, an input DNA comprises plasmid DNA (pDNA). As used herein, "plasmid DNA" or "pDNA" refers to an extrachromosomal DNA molecule that is physically separated from chromosomal DNA in a cell and can replicate independently. In some embodiments, plasmid DNA is isolated from a cell (e.g., as a plasmid DNA preparation). In some embodiments, plasmid DNA comprises an origin of replication, which may contain one or more heterologous nucleic acids, for example nucleic acids encoding therapeutic proteins that may serve as a template for RNA polymerase. Plasmid DNA may be circularized or linear (e.g., plasmid DNA that has been linearized by a restriction enzyme digest).

Some embodiments comprise performing a co-IVT reaction that includes multiple input DNAs (or populations of input DNAs). In some embodiments, each input DNA (e.g., population of input DNA molecules) in a co-IVT reaction is obtained from a different source (e.g., synthesized separately, for example in different cells or populations of cells). In some embodiments, each input DNA (e.g., population of input DNA) is obtained from a different bacterial cell or population of bacterial cells. For example, in a co-IVT reaction having three populations of input DNAs, the first input DNA is produced in bacterial cell population A, the second input DNA is produced in bacterial cell population B, and the third input DNA is produced in bacterial population C, where each of A, B, and C are not the same bacterial culture (e.g., co-cultured in the same container or plate). In another example, two input DNAs obtained from different sources are i) chemically synthesized in separate synthesis reactions, or ii) produced by separate amplification (e.g., polymerase chain reactions (PCR reactions)). An RNA transcript, in some embodiments, is the product of an IVT reaction. An RNA transcript, in some embodiments, is a messenger RNA (mRNA) that includes a nucleotide sequence encoding a polypeptide of interest (e.g., a therapeutic protein or therapeutic peptide) linked to a polyA tail. In some embodiments, the mRNA is modified mRNA (mmRNA), which includes at least one modified nucleotide. In some embodiments, an RNA transcript produced by IVT is further modified by circularization, in which two non-adjacent nucleotides (e.g., 5' and 3' terminal nucleotides) of a linear RNA are ligated to produce a circular RNA with no terminal nucleotides.

The nucleoside triphosphates (NTPs) may comprise unmodified or modified ATP, modified or unmodified UTP, modified or unmodified GTP, and/or modified or unmodified CTP. In some embodiments, NTPs of an IVT reaction comprise unmodified ATP. In some embodiments, NTPs of an IVT reaction comprise modified ATP. In some embodiments, NTPs of an IVT reaction comprise unmodified UTP. In some embodiments, NTPs of an IVT reaction comprise modified UTP. In some embodiments, NTPs of an IVT reaction comprise unmodified GTP. In some embodiments, NTPs of an IVT reaction comprise modified GTP. In some embodiments, NTPs of an IVT reaction comprise unmodified CTP. In some embodiments, NTPs of an IVT reaction comprise modified CTP.

The composition of NTPs in an IVT reaction may also vary. In some embodiments, each NTP in an IVT reaction is present in an equimolar amount. In some embodiments, each NTP in an IVT reaction is present in non-equimolar amounts. For example, ATP may be used in excess of GTP, CTP and UTP. As a non-limiting example, an IVT reaction may include 7.5 millimolar GTP, 7.5 millimolar CTP, 7.5 millimolar UTP, and 3.75 millimolar ATP. In some embodiments, the molar ratio of G:C:U:A is 2:1:0.5:1. In some embodiments, the molar ratio of G:C:U:A is 1:1:0.7:1. In some embodiments, the molar ratio of G:C:A:U is 1:1:1:1. The same IVT reaction may include 3.75 millimolar cap analog (e.g., trinucleotide cap or tetranucleotide cap). In some embodiments, the molar ratio of the cap to any of G, C, U, or A is 1:1. In some embodiments, the molar ratio of G:C:U:A:cap is 1:1:1:0.5:0.5. In some embodiments, the molar ratio of G:C:U:A:cap is 1:1:0.5:1:0.5. In some embodiments, the molar ratio of G:C:U:A:cap is 1:0.5:1:1:0.5. In some embodiments, the molar ratio of G:C:U:A:cap is 0.5:1:1:1:0.5. In some embodiments, the amount of NTPs in a IVT reaction is calculated empirically. For example, the rate of consumption for each NTP in an IVT reaction may be empirically determined for each individual input DNA, and then balanced ratios of NTPs based on those individual NTP consumption rates may be added to a IVT comprising multiple of the input DNAs.

In some embodiments, the IVT reaction mixture comprises one or more modified nucleoside triphosphates. In some embodiments, the IVT reaction mixture comprises one or more modified nucleoside triphosphates selected from the group consisting of N6-methyladenosine triphosphate, pseudouridine (ψ) triphosphate, 1-methylpseudouridine ($m^1\psi$) triphosphate, 5-methoxyuridine ($mo^5U$) triphosphate, 5-methylcytidine ($m^5C$) triphosphate, α-thio-guanosine triphosphate, and α-thio-adenosine triphosphate. In some embodiments, the IVT reaction mixture comprises N6-methyladenosine triphosphate. In some embodiments, the IVT reaction mixture comprises pseudouridine triphosphate. In some embodiments, the IVT reaction mixture comprises 1-methylpseudouridine triphosphate. In some embodiments, the concentration of modified nucleoside triphosphates in the reaction mixture is about 0.1% to about 100%, about 0.5% to about 75%, about 1% to about 50%, or about 2% to about 25%. In some embodiments, the concentration of modified nucleoside triphosphates is about 1%, about 2%, about 3%, about 4%, about 5%, about 6%, about 7%, about 8%, about 9%, about 10%, about 15%, about 20%, or about 25%.

In some embodiments, an RNA transcript (e.g., mRNA transcript) includes a modified nucleobase selected from pseudouridine (ψ), 1-methylpseudouridine ($m^1ψ$), 5-methoxyuridine ($mo^5U$), 5-methylcytidine ($m^5C$), α-thio-guanosine and α-thio-adenosine. In some embodiments, an RNA transcript (e.g., mRNA transcript) includes a combination of at least two (e.g., 2, 3, 4 or more) of the foregoing modified nucleobases.

In some embodiments, an RNA transcript (e.g., mRNA transcript) includes pseudouridine (ψ). In some embodiments, an RNA transcript (e.g., mRNA transcript) includes 1-methylpseudouridine ($m^1ψ$). In some embodiments, an RNA transcript (e.g., mRNA transcript) includes 5-methoxyuridine ($mo^5U$). In some embodiments, an RNA transcript (e.g., mRNA transcript) includes 5-methylcytidine ($m^5C$). In some embodiments, an RNA transcript (e.g., mRNA transcript) includes α-thio-guanosine. In some embodiments, an RNA transcript (e.g., mRNA transcript) includes α-thio-adenosine.

In some embodiments, the polynucleotide (e.g., RNA polynucleotide, such as mRNA polynucleotide) is uniformly modified (e.g., fully modified, modified throughout the entire sequence) for a particular modification. For example, a polynucleotide can be uniformly modified with 1-methylpseudouridine ($m^1ψ$), meaning that all uridine residues in the mRNA sequence are replaced with 1-methylpseudouridine ($m^1ψ$). Similarly, a polynucleotide can be uniformly modified for any type of nucleoside residue present in the sequence by replacement with a modified residue such as any of those set forth above. Alternatively, the polynucleotide (e.g., RNA polynucleotide, such as mRNA polynucleotide) may not be uniformly modified (e.g., partially modified, part of the sequence is modified). Each possibility represents a separate embodiment. In some embodiments, modified nucleotides are included in an IVT mixture, and are incorporated randomly during transcription, such that the RNA contains a mixture of modified nucleotides and unmodified nucleotides.

The buffer system of an IVT reaction mixture may vary. In some embodiments, the buffer system contains Tris. The concentration of tris used in an IVT reaction, for example, may be at least 10 mM, at least 20 mM, at least 30 mM, at least 40 mM, at least 50 mM, at least 60 mM, at least 70 mM, at least 80 mM, at least 90 mM, at least 100 mM or at least 110 mM phosphate. In some embodiments, the concentration of phosphate is 20-60 mM or 10-100 mM. In some embodiments, the buffer system contains dithiothreitol (DTT). The concentration of DTT used in an IVT reaction, for example, may be at least 1 mM, at least 5 mM, or at least 50 mM. In some embodiments, the concentration of DTT used in an IVT reaction is 1-50 mM or 5-50 mM. In some embodiments, the concentration of DTT used in an IVT reaction is 5 mM. In some embodiments, the buffer system contains magnesium. In some embodiments, the molar ratio of NTP to magnesium ions ($Mg^{2+}$; e.g., $MgCl_2$) present in an IVT reaction is 1:1 to 1:5. For example, the molar ratio of NTP to magnesium ions may be 1:0.25, 1:0.5, 1:1, 1:2, 1:3, 1:4 or 1:5.

In some embodiments, the molar ratio of NTP to magnesium ions ($Mg^{2+}$; e.g., $MgCl_2$) present in an IVT reaction is 1:1 to 1:5. For example, the molar ratio of NTP to magnesium ions may be 1:1, 1:2, 1:3, 1:4 or 1:5.

In some embodiments, the buffer system contains Tris-HCl, spermidine (e.g., at a concentration of 1-30 mM), TRITON® X-100 (polyethylene glycol p-(1,1,3,3-tetramethylbutyl)-phenyl ether) and/or polyethylene glycol (PEG).

In some embodiments, IVT methods further comprise a step of separating (e.g., purifying) in vitro transcription products (e.g., mRNA) from other reaction components. In some embodiments, the separating comprises performing chromatography on the IVT reaction mixture. In some embodiments, the method comprises reverse phase chromatography. In some embodiments, the method comprises reverse phase column chromatography. In some embodiments, the chromatography comprises size-based (e.g., length-based) chromatography. In some embodiments, the method comprises size exclusion chromatography. In some embodiments, the chromatography comprises oligo-dT chromatography.

Untranslated Regions

Untranslated regions (UTRs) are sections of a nucleic acid before a start codon (5' UTR) and after a stop codon (3' UTR) that are not translated. In some embodiments, a nucleic acid (e.g., a ribonucleic acid (RNA), e.g., a messenger RNA (mRNA)) of the disclosure comprising an open reading frame (ORF) encoding one or more proteins or peptides further comprises one or more UTR (e.g., a 5' UTR or functional fragment thereof, a 3' UTR or functional fragment thereof, or a combination thereof).

A UTR can be homologous or heterologous to the coding region in a nucleic acid. In some embodiments, the UTR is homologous to the ORF encoding the one or more peptide epitopes. In some embodiments, the UTR is heterologous to the ORF encoding the one or more peptide epitopes. In some embodiments, the nucleic acid comprises two or more 5' UTRs or functional fragments thereof, each of which have the same or different nucleotide sequences. In some embodiments, the nucleic acid comprises two or more 3' UTRs or functional fragments thereof, each of which have the same or different nucleotide sequences.

In some embodiments, the 5' UTR or functional fragment thereof, 3' UTR or functional fragment thereof, or any combination thereof is sequence optimized.

In some embodiments, the 5' UTR or functional fragment thereof, 3' UTR or functional fragment thereof, or any combination thereof comprises at least one chemically modified nucleobase, e.g., 5-methoxyuracil.

UTRs can have features that provide a regulatory role, e.g., increased or decreased stability, localization, and/or translation efficiency. A nucleic acid comprising a UTR can be administered to a cell, tissue, or organism, and one or more regulatory features can be measured using routine methods. In some embodiments, a functional fragment of a 5' UTR or 3' UTR comprises one or more regulatory features of a full length 5' or 3' UTR, respectively.

Natural 5' UTRs bear features that play roles in translation initiation. They harbor signatures like Kozak sequences that are commonly known to be involved in the process by which the ribosome initiates translation of many genes. 5' UTRs also have been known to form secondary structures that are involved in elongation factor binding.

By engineering the features typically found in abundantly expressed genes of specific target organs, one can enhance the stability and protein production of a nucleic acid. For example, introduction of 5' UTR of liver-expressed mRNA, such as albumin, serum amyloid A, Apolipoprotein A/B/E, transferrin, alpha fetoprotein, erythropoietin, or Factor VIII, can enhance expression of nucleic acids in hepatic cell lines or liver. Likewise, use of 5' UTRs from other tissue-specific mRNA to improve expression in that tissue is possible for muscle (e.g., MyoD, Myosin, Myoglobin, Myogenin, Herculin), for endothelial cells (e.g., Tie-1, CD36), for myeloid cells (e.g., C/EBP, AML1, G-CSF, GM-CSF, CD11b, MSR, Fr-1, i-NOS), for leukocytes (e.g., CD45, CD18), for adipose tissue (e.g., CD36, GLUT4, ACRP30, adiponectin), and for lung epithelial cells (e.g., SP-A/B/C/D).

In some embodiments, UTRs are selected from a family of transcripts whose proteins share a common function, structure, feature, or property. For example, an encoded polypeptide can belong to a family of proteins (i.e., that share at least one function, structure, feature, localization, origin, or expression pattern), which are expressed in a particular cell, tissue or at some time during development. The UTRs from any of the genes or mRNA can be swapped for any other UTR of the same or different family of proteins to create a new nucleic acid. In some embodiments, the 5' UTR and the 3' UTR can be heterologous. In some embodiments, the 5' UTR can be derived from a different species than the 3' UTR. In some embodiments, the 3' UTR can be derived from a different species than the 5' UTR.

International Patent Application No. PCT/US2014/021522 (Publ. No. WO/2014/164253) provides a listing of exemplary UTRs that may be utilized in the nucleic acids of the present disclosure as flanking regions to an ORF. This publication is incorporated by reference herein for this purpose.

Additional exemplary UTRs that may be utilized in the nucleic acids of the present disclosure include, but are not limited to, one or more 5' UTRs and/or 3' UTRs derived from the nucleic acid sequence of: a globin, such as an α- or β-globin (e.g., a *Xenopus*, mouse, rabbit, or human globin); a strong Kozak translational initiation signal; a CYBA (e.g., human cytochrome b-245 α polypeptide); an albumin (e.g., human albumin7); a HSD17B4 (hydroxysteroid (17-β) dehydrogenase); a virus (e.g., a tobacco etch virus (TEV), a Venezuelan equine encephalitis virus (VEEV), a Dengue virus, a cytomegalovirus (CMV; e.g., CMV immediate early 1 (IE1)), a hepatitis virus (e.g., hepatitis B virus), a sindbis virus, or a PAV barley yellow dwarf virus); a heat shock protein (e.g., hsp70); a translation initiation factor (e.g., elF4G); a glucose transporter (e.g., hGLUT1 (human glucose transporter 1)); an actin (e.g., human α or β actin); a GAPDH; a tubulin; a histone; a citric acid cycle enzyme; a topoisomerase (e.g., a 5' UTR of a TOP gene lacking the 5' TOP motif (the oligopyrimidine tract)); a ribosomal protein Large 32 (L32); a ribosomal protein (e.g., human or mouse ribosomal protein, such as, for example, rps9); an ATP synthase (e.g., ATP5A1 or the β subunit of mitochondrial $H^+$-ATP synthase); a growth hormone (e.g., bovine (bGH) or human (hGH)); an elongation factor (e.g., elongation factor 1 α1 (EEF1A1)); a manganese superoxide dismutase (MnSOD); a myocyte enhancer factor 2A (MEF2A); a β-F1-ATPase, a creatine kinase, a myoglobin, a granulocyte-colony stimulating factor (G-CSF); a collagen (e.g., collagen type I, alpha 2 (CollA2), collagen type I, alpha 1 (CollA1), collagen type VI, alpha 2 (Col6A2), collagen type VI, alpha 1 (Col6A1)); a ribophorin (e.g., ribophorin I (RPNI)); a low density lipoprotein receptor-related protein (e.g., LRP1); a cardiotrophin-like cytokine factor (e.g., Nnt1); calreticulin (Calr); a procollagen-lysine, 2-oxoglutarate 5-dioxygenase 1 (Plod1); and a nucleobindin (e.g., Nucb1).

In some embodiments, the 5' UTR is selected from the group consisting of a β-globin 5' UTR; a 5' UTR containing a strong Kozak translational initiation signal; a cytochrome b-245 α polypeptide (CYBA) 5' UTR; a hydroxysteroid (17-β) dehydrogenase (HSD17B4) 5' UTR; a Tobacco etch virus (TEV) 5' UTR; a Venezuelen equine encephalitis virus (TEEV) 5' UTR; a 5' proximal open reading frame of rubella virus (RV) RNA encoding nonstructural proteins; a Dengue virus (DEN) 5' UTR; a heat shock protein 70 (Hsp70) 5' UTR; a eIF4G 5' UTR; a GLUT1 5' UTR; functional fragments thereof and any combination thereof.

In some embodiments, the 3' UTR is selected from the group consisting of a β-globin 3' UTR; a CYBA 3' UTR; an albumin 3' UTR; a growth hormone (GH) 3' UTR; a VEEV 3' UTR; a hepatitis B virus (HBV) 3' UTR; α-globin 3' UTR; a DEN 3' UTR; a PAV barley yellow dwarf virus (BYDV-PAV) 3' UTR; an elongation factor 1 α1 (EEF1A1) 3' UTR; a manganese superoxide dismutase (MnSOD) 3' UTR; a β subunit of mitochondrial H(+)-ATP synthase (β-mRNA) 3' UTR; a GLUT1 3' UTR; a MEF2A 3' UTR; a β-F1-ATPase 3' UTR; functional fragments thereof and combinations thereof.

Wild-type UTRs derived from any gene or mRNA can be incorporated into the nucleic acids of the disclosure. In some embodiments, a UTR can be altered relative to a wild type or native UTR to produce a variant UTR, e.g., by changing the orientation or location of the UTR relative to the ORF; or by inclusion of additional nucleotides, deletion of nucleotides, swapping or transposition of nucleotides. In some embodiments, variants of 5' or 3' UTRs can be utilized, for example, mutants of wild type UTRs, or variants wherein one or more nucleotides are added to or removed from a terminus of the UTR.

Additionally, one or more synthetic UTRs can be used in combination with one or more non-synthetic UTRs. See, e.g., Mandal and Rossi, *Nat. Protoc.* 2013 8(3):568-82, and sequences available at www.addgene.org, the contents of each are incorporated herein by reference in their entirety. UTRs or portions thereof can be placed in the same orientation as in the transcript from which they were selected or can be altered in orientation or location. Hence, a 5' and/or 3' UTR can be inverted, shortened, lengthened, or combined with one or more other 5' UTRs or 3' UTRs.

In some embodiments, the nucleic acid may comprise multiple UTRs, e.g., a double, a triple or a quadruple 5' UTR or 3' UTR. For example, a double UTR comprises two copies of the same UTR either in series or substantially in series. For example, a double beta-globin 3' UTR can be used (see, for example, US2010/0129877, the contents of which are incorporated herein by reference for this purpose).

The nucleic acids of the disclosure can comprise combinations of features. For example, the ORF can be flanked by a 5' UTR that comprises a strong Kozak translational initiation signal and/or a 3' UTR comprising an oligo(dT) sequence for templated addition of a polyA tail. A 5' UTR can comprise a first nucleic acid fragment and a second nucleic acid fragment from the same and/or different UTRs (see, e.g., US2010/0293625, herein incorporated by reference in its entirety for this purpose).

Other non-UTR sequences can be used as regions or subregions within the nucleic acids of the disclosure. For example, introns or portions of intron sequences can be incorporated into the nucleic acids of the disclosure. Incorporation of intronic sequences can increase protein production as well as nucleic acid expression levels. In some embodiments, the nucleic acid of the disclosure comprises an internal ribosome entry site (IRES) instead of or in addition to a UTR (see, e.g., Yakubov et al., Biochem. Biophys. Res. Commun. 2010 394(1):189-193, the contents of which are incorporated herein by reference in their entirety). In some embodiments, the nucleic acid comprises an IRES instead of a 5' UTR sequence. In some embodiments, the nucleic acid comprises an IRES that is located between a 5' UTR and an open reading frame. In some embodiments, the nucleic acid comprises an ORF encoding a viral capsid sequence. In some embodiments, the nucleic acid comprises a synthetic 5' UTR in combination with a non-synthetic 3' UTR.

In some embodiments, the UTR can also include at least one translation enhancer nucleic acid, translation enhancer element, or translational enhancer elements (collectively, "TEE," which refers to nucleic acid sequences that increase the amount of polypeptide or protein produced from a polynucleotide. As a non-limiting example, the TEE can include those described in US2009/0226470, incorporated herein by reference in its entirety for this purpose, and others known in the art. As a non-limiting example, the TEE can be located between the transcription promoter and the start codon. In some embodiments, the 5' UTR comprises a TEE. In one aspect, a TEE is a conserved element in a UTR that can promote translational activity of a nucleic acid such as, but not limited to, cap-dependent or cap-independent translation. In one non-limiting example, the TEE comprises the TEE sequence in the 5'-leader of the Gtx homeodomain protein. See, e.g., Chappell et al., *PNAS*. 2004. 101:9590-9594, incorporated herein by reference in its entirety for this purpose.

Poly(A) Tails

Aspects of the present disclosure relate to methods of producing RNAs containing one or more polyA tails. A "polyA tail" is a region of mRNA that is downstream, e.g., directly downstream (i.e., 3'), from the open reading frame and/or the 3' UTR that contains multiple, consecutive adenosine monophosphates. A polyA tail may contain 10 to 300 adenosine monophosphates. For example, a polyA tail may contain 10, 20, 30, 40, 50, 60, 70, 80, 90, 100, 110, 120, 130, 140, 150, 160, 170, 180, 190, 200, 210, 220, 230, 240, 250, 260, 270, 280, 290 or 300 adenosine monophosphates. In some embodiments, a polyA tail contains 50 to 250 adenosine monophosphates. In a relevant biological setting (e.g., in cells, in vivo, etc.) the poly(A) tail functions to protect mRNA from enzymatic degradation, e.g., in the cytoplasm, and aids in transcription termination, export of the mRNA from the nucleus, and translation.

As used herein, "polyA-tailing efficiency" refers to the amount (e.g., expressed as a percentage) of mRNAs having polyA tail that are produced by an IVT reaction using an input DNA relative to the total number of mRNAs produced in the IVT reaction using the input DNA. The polyA-tailing efficiency of an IVT reaction may vary, for example depending upon the RNA polymerase used, amount or purity of input DNA used, etc. In some embodiments, the polyA-tailing efficiency of an IVT reaction is greater than 85%, 90%, 95%, or 99.9%. Methods of calculating polyA-tailing efficiency are known, for example by determining the amount of polyA tail-containing mRNA relative to total mRNA produced in an IVT reaction by column chromatography (e.g., oligo-dT chromatography).

In some embodiments, at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 99.9% of RNAs in an RNA composition produced by a method described herein comprise a polyA tail. In some embodiments, at least 85%, 86%, 87%, 88%, 89%, 90%, 91%, 92%, 93%, 94%, 95%, 96%, 97%, 98%, 99%, or 99.9% of each RNA in an RNA composition produced by a method described herein comprise a polyA tail. The efficiency (e.g., percentage of polyA tail-containing RNAs in an RNA composition may be measured i) after the IVT reaction and before purification, or ii) after the RNA composition has been purified (e.g., by chromatography, such as oligo-dT chromatography).

Unique polyA tail lengths provide certain advantages to the nucleic acids of the present disclosure. Generally, the length of a polyA tail, when present, is greater than 30 nucleotides in length. In another embodiment, the polyA tail is greater than 35 nucleotides in length (e.g., at least or greater than about 15, 20, 25, 30, 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, or 3,000 nucleotides).

In some embodiments, the polyA tail is designed relative to the length of the overall nucleic acid or the length of a particular region of the nucleic acid. This design can be based on the length of a coding region, the length of a particular feature or region or based on the length of the ultimate product expressed from the nucleic acids.

In this context, the polyA tail can be 10, 20, 30, 40, 50, 60, 70, 80, 90, or 100% greater in length than the nucleic acid or feature thereof. The polyA tail can also be designed as a fraction of the nucleic acid to which it belongs. In this context, the polyA tail can be 10, 20, 30, 40, 50, 60, 70, 80, or 90% or more of the total length of the construct, a construct region or the total length of the construct minus the polyA tail. Further, engineered binding sites and conjugation of nucleic acids for PolyA-binding protein can enhance expression.

mRNA Compositions

Some aspects of the present disclosure provide compositions comprising RNA produced by any of the methods described herein. In some embodiments, the concentration of proteins in the RNA composition produced by the method is 0.8% (% w/w) or less, 0.6% or less, 0.4% or less, or 0.2% or less. Methods of measuring the amount of protein in a sample include colorimetric assays (e.g., Bradford assay), spectroscopy, ELISA, polyacrylamide gel electrophoresis electropherogram analysis, and chromatographic analysis. See, e.g., Sapan et al. *Biotechnol Appl Biochem*. 1999. 29(2):99-108. In some embodiments, the concentration of proteins in the RNA composition is 0.8% or less. In some embodiments, the concentration of proteins in the RNA composition is 0.6% or less. In some embodiments, the concentration of proteins in the RNA composition is 0.5% or less. In some embodiments, the concentration of proteins in the RNA composition is 0.4% or less. In some embodiments, the concentration of proteins in the RNA composition is 0.3% or less. In some embodiments, the concentration of proteins in the RNA composition is 0.2% or less.

In some embodiments, the RNA of any of the compositions described herein is an mRNA. In some embodiments, at least 50%, at least 60%, at least 70%, at least 75%, at least 80%, at least 85%, or at least 90% of the mRNA molecules of the RNA composition comprise a poly(A) tail. Methods of determining the frequency of mRNAs that comprise poly(A) tails include qRT-PCR-based methods and chromatographic methods. For example, a composition comprising mRNAs may be analyzed by high performance liquid chromatography (HPLC), which will yield a peak corresponding to untailed RNAs, and a peak corresponding to tailed RNAs. The relative heights of the peaks may be compared to determine the relative amount of tailed and untailed RNAs in the composition. In some embodiments, at least 50% of the mRNA molecules comprise a poly(A) tail.

In some embodiments, at least 60% of the mRNA molecules comprise a poly(A) tail. In some embodiments, at least 70% of the mRNA molecules comprise a poly(A) tail. In some embodiments, at least 80% of the mRNA molecules comprise a poly(A) tail. In some embodiments, at least 90% of the mRNA molecules comprise a poly(A) tail.

In some embodiments of the compositions described herein, the RNA is formulated in a lipid nanoparticle. Lipid nanoparticles typically comprise amino lipid, non-cationic lipid, structural lipid, and PEG lipid components along with the nucleic acid cargo of interest. The lipid nanoparticles can be generated using components, compositions, and methods as are generally known in the art, see for example PCT/US2016/052352; PCT/US2016/068300; PCT/US2017/037551; PCT/US2015/027400; PCT/US2016/047406; PCT/US2016/000129; PCT/US2016/014280; PCT/US2017/038426; PCT/US2014/027077; PCT/US2014/055394; PCT/US2016/052117; PCT/US2012/069610; PCT/US2017/027492; PCT/US2016/059575; PCT/US2016/069491; PCT/US2016/069493; and PCT/US2014/066242, all of which are incorporated by reference herein in their entirety.

In some embodiments, the lipid nanoparticle comprises an ionizable amino lipid. In some embodiments, the lipid nanoparticle further comprises: a non-cationic lipid; a sterol; and a polyethylene glycol (PEG)-modified lipid. In some embodiments, the lipid nanoparticle comprises: 40-55 mol % ionizable amino lipid; 5-15 mol % non-cationic lipid; 35-45 mol % sterol; and 1-5 mol % PEG-modified lipid.

In some aspects, the present disclosure relates to a composition comprising mRNA formulated in a lipid nanoparticle, wherein a concentration of proteins in the mRNA prior to formulation in the lipid nanoparticle is 0.8% (% w/w) or less, 0.6% or less, 0.4% or less, or 0.2% or less, and wherein at least 50%, at least 60%, at least 70%, at least 75%, at least 80%, at least 85%, or at least 90% of the mRNA molecules of the mRNA composition comprise a poly(A) tail.

EXAMPLES

Example 1: Multicolumn Chromatography

In vitro-transcribed mRNA was purified using a multicolumn continuous chromatography (MCC) approach. In contrast to batch chromatography, which uses a single, larger column, MCC uses multiple columns connected in series, allowing any mRNA not captured by the first column (breakthrough) to be loaded onto a second column, preventing loss of breakthrough mRNA that would otherwise occur in batch chromatography-based methods. An additional advantage of MCC methods is that they increase the amount of time that mRNA spends in a "mass transfer zone" where oligo-dT resin is not already saturated with bound mRNA, and thus increase the rate at which mRNA is actively captured by oligo-dT resin, rather than passing over saturated oligo-dT. Furthermore, as resin in the mass transfer zone becomes saturated, bound mRNA is eluted from a column, with the column being eluted and moved to the end of the series of columns, so that it may later capture additional mRNA.

Figure 2A:
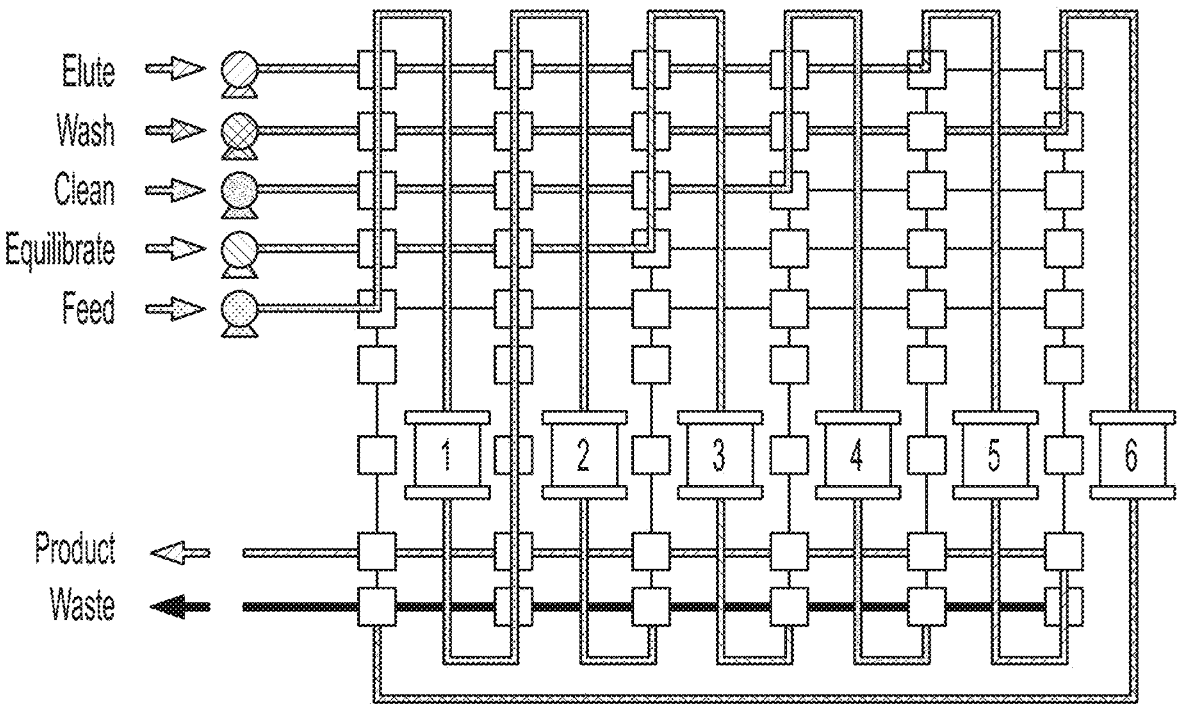
FIGS. 2A-2B show an apparatus for performing multi-column chromatography of mRNA and its mode of operation.

Multicolumn chromatography was performed using a machine that holds multiple columns, each of which is capable of receiving input from one of multiple sources, and directing output to into another column or output channel. An autonomous switch system controlled the inputs and outputs of each column. Two columns, 1 and 2, were previously washed with equilibration buffer, after which an input feed containing in vitro-transcribed mRNA was passed through column 1. Flowthrough from column 1 was directed into column 2, so that any mRNA not captured by column 1 would pass through column 2 rather than being lost (FIG. 2A). Meanwhile, column 3 was washed with equilibration buffer to prepare it for mRNA capture. Column 4, from which mRNA had previously been eluted, was cleaned to rejuvenate its ability to capture mRNA. Elution buffer was passed through column 5 to elute bound mRNA, which was directed into a "product" collection channel. Column 6, which had been saturated with mRNA, was washed to remove impurities.

Figure 2B:
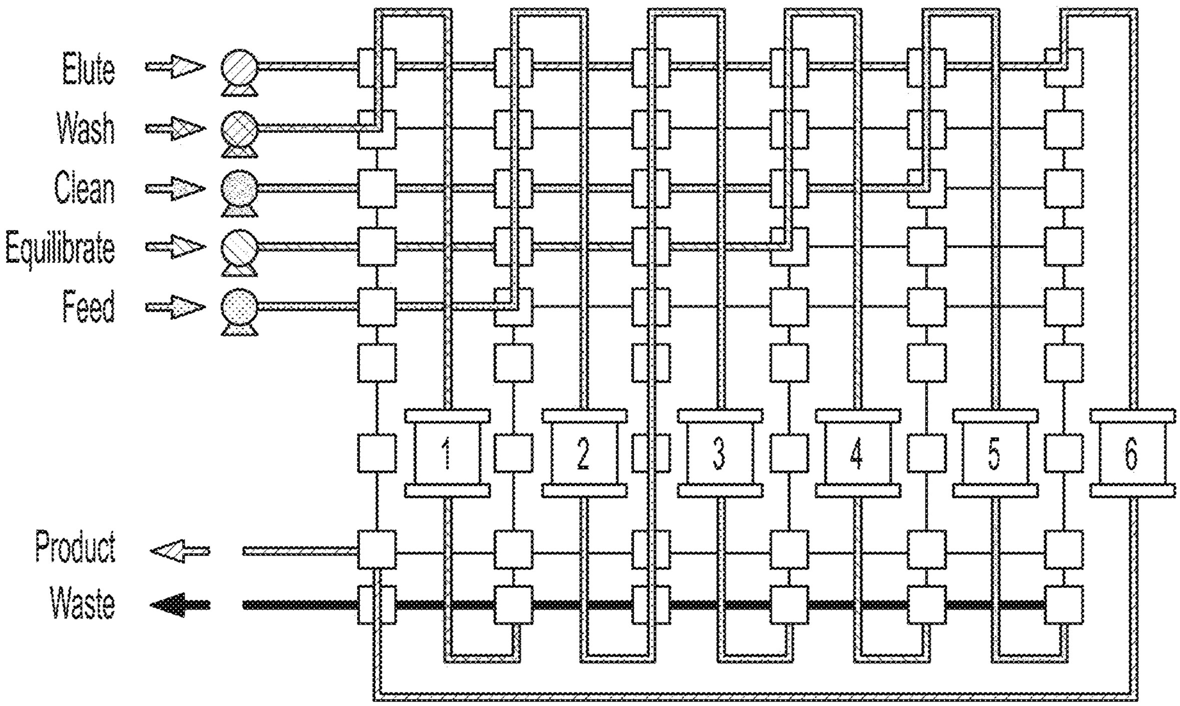

In the next step, after column 1 had been saturated with mRNA, the feed containing mRNA was redirected into column 2, and the output of column 2 was directed into equilibrated column 3 (FIG. 2B). Column 1, which had become saturated with mRNA, was washed to remove impurities. Column 4, which had recently been cleaned, was equilibrated to prepare it to capture mRNA. Column 5, from which mRNA had recently been eluted, was cleaned to rejuvenate its mRNA-binding capacity. Column 6, which had recently been washed to remove impurities from bound mRNA, was rinsed with elution buffer to elute bound mRNA, which was directed into a collection channel. This cycle was repeated until all of the input mRNA had been passed through the columns. Except for the first column to receive mRNA feed solution directly at the start of the process, this cycle comprised subjecting each column to the following steps, in order:

(i) Equilibration buffer ("Equilibrate")
(ii) Flowthrough of previous column, containing breakthrough mRNA
(iii) mRNA feed ("Feed")
(iv) Wash buffer ("Wash")
(v) Elution buffer ("Elute")
(vi) Cleaning buffer ("Clean")

After the "Clean" step, the column was moved to the last position in the series and equilibrated, beginning the cycle again. This cycle was repeated until all of the feed solution containing mRNA had been exhausted, and elution steps had been completed from all columns after the exhaustion of mRNA feed solution. An exemplary overview of this process, starting with the initial preparation steps and using six columns, is given in Table 1.

TABLE 1

Overview of 6-column multicolumn chromatography process.

| Step of MCC process (Cycle.Step) | Column 1 | Column 2 | Column 3 | Column 4 | Column 5 | Column 6 |
|---|---|---|---|---|---|---|
| Preparation | Equilibrating solution | Equilibrating solution | Cleaning solution | Eluting solution | Washing solution | Storage solution |
| 1.1 | Feed solution of mRNA | Column 1 flowthrough | Equilibrating solution | Cleaning solution | Eluting solution | Washing solution |

TABLE 1-continued

Overview of 6-column multicolumn chromatography process.

| Step of MCC process (Cycle.Step) | Column 1 | Column 2 | Column 3 | Column 4 | Column 5 | Column 6 |
|---|---|---|---|---|---|---|
| 1.2 | Washing solution | Feed solution of mRNA | Column 2 flowthrough | Equilibrating solution | Cleaning solution | Eluting solution |
| 1.3 | Eluting solution | Washing solution | Feed solution of mRNA | Column 3 flowthrough | Equilibrating solution | Cleaning solution |
| 1.4 | Cleaning solution | Eluting solution | Washing solution | Feed solution of mRNA | Column 4 flowthrough | Equilibrating solution |
| 1.5 | Equilibrating solution | Cleaning solution | Eluting solution | Washing solution | Feed solution of mRNA | Column 5 flowthrough |
| 1.6 | Column 6 flowthrough | Equilibrating solution | Cleaning solution | Eluting solution | Washing solution | Feed solution of mRNA |
| 2.1 | Feed solution of mRNA | Column 1 flowthrough | Equilibrating solution | Cleaning solution | Eluting solution | Washing solution |
| 2.2 | Washing solution | Feed solution of mRNA | Column 2 flowthrough | Equilibrating solution | Cleaning solution | Eluting solution |
| 2.3 | Eluting solution | Washing solution | Feed solution of mRNA | Column 3 flowthrough | Equilibrating solution | Cleaning solution |
| 2.4 | Cleaning solution | Eluting solution | Washing solution | Feed solution of mRNA | Column 4 flowthrough | Equilibrating solution |
| 2.5 | Equilibrating solution | Cleaning solution | Eluting solution | Washing solution | Feed solution of mRNA | Column 5 flowthrough |
| 2.6 | Column 6 flowthrough | Equilibrating solution | Cleaning solution | Eluting solution | Washing solution | Feed solution of mRNA |
| 3.1 | Feed solution of mRNA | Column 1 flowthrough | Equilibrating solution | Cleaning solution | Eluting solution | Washing solution |
| . . . | Repeat until Feed solution of mRNA exhausted. | | | | | |
| . . . | Wash to remove impurities, and elute mRNA from, any columns that had been contacted with mRNA after their most recent elution step. | | | | | |

Figure 3:
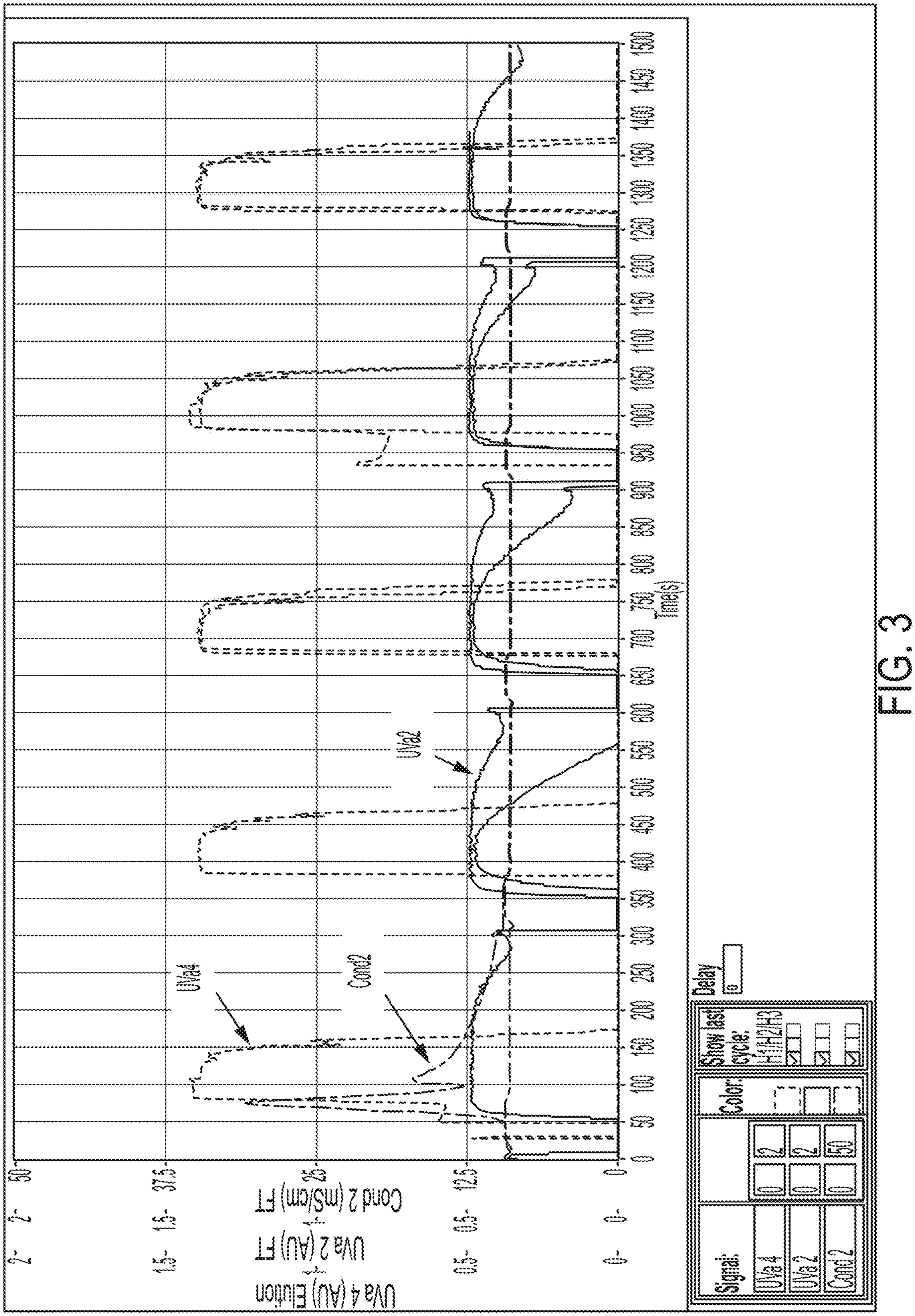
FIG. 3 shows monitoring of UV absorbance of outputs from columns and conductivity of the feed solution throughout a multicolumn chromatography process. Green lines indicate absorbance of outputs that were expected to contain mRNA, yellow lines indicate absorbance of outputs that were expected to contain waste products, and red lines indicate conductivity.
Figure 4A:
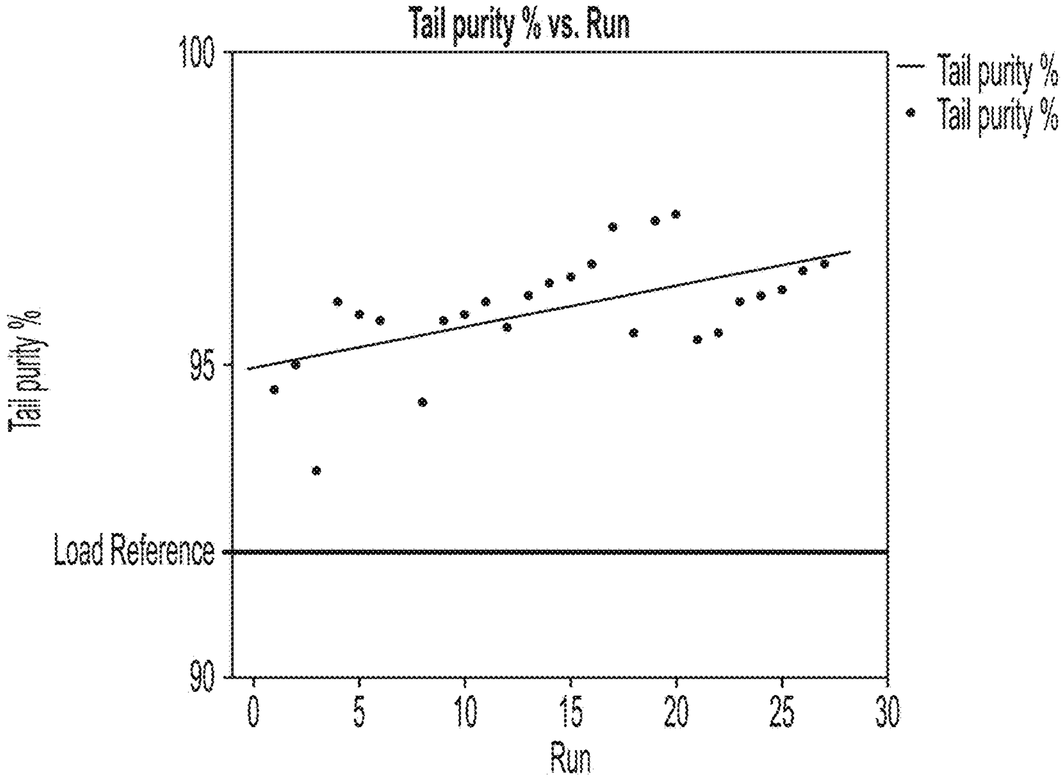
FIGS. 4A-4B show purity analysis of mRNAs collected from successive columns in a multicolumn chromatography process.
Figure 4B:
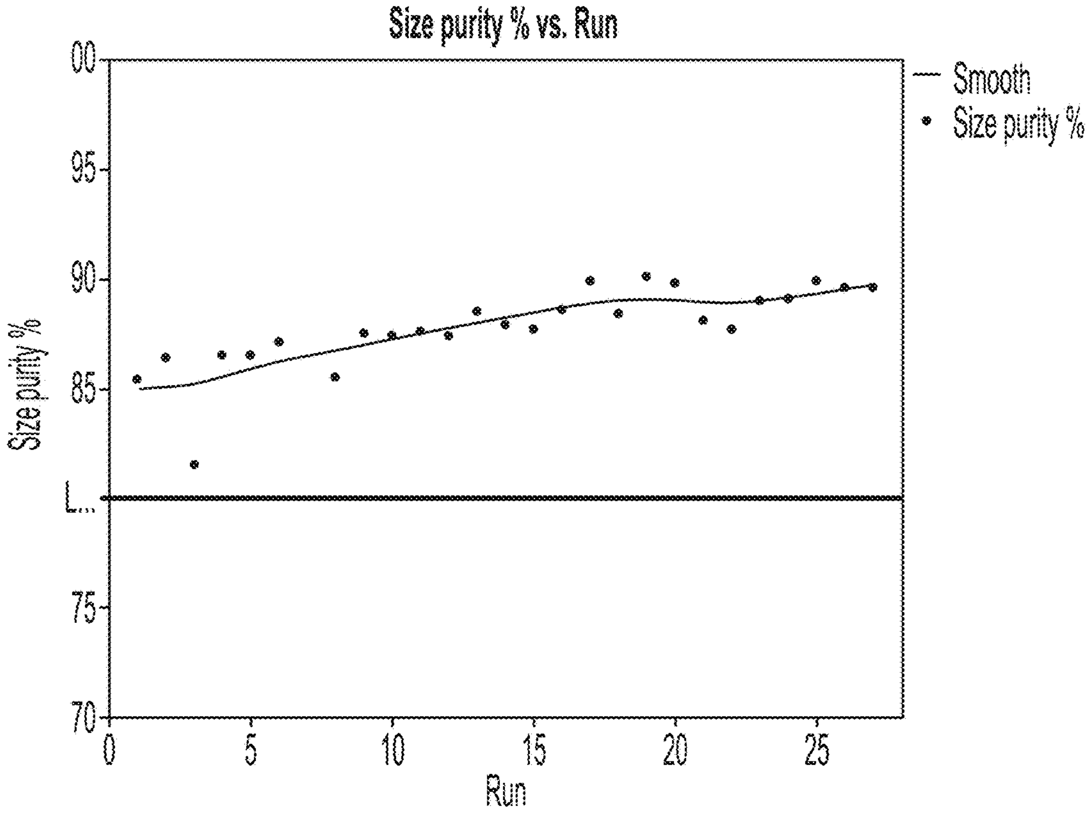

During this process, the UV absorbance of the output from each column was monitored (FIG. 3). Absorbance of output from columns rinsed with elution buffer, which were expected to contain mRNA, was high, indicating successful capture and elution of mRNA. By contrast, absorbance from columns rinsed with wash buffer, which was expected to contain impurities such as proteins, was relatively low, indicating that wash steps resulted in minimal loss of mRNA. Conductivity of the feed solution, which facilitates the linearization of the polyA tail of mRNA for interaction with oligo-dT resin, was monitored, and shown to be maintained at a consistent level. Eluate from each successive elution was analyzed for the percentage of mRNA molecules that contained a polyA tail (tail purity, FIG. 4A), and the percentage of mRNA molecules that were of the expected size (size purity, FIG. 4B). There was a trend towards increasing tail and size purity with each successive elution, indicating that extended MCC processes did not result in a loss of tail or size purity.

Example 2: Productivity Analysis of Multicolumn Chromatography Parameters

The yield, productivity, tail purity, and size purity of the multicolumn chromatography process were modeled as functions of multiple tunable parameters, including: load challenge, the concentration of mRNA added to each column; load residence time, the amount of time the mRNA feed was passed through each column; elution residence time, the amount of time elution buffer was passed through each column; rest step residence time, the amount of time taken to regenerate each column; the number of columns used; and the dimensions of each column. The financial and resource cost, and expected productivity, of batch and multicolumn chromatography processes were modeled as functions of these parameters. The results of these analyses are shown in Table 2. At both large and smaller scales, multicolumn chromatography allows for markedly improved productivities, in terms of mRNA purified for a given amount of resin and time, with significant cost reductions.

TABLE 2

Comparative productivity of batch and multicolumn chromatography processes.

| Process | Batch process (large scale) | Multicolumn process (large scale) | Batch process (test scale) | Multicolumn process (test scale) |
|---|---|---|---|---|
| # Columns | 1 | 5 | 1 | 5 |
| Total dT resin | 40 L | 7.85 L | 3.8 L | 0.49 L |
| Load challenge (mg/mL mRNA) | 2 | 3 | 2 | 3 |
| Productivity ($g \cdot L^{-1} \cdot hr^{-1}$) | 0.73 | 6.10 | 1.62 | 6.80 |
| Relative cost ($) | 1 (reference for large scale) | 0.174 | 1 (reference for test scale) | 0.129 |

Example 3: Parallel Loopback Multicolumn Chromatography

In vitro-transcribed mRNA was purified using a multicolumn chromatography approach similar to the process described in Example 1, except that when a first chromatography column was contacted with bulk feed solution containing mRNA, the output of that column was divided and directed in parallel into a second and third chromatography column (FIG. 1). After the first column was substantially saturated with mRNA, the feed solution was applied directly to the second column, and the output of the second column was directed in parallel into the third and a fourth column. After the second column was substantially saturated, the feed solution was applied directly to the third column, and the output of the third column was directed in parallel into the fourth and a fifth column. Therefore, the third column received output from two distinct columns, before the mRNA-containing feed solution was applied directly to it. After a given column was used to bind mRNA from the feed solution, washing, elution, cleaning, and equilibration steps were conducted as described in Example 1. This cycle was repeated until all of the input mRNA had been passed through the columns. Except for the first column to receive mRNA feed solution directly at the start of the process, and the second column that received flow-through from only one other column before receiving feed solution directly, this cycle comprised subjecting each column being subjected to the following steps, in order:

(i) Equilibration buffer ("Equilibrate");

(ii) Flowthrough of a first previous column, containing breakthrough mRNA from feed solution;

(iii) Flowthrough of a second previous column in series, containing breakthrough mRNA from feed solution;

(iv) mRNA feed ("Feed");

(v) Wash buffer ("Wash");

(vi) Elution buffer ("Elute"); and (vii) Cleaning buffer ("Clean").

After the "Clean" step, the column was moved to the last position in the series and equilibrated, beginning the cycle again. This cycle was repeated until all of the feed solution containing mRNA had been exhausted, and, after exhaustion of the mRNA feed solution, completion of elution steps in all columns containing bound mRNA. An exemplary overview of this process, starting with the initial preparation steps and using seven columns, is given in Table 3.

TABLE 3

Overview of 7-column parallel multicolumn chromatography process.

| Step of MCC process (Cycle.Step) | Column 1 | Column 2 | Column 3 | Column 4 | Column 5 | Column 6 | Column 7 |
|---|---|---|---|---|---|---|---|
| Preparation | Equilibrating solution | Equilibrating solution | Equilibrating solution | Cleaning solution | Eluting solution | Washing solution | Storage solution |
| 1.1 | Feed solution of mRNA | Column 1 flowthrough | Column 1 flowthrough | Equilibrating solution | Cleaning solution | Eluting solution | Washing solution |
| 1.2 | Washing solution | Feed solution of mRNA | Column 2 flowthrough | Column 2 flowthrough | Equilibrating solution | Cleaning solution | Eluting solution |
| 1.3 | Eluting solution | Washing solution | Feed solution of mRNA | Column 3 flowthrough | Column 3 flowthrough | Equilibrating solution | Cleaning solution |
| 1.4 | Cleaning solution | Eluting solution | Washing solution | Feed solution of mRNA | Column 4 flowthrough | Column 4 flowthrough | Equilibrating solution |
| 1.5 | Equilibrating solution | Cleaning solution | Eluting solution | Washing solution | Feed solution of mRNA | Column 5 flowthrough | Column 5 flowthrough |
| 1.6 | Column 6 flowthrough | Equilibrating solution | Cleaning solution | Eluting solution | Washing solution | Feed solution of mRNA | Column 6 flowthrough |
| 1.7 | Column 7 flowthrough | Column 7 flowthrough | Equilibrating solution | Cleaning solution | Eluting solution | Washing solution | Feed solution of mRNA |
| 2.1 | Feed solution of mRNA | Column 1 flowthrough | Column 1 flowthrough | Equilibrating solution | Cleaning solution | Eluting solution | Washing solution |
| 2.2 | Washing solution | Feed solution of mRNA | Column 2 flowthrough | Column 2 flowthrough | Equilibrating solution | Cleaning solution | Eluting solution |
| 2.3 | Eluting solution | Washing solution | Feed solution of mRNA | Column 3 flowthrough | Column 3 flowthrough | Equilibrating solution | Cleaning solution |
| 2.4 | Cleaning solution | Eluting solution | Washing solution | Feed solution of mRNA | Column 4 flowthrough | Column 4 flowthrough | Equilibrating solution |
| 2.5 | Equilibrating solution | Cleaning solution | Eluting solution | Washing solution | Feed solution of mRNA | Column 5 flowthrough | Column 5 flowthrough |
| 2.6 | Column 6 flowthrough | Equilibrating solution | Cleaning solution | Eluting solution | Washing solution | Feed solution of mRNA | Column 6 flowthrough |
| 2.7 | Column 7 flowthrough | Column 7 flowthrough | Equilibrating solution | Cleaning solution | Eluting solution | Washing solution | Feed solution of mRNA |
| 3.1 | Feed solution of mRNA | Column 1 flowthrough | Column 1 flowthrough | Equilibrating solution | Cleaning solution | Eluting solution | Washing solution |
| . . . | Repeat until Feed solution of mRNA exhausted. | | | | | | |
| . . . | Wash to remove impurities, and elute mRNA from, any columns that had been contacted with mRNA after their most recent elution step. | | | | | | |

Figure 5:
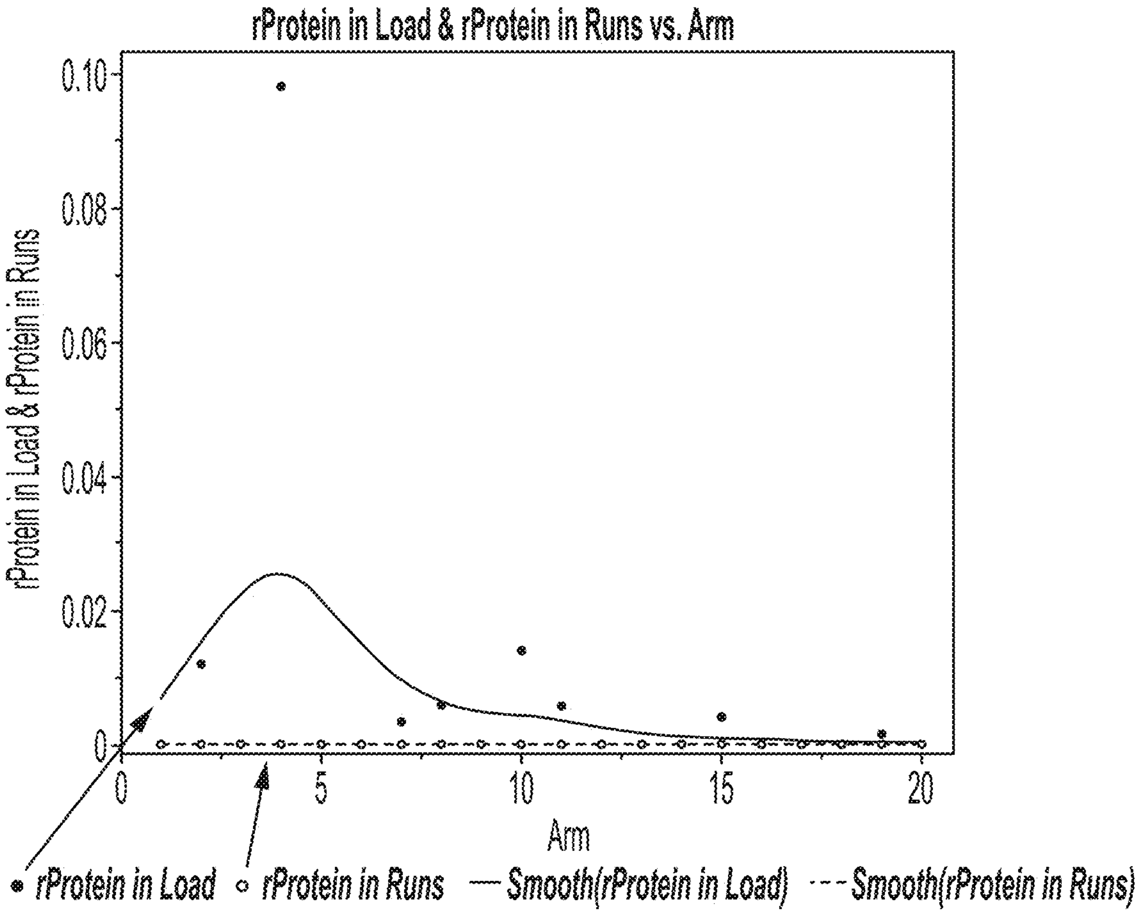
FIG. 5 shows the amount of residual protein (rProtein) present in an mRNA before application to the column (Load) and mRNA that is eluted from columns in successive elutions from a column in a multicolumn chromatography process (Run).
Figure 6A:
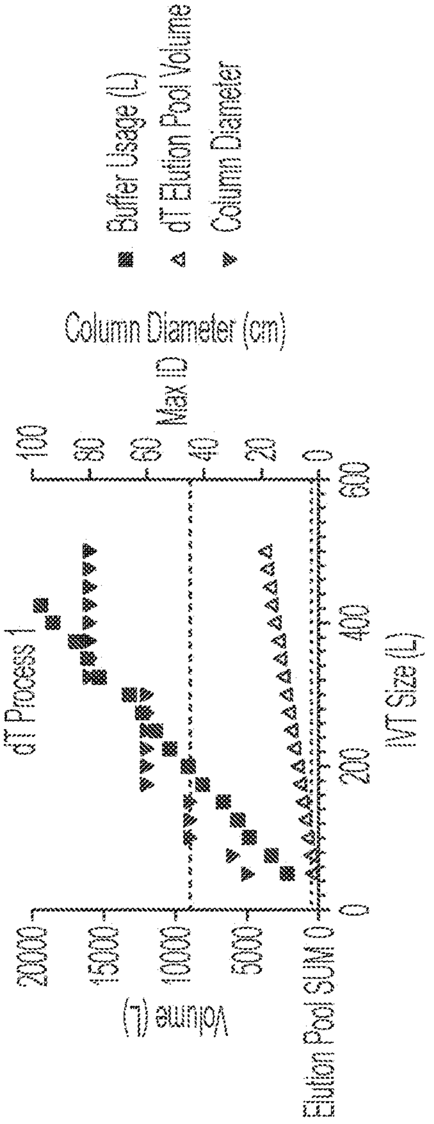
FIGS. 6A-6D show the effects of salt concentration on the efficiency of mRNA purification using dT chromatography-based purification.
Figure 6B:
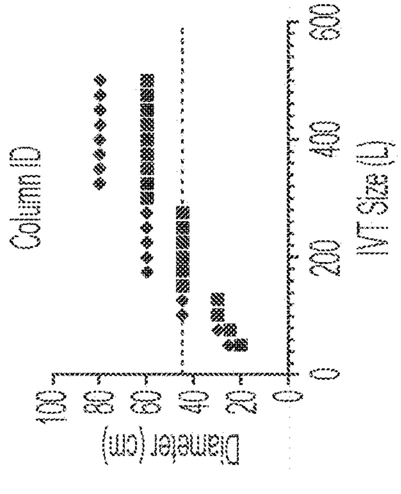
Figure 6C:
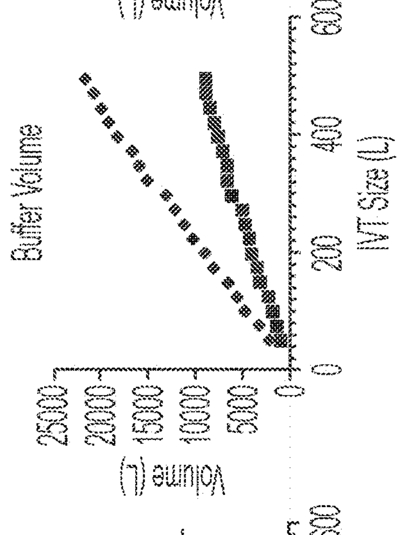
Figure 6D:
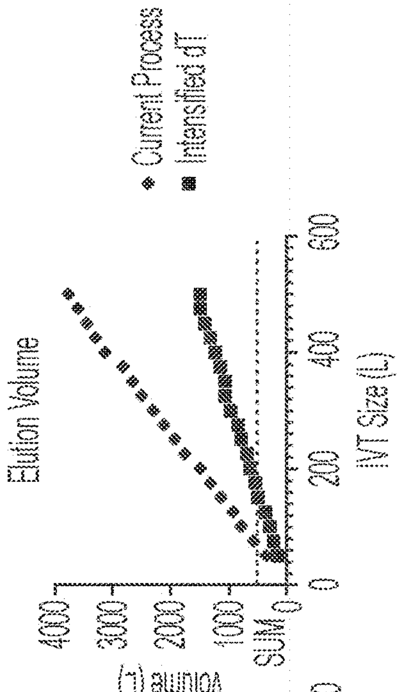

For each successive addition of feed solution and elution, feed solution (Load) and eluate (Runs) was analyzed for the amount of residual protein (rProtein) present in the feed solution or eluate (FIG. 5). Feed solutions continued to contain some residual protein, but residual protein levels were consistently low in eluates, indicating that MCC processes effectively removed residual protein from mRNA feed solutions.

Batch processes, single loopback MCC processes such as those described in Example 1, and parallel loopback MCC processes described in this Example were tested to measure productivity, in terms of mRNA purified per volume of resin and unit time, and percentage yield. In some single loopback MCC processes, and all parallel loopback MCC processes, mRNA feed solutions were supplemented with high-salt buffers to increase the salt concentration before applying the feed solution to the column. The results of these experiments are shown in Table 4. Like single loopback MCC processes, parallel loopback MCC processes markedly improved productivity and yields relative to batch chromatography processes. The benefits of parallel loopback MCC were most pronounced when mRNA feed solutions contained large amounts of mRNA, as the parallel loopback MCC purification at load challenges of 7.94 increased productivity by 20% and percent yield by 64%, relative to single loopback MCC under the same conditions. These results indicate that parallel loopback MCC allows efficient purification of mRNA from concentrated feed solutions, which can more efficiently saturate each chromatography column, with parallel capture of breakthrough mRNA by multiple columns preventing the loss of mRNA that may otherwise occur in single or batch processes, thereby maintaining percent yield.

TABLE 4

Comparative productivity of batch, single loopback MCC, and parallel loopback MCC processes.

| Process | mRNA load challenge (g/L) | NaCl (mM) | Cycle time (min) | Productivity ($g \cdot L^{-1} \cdot hr^{-1}$) | % yield |
|---|---|---|---|---|---|
| Batch | 1.80 | 100 | 57.4 | 1.7 | 92.0% |
| Batch (high-salt) | 5.00 | 500 | 78.0 | 3.1 | 79.9% |
| Single loopback MCC | 3.00 | 100 | 54.9 | 4.4 | 75.2% |
| Single loopback MCC process 1 (high-salt) | 5.50 | 350 | 64.9 | 4.7 | 82.4% |
| Parallel loopback MCC process 1 (high-salt) | 5.50 | 350 | 73.2 | 3.77 | 88.5% |
| Single loopback MCC process 2 (high-salt) | 7.94 | 300 | 54.9 | 3.5 | 41.2% |
| Parallel loopback MCC process 2 (high-salt) | 7.94 | 300 | 73.2 | 4.2 | 67.4% |

Example 4: Intensification of dT Chromatography Process

The relationship between the scale of an IVT reaction, and the parameters of an oligo-dT chromatography process for purifying mRNA from the IVT reaction, were analyzed. As an IVT reaction is scaled up, an oligo-dT chromatography process requires increasingly large columns to support binding of additional mRNA and volumes of buffer to support the chromatography (FIG. 5A). Furthermore, mRNA bound to oligo-dT columns must be eluted into larger volumes (FIG. 5A). This need for larger elution volumes quickly becomes rate-limiting, hindering the purification of mRNA from larger scale IVT reactions. However, intensifying the oligo-dT chromatography process by increasing the binding capacity of the oligo-dT columns reduced the required column size (FIG. 5B), buffer volume (FIG. 5C), and elution volume (FIG. 5D). Each of these reductions improved the efficiency of the oligo-dT chromatography process, allowing for IVT reactions to be scaled up without unduly affecting purification of the mRNA.

Figure 7A:
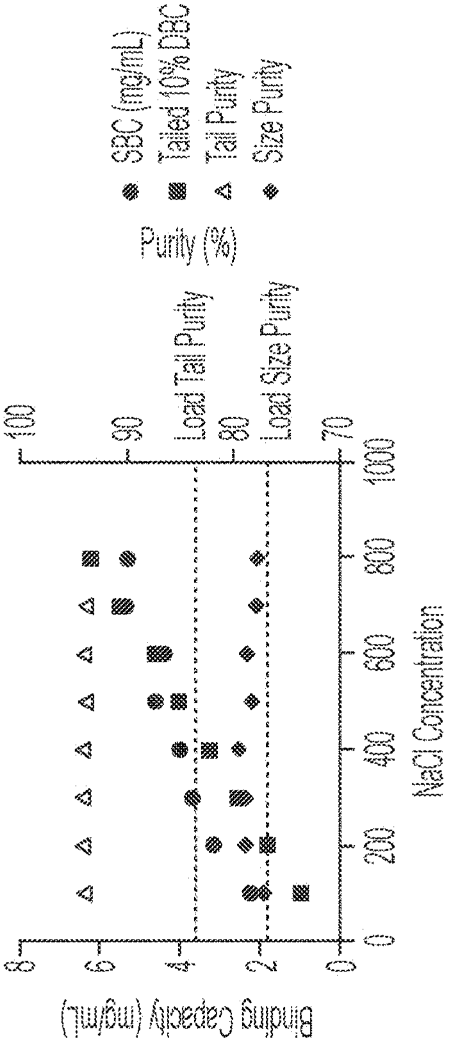
FIGS. 7A-7C show the relationship between salt concentration and parameters of dT chromatography.

The effects of salt concentration on binding capacities of mRNA to oligo-dT columns and purity of eluted mRNA were analyzed. Increasing salt concentrations improved both the static and dynamic binding capacity of mRNA to oligo-dT columns in a linear manner (FIG. 7A). Surprisingly, this improvement did not affect the percentages of eluted mRNAs that contained poly(A) tails or were of the expected length, indicating that increasing salt concentrations promote binding of mRNA to oligo-dT columns without adversely affecting mRNA purity.

Figure 7B:
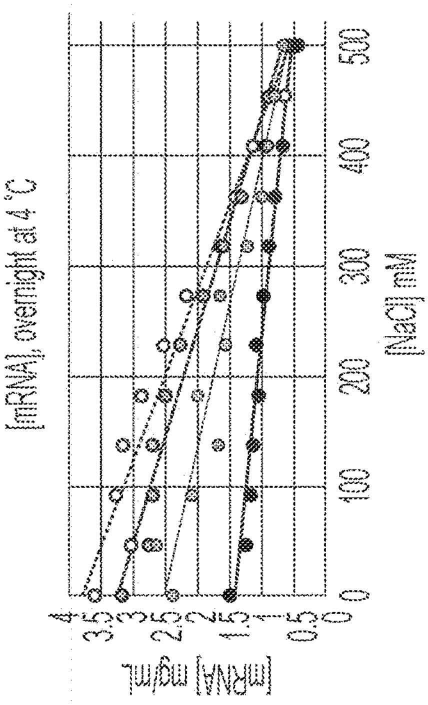
Figure 7C:
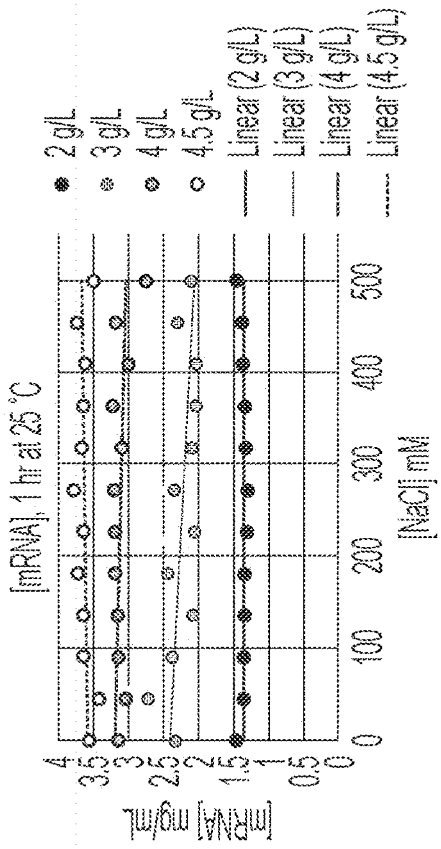

Because increasing the concentration of one solute (e.g., sodium chloride) in a solution may cause other solutes (e.g., nucleic acids) to precipitate, the relationship between salt concentration and mRNA solubility was analyzed. Varying concentrations of sodium chloride were added to solutions containing specified amounts of mRNA, and incubated for 1 hour at 25° C., or overnight at 4° C. Overnight incubation allowed mRNA beyond the threshold limit of 0.5 mg/mL to precipitate from solution (FIG. 7B). However, mRNA precipitation was negligible during brief incubations at room temperature, regardless of salt concentration (FIG. 7C). These results indicate that increased salt concentrations take time to cause the precipitation of mRNA. Therefore, increasing the salt concentration in an mRNA mixture shortly before adding it to an oligo-dT column promotes binding of mRNA to the column without causing unwanted precipitation. Accordingly, increasing salt concentrations are useful for increasing the dynamic binding capacity of a column, thereby improving the efficiency of the oligo-dT chromatography process. As shown in Tables 5-6, the addition of high-salt buffer before adding the mRNA composition to the oligo-dT resin reduces the total processing time or column volume, and consequently oligo-dT resin volume, required to purify mRNA from the composition by 46% to 56%, respectively. In both cases, this improved efficiency increases the productivity of mRNA purification, in terms of (mass)·(volume of stationary phase)$^{-1}$·(time)$^{-1}$ (e.g., $g \cdot L^{-1} \cdot hr^{-1}$). Furthermore, salt intensification of oligo-dT chromatography reduced the amount of buffer required to purify the mRNA by 52%-68%.

TABLE 5

Oligo-dT chromatography process 1 with salt intensification.

| | Process 1 | Process 1 with 500 mM NaCl (same column) | Process 1 with 500 mM NaCl (smaller column) |
|---|---|---|---|
| Column diameter (cm) | 45 | 45 | 30 |
| Chromatography cycle duration (min) | 57.4 | 80.7 | 78.2 |
| Number of cycles | 11 | 4 | 10 |
| Chromatography duration (hr) | 11.3 | 6.1 | 13.8 |
| Buffer used (L) | 3125 | 1306 | 1315 |

TABLE 6

Oligo-dT chromatography process 2 with salt intensification.

| | Process 2 | Process 2 with 500 mM NaCl (same column) | Process 2 with 500 mM NaCl (smaller column) |
|---|---|---|---|
| Column diameter (cm) | 45 | 45 | 30 |
| Chromatography cycle duration (min) | 68.5 | 69.9 | 72.1 |
| Number of cycles | 11 | 4 | 10 |
| Chromatography duration (hr) | 12.8 | 6.6 | 12.8 |
| Buffer used (L) | 4119 | 1849 | 1311 |

EQUIVALENTS AND SCOPE

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in some embodiments, to A only (optionally including elements other than B); in another embodiment, to B only (optionally including elements other than A); in yet another embodiment, to both A and B (optionally including other elements); etc. As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in some embodiments, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc. Each possibility represents a separate embodiment of the present invention.

It should be understood that, unless clearly indicated to the contrary, the disclosure of numerical values and ranges of numerical values in the specification includes both i) the exact value(s) or range specified, and ii) values that are "about" the value(s) or ranges specified (e.g., values or ranges falling within a reasonable range (e.g., about 10% similar)) as would be understood by a person of ordinary skill in the art.

It should also be understood that, unless clearly indicated to the contrary, in any methods disclosed herein that include more than one step or act, the order of the steps or acts of the method is not necessarily limited to the order in which the steps or acts of the method are disclosed.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of purifying a nucleic acid using at least three chromatography columns capable of being used in series, the method comprising:

(i)(a) loading a first chromatography column by contacting a first stationary phase of the first chromatography column with a feed solution comprising one or more nucleic acids, optionally wherein the one or more nucleic acids comprise mRNAs;

(ii)(a) loading a second chromatography column by contacting, in series with the first chromatography column, a second stationary phase of the second chromatography column with a flowthrough of the first column formed after the feed solution has contacted the first stationary phase of the first chromatography column;

(iii)(a) contacting the second stationary phase with a portion of the feed solution that has not been contacted with the first stationary phase;

(iii)(b) contacting, in series with the second chromatography column, a third stationary phase of a third chromatography column with a flowthrough of the second chromatography column formed after the feed solution has contacted the second stationary phase of the second chromatography column; and (iv)(a) eluting the one or more nucleic acids from the first chromatography column.

2. The method of claim 1, wherein the eluting from the first chromatography column is under conditions in which the first and second chromatography columns are not in series.

3. The method of claim 1, wherein the at least three chromatography columns capable of being used in series comprise 4, 5, 6, 7, 8, or more chromatography columns.

4. The method of claim 3, wherein the at least three chromatography columns capable of being used in series comprise at least eight chromatography columns, wherein:

i) the first chromatography column is capable of being used in series with the eighth and second chromatography column;

ii) the second chromatography column is capable of being used in series with the first and third chromatography columns;

iii) the third chromatography column is capable of being used in series with the second and fourth chromatography columns;

iv) the fourth chromatography column is capable of being used in series with the third and fifth chromatography columns;

v) the fifth chromatography column is capable of being used in series with the fourth and sixth chromatography columns;

vi the sixth chromatography column is capable of being used in series with the fifth and seventh chromatography columns; and vii) the seventh chromatography column is capable of being used in series with the sixth and eight chromatography column.

5. The method of claim 1, wherein the method further comprises:

contacting a last stationary phase of a last chromatography column with an additional portion of the feed solution that has not been contacted with a stationary phase; and contacting, in series with the last chromatography column, the first stationary phase of the first chromatography column with a flowthrough of the last chromatography column formed after the feed solution has contacted the last stationary phase of the last chromatography column.

6. The method of claim 1, further comprising:

(ii)(b) loading a third chromatography column in parallel with the second chromatography column by contacting, in series with the first chromatography column, a third stationary phase of the third chromatography column with a flowthrough of the first chromatography column formed after the feed solution has contacted the first stationary phase of the first chromatography column.

7. A method of purifying a nucleic acid using at least four chromatography columns, wherein each column is capable of being used in series and in parallel with two or more other columns, the method comprising:

(i) loading a first chromatography column by contacting a first stationary phase of a first chromatography column with a feed solution comprising one or more nucleic acids, optionally wherein the one or more nucleic acids are mRNAs;

(ii) loading a second chromatography column and a third chromatography column in parallel by contacting, in series with the first chromatography column, (a) a second stationary phase of the second chromatography column with a first portion of a flowthrough of the first chromatography column formed after the feed solution has contacted the first stationary phase of the first chromatography column, and (b) a third stationary phase of the third chromatography column with a second portion of the flowthrough of the first chromatography column;

(iii) loading the second chromatography column by contacting the second stationary phase with a portion of the feed solution that has not been contacted with the first stationary phase;

(iv) loading the third chromatography column and a fourth chromatography column in parallel by contacting, in series with the second chromatography column, (a) the third stationary phase of the third chromatography column with a flowthrough of the second chromatography column formed after the feed solution has contacted the second stationary phase of the second chromatography column, and (b) a fourth stationary phase of the fourth chromatography column with the flowthrough of the second chromatography column; and (iv)(a) eluting the one or more nucleic acids from the first chromatography column.

8. The method of claim 7, wherein the at least four chromatography columns comprise 5, 6, 7, 8, 9, 10, or more chromatography columns.

9. The method of claim 7, wherein output of each chromatography column capable of being directed into 2, 3, 4, 5, 6, 7, or 8 other chromatography columns.

10. The method of claim 9, wherein the at least four chromatography columns comprise at least eight chromatography columns, wherein:

i) the first chromatography column is capable of being used in series with the second and third chromatography columns in parallel;

ii) the second chromatography column is capable of being used in series with the third and fourth chromatography columns in parallel;

iii) the third chromatography column is capable of being used in series with the fourth and fifth chromatography columns in parallel;

iv) the fourth chromatography column is capable of being used in series with the fifth and sixth chromatography columns in parallel;

v) the fifth chromatography column is capable of being used in series with the sixth and seventh chromatography columns in parallel;

vi) the sixth chromatography column is capable of being used in series with the seventh and eighth chromatography columns in parallel;

vii) the seventh chromatography column is capable of being used in series with the eighth and first chromatography columns in parallel; and viii) the eighth chromatography column is capable of being used in series with the first and second chromatography columns in parallel.

11. The method of claim 7, further comprising:

contacting a last stationary phase of a last chromatography column with an additional portion of the feed solution that has not been contacted with a stationary phase; and in series with the last chromatography column, contacting in parallel (a) the first stationary phase of the first chromatography column with a first portion of a flowthrough of the last chromatography column formed after the feed solution has contacted the last stationary phase of the last chromatography column, and (b) the second stationary phase of the second chromatography column with a second portion of the flowthrough of the last chromatography column.

12. The method of claim 1, wherein one or more, and optionally all, of the chromatography columns are independently capable of directing material to a different chromatography column used in series, a waste collection area, and a product collection area.

13. The method of claim 1, wherein the chromatography columns capable of being used in series comprise five or more chromatography columns, wherein the following steps are conducted at the same time: at least one column is loaded with feed solution; at least one column is washed; at least one column is eluted; at least once column is cleaned; and at least one column is equilibrated.

14. The method of claim 1, wherein the method further comprises:

(ii)(b) contacting the first stationary phase with a washing solution, wherein output comprising the washing solution is directed to a waste collection area.

15. The method of claim 7, wherein the method further comprises:

(iv)(b) contacting the first stationary phase with a cleaning solution, wherein the output comprising the cleaning solution is directed to a waste collection area.

16. The method of claim 15, wherein the method further comprises:

(iv)(c) contacting the first stationary phase with an equilibration solution, wherein the output comprising the equilibration solution is directed to a waste collection area.

17. The method of claim 1, wherein the one or more nucleic acids are mRNAs, wherein each of the stationary phases comprises oligo-dT.

18. The method of claim 1, wherein the one or more nucleic acids are mRNAs, wherein the feed solution comprises about 2 mg/mL to about 5 mg/mL mRNA, about 2.25 mg/mL to about 4 mg/mL mg/mL mRNA, or about 2.5 mg/mL to about 3 mg/mL mRNA.

19. The method of claim 1, wherein the one or more nucleic acids are mRNAs, wherein the loading of the first chromatography column comprises contacting the first stationary phase with at least 2 g, at least 3 g, at least 4 g, at least 5 g, at least 6 g, at least 7 g, at least 8 g, at least 9 g, at least 10 g, or more mRNA per L of stationary phase present in the first chromatography column.

20. The method of claim 1, wherein the one or more nucleic acids are mRNAs, wherein a high-salt buffer is added to the feed solution before the loading of (i)(a), such that the feed solution has a salt concentration of about 300 mM to about 600 mM when added to the first stationary phase, wherein the loading of (i)(a) occurs within 5 minutes or less, 4 minutes or less, 3 minutes or less, 2 minutes or less, or 1 minute or less of the addition of the high-salt buffer.

* * * * *